(12) United States Patent
Weiman et al.

(10) Patent No.: US 10,835,387 B2
(45) Date of Patent: Nov. 17, 2020

(54) EXPANDABLE FUSION DEVICE AND METHOD OF INSTALLATION THEREOF

(71) Applicant: GLOBUS MEDICAL, INC., Audubon, PA (US)

(72) Inventors: Mark Weiman, Downingtown, PA (US); Hilliary Kopp, Berwyn, PA (US)

(73) Assignee: Globus Medical Inc., Audubon, PA (US)

( * ) Notice: Subject to any disclaimer, the term of this patent is extended or adjusted under 35 U.S.C. 154(b) by 0 days.

(21) Appl. No.: 15/815,065

(22) Filed: Nov. 16, 2017

(65) Prior Publication Data

US 2018/0116816 A1    May 3, 2018

Related U.S. Application Data

(60) Continuation-in-part of application No. 15/189,188, filed on Jun. 22, 2016, now Pat. No. 10,085,849.
(Continued)

(51) Int. Cl.
| | | |
|---|---|---|
| *A61F 2/44* | (2006.01) | |
| *A61F 2/30* | (2006.01) | |
| *A61F 2/46* | (2006.01) | |

(52) U.S. Cl.
CPC .............. *A61F 2/447* (2013.01); *A61F 2/44* (2013.01); *A61F 2/442* (2013.01); *A61F 2/446* (2013.01); *A61F 2/4455* (2013.01); *A61F 2/4611* (2013.01); *A61F 2002/3039* (2013.01); *A61F 2002/30266* (2013.01); *A61F 2002/30387* (2013.01); *A61F 2002/30405* (2013.01); *A61F 2002/30411* (2013.01); *A61F 2002/30471* (2013.01); *A61F 2002/30482* (2013.01); *A61F 2002/30484* (2013.01); *A61F 2002/30507* (2013.01); *A61F 2002/30515* (2013.01); *A61F 2002/30517* (2013.01); *A61F 2002/30522* (2013.01); *A61F 2002/30523* (2013.01); *A61F 2002/30538* (2013.01);
(Continued)

(58) Field of Classification Search
CPC .. A61F 2/442; A61F 2/4425; A61F 2002/443; A61F 2/4455; A61F 2/447
USPC ..................... 606/246–249; 623/17.11–17.16
See application file for complete search history.

(56) References Cited

U.S. PATENT DOCUMENTS

| | | |
|---|---|---|
| 4,349,921 A | 9/1982 | Kuntz |
| 4,599,086 A | 7/1986 | Doty |

(Continued)

FOREIGN PATENT DOCUMENTS

| | | |
|---|---|---|
| CA | 2088066 A1 | 1/1992 |
| DE | 4012622 C1 | 7/1991 |

(Continued)

*Primary Examiner* — Julianna N Harvey
*Assistant Examiner* — Christina Negrellirodriguez

(57) ABSTRACT

The present invention provides an expandable fusion device capable of being installed inside an intervertebral disc space to maintain normal disc spacing and restore spinal stability, thereby facilitating an intervertebral fusion. In one embodiment, the fusion device includes body, a first endplate, and a second endplate, a middle ramp piece, a stem, and two ramp pins. The middle ramped piece is operable to move to generate lordotic expansion of the first and second endplates followed by parallel expansion. The fusion device is operable to be deployed down an endoscopic tube.

10 Claims, 65 Drawing Sheets

Related U.S. Application Data which is a continuation-in-part of application No. 15/014,189, filed on Feb. 3, 2016, now Pat. No. 9,907,673, which is a continuation-in-part of application No. 14/109,429, filed on Dec. 17, 2013, now Pat. No. 9,370,434, which is a division of application No. 12/875,818, filed on Sep. 3, 2010, now Pat. No. 8,632,595.

(52) U.S. Cl.
CPC .............. *A61F 2002/30556* (2013.01); *A61F 2002/30558* (2013.01); *A61F 2002/30579* (2013.01); *A61F 2002/30593* (2013.01); *A61F 2002/30601* (2013.01); *A61F 2002/30622* (2013.01); *A61F 2002/30841* (2013.01); *A61F 2002/30843* (2013.01); *A61F 2002/30904* (2013.01); *A61F 2220/0016* (2013.01); *A61F 2310/00011* (2013.01); *A61F 2310/00017* (2013.01); *A61F 2310/00023* (2013.01); *A61F 2310/00179* (2013.01)

(56) References Cited

U.S. PATENT DOCUMENTS

| | | |
|---|---|---|
| 4,863,476 A | 9/1989 | Shepperd |
| 4,863,477 A | 9/1989 | Monson |
| 5,123,926 A | 6/1992 | Pisharodi |
| 5,290,312 A | 3/1994 | Kojimoto et al. |
| 5,306,310 A | 4/1994 | Siebels |
| 5,375,823 A | 12/1994 | Navas |
| 5,390,683 A | 2/1995 | Pisharodi |
| 5,522,899 A | 6/1996 | Michelson |
| 5,534,030 A | 7/1996 | Navarro et al. |
| 5,554,191 A | 9/1996 | Lahille et al. |
| 5,571,192 A | 11/1996 | Schonhoffer |
| 5,645,596 A | 7/1997 | Kim |
| 5,653,763 A | 8/1997 | Errico et al. |
| 5,665,122 A | 9/1997 | Kambin |
| 5,676,701 A | 10/1997 | Yuan et al. |
| 6,039,761 A | 3/2000 | Li et al. |
| 6,045,579 A | 4/2000 | Hochschuler et al. |
| 6,080,193 A | 6/2000 | Hochshuler |
| 6,099,531 A | 8/2000 | Bonutti |
| 6,126,689 A | 10/2000 | Brett |
| 6,176,882 B1 * | 1/2001 | Biedermann ............ A61F 2/447 623/17.11 |
| 6,258,125 B1 | 7/2001 | Paul et al. |
| 6,558,423 B1 | 5/2003 | Michelson |
| 6,562,074 B2 | 5/2003 | Gerbec et al. |
| 6,576,016 B1 | 6/2003 | Hochschuler et al. |
| 6,554,863 B2 | 8/2003 | Paul et al. |
| 6,641,614 B1 | 11/2003 | Wagner et al. |
| 6,648,917 B2 | 11/2003 | Gerbec et al. |
| 6,666,891 B2 | 12/2003 | Boehm, Jr. et al. |
| 6,692,495 B1 | 2/2004 | Zacouto |
| 6,706,070 B1 | 3/2004 | Wagner et al. |
| 6,752,832 B2 | 6/2004 | Ulrich |
| 6,814,756 B1 | 11/2004 | Michelson |
| 6,830,589 B2 | 12/2004 | Erickson |
| 6,849,093 B2 | 2/2005 | Michelson |
| 6,852,129 B2 | 2/2005 | Gerbec et al. |
| 6,863,673 B2 | 3/2005 | Gerbec et al. |
| 6,881,228 B2 | 4/2005 | Zdeblick et al. |
| 7,018,415 B1 | 3/2006 | McKay |
| 7,070,598 B2 | 7/2006 | Lim et al. |
| 7,204,853 B2 | 4/2007 | Gordon |
| 7,217,291 B2 | 5/2007 | Zucherman et al. |
| 7,282,063 B2 | 10/2007 | Cohen et al. |
| 7,316,714 B2 | 1/2008 | Gordon |
| 7,431,735 B2 | 10/2008 | Liu et al. |
| 7,473,276 B2 | 1/2009 | Aebi et al. |
| 7,547,325 B2 | 6/2009 | Biedermann et al. |
| 7,621,953 B2 | 11/2009 | Braddock, Jr. et al. |
| 7,641,693 B2 | 1/2010 | Gutlin et al. |
| 7,682,396 B2 | 3/2010 | Beaurain et al. |
| 7,749,270 B2 | 7/2010 | Peterman |
| 7,753,958 B2 | 7/2010 | Gordon |
| 7,763,074 B2 | 7/2010 | Altarac et al. |
| 7,771,473 B2 | 8/2010 | Thramann |
| 7,780,732 B2 | 8/2010 | Abernathie |
| 7,799,081 B2 | 9/2010 | McKinley |
| 7,815,683 B2 | 10/2010 | Melkent et al. |
| 7,837,734 B2 | 11/2010 | Zucherman et al. |
| 7,875,078 B2 | 1/2011 | Wysocki et al. |
| 7,901,409 B2 | 3/2011 | Canaveral et al. |
| 7,909,869 B2 | 3/2011 | Gordon |
| 7,951,199 B2 | 5/2011 | Miller |
| 8,062,375 B2 | 11/2011 | Glerum |
| 8,123,810 B2 | 2/2012 | Gordon |
| 8,137,405 B2 | 3/2012 | Kostuik |
| 8,647,386 B2 | 2/2014 | Gordon |
| 9,005,291 B2 | 4/2015 | Loebl et al. |
| 9,233,009 B2 * | 1/2016 | Gray .................... A61F 2/4465 |
| 2002/0045945 A1 | 4/2002 | Liu |
| 2002/0068976 A1 | 6/2002 | Jackson |
| 2002/0068977 A1 | 6/2002 | Jackson |
| 2004/0030387 A1 | 2/2004 | Landry |
| 2004/0049271 A1 | 3/2004 | Biedermann |
| 2004/0054412 A1 | 3/2004 | Gerbec et al. |
| 2004/0153065 A1 | 8/2004 | Lim |
| 2005/0021041 A1 | 1/2005 | Michelson |
| 2005/0021145 A1 | 1/2005 | de Villiers |
| 2005/0033432 A1 | 2/2005 | Gordon |
| 2005/0080422 A1 | 4/2005 | Otte |
| 2005/0113916 A1 | 5/2005 | Branch, Jr. |
| 2005/0149188 A1 | 7/2005 | Cook |
| 2005/0171541 A1 | 8/2005 | Boehm |
| 2005/0251258 A1 | 11/2005 | Jackson |
| 2005/0273171 A1 | 12/2005 | Gordon |
| 2005/0273174 A1 | 12/2005 | Gordon |
| 2005/0278026 A1 | 12/2005 | Gordon |
| 2005/0283244 A1 | 12/2005 | Gordon |
| 2005/0283245 A1 | 12/2005 | Gordon |
| 2006/0004453 A1 | 1/2006 | Bartish, Jr. et al. |
| 2006/0015184 A1 | 1/2006 | Winterbottom |
| 2006/0058878 A1 | 3/2006 | Michelson |
| 2006/0084986 A1 | 4/2006 | Grinberg |
| 2006/0122701 A1 | 6/2006 | Kister |
| 2006/0129244 A1 | 6/2006 | Ensign |
| 2006/0142859 A1 | 6/2006 | McLuen |
| 2006/0149385 A1 | 7/2006 | McKay |
| 2006/0195192 A1 | 8/2006 | Gordon et al. |
| 2006/0229729 A1 | 10/2006 | Gordon |
| 2006/0241770 A1 | 10/2006 | Rhoda |
| 2006/0253201 A1 | 11/2006 | Mcluen |
| 2007/0043442 A1 | 2/2007 | Abernathie |
| 2007/0050030 A1 | 3/2007 | Kim |
| 2007/0050032 A1 | 3/2007 | Gittings et al. |
| 2007/0055377 A1 | 3/2007 | Hanson et al. |
| 2007/0191951 A1 | 8/2007 | Branch |
| 2007/0255415 A1 | 11/2007 | Edie et al. |
| 2007/0270963 A1 | 11/2007 | Melkent et al. |
| 2007/0270968 A1 | 11/2007 | Baynham |
| 2008/0021559 A1 | 1/2008 | Thramann |
| 2008/0065222 A1 | 3/2008 | Hamada |
| 2008/0114467 A1 | 5/2008 | Capote |
| 2008/0140207 A1 | 6/2008 | Olmos et al. |
| 2008/0147194 A1 | 6/2008 | Grotz |
| 2008/0167657 A1 | 7/2008 | Greenhalgh |
| 2008/0183204 A1 | 7/2008 | Greenhalgh et al. |
| 2008/0221694 A1 | 9/2008 | Warnick |
| 2008/0275455 A1 | 11/2008 | Berry et al. |
| 2008/0281346 A1 | 11/2008 | Greenhalgh et al. |
| 2008/0288073 A1 | 11/2008 | Renganath et al. |
| 2008/0300598 A1 | 12/2008 | Barreiro et al. |
| 2008/0306488 A1 | 12/2008 | Altarac et al. |
| 2008/0319487 A1 | 12/2008 | Fielding et al. |
| 2008/0319549 A1 | 12/2008 | Greenhalgh et al. |
| 2009/0024217 A1 | 1/2009 | Levy |
| 2009/0076616 A1 | 3/2009 | Duggal |
| 2009/0125062 A1 | 5/2009 | Arnin |
| 2009/0149956 A1 | 6/2009 | Greenhalgh et al. |

(56) References Cited

U.S. PATENT DOCUMENTS

| | | |
|---|---|---|
| 2009/0149959 A1 | 6/2009 | Conner et al. |
| 2009/0204218 A1 | 8/2009 | Richelsoph |
| 2009/0222100 A1 | 9/2009 | Cipoletti et al. |
| 2009/0240334 A1 | 9/2009 | Richelsoph |
| 2009/0270989 A1 | 10/2009 | Conner et al. |
| 2009/0281628 A1 | 11/2009 | Oglaza et al. |
| 2009/0292361 A1 | 11/2009 | Lopez |
| 2009/0299478 A1 | 12/2009 | Carls et al. |
| 2009/0312763 A1 | 12/2009 | McCormack |
| 2010/0049324 A1 | 2/2010 | Valdevit |
| 2010/0070041 A1 | 3/2010 | Peterman |
| 2010/0082109 A1 | 4/2010 | Greenhalgh et al. |
| 2010/0179657 A1 | 7/2010 | Greenhalgh et al. |
| 2010/0211176 A1 | 8/2010 | Greenhalgh |
| 2010/0222816 A1 | 9/2010 | Gabelberger |
| 2010/0286783 A1 | 11/2010 | Lechmann |
| 2011/0035011 A1 | 2/2011 | Cain |
| 2011/0093074 A1* | 4/2011 | Glerum .................. A61F 2/447 623/17.16 |
| 2011/0160861 A1 | 6/2011 | Jimenez |
| 2011/0172719 A1 | 7/2011 | Gorhan et al. |
| 2011/0172774 A1 | 7/2011 | Varela |
| 2011/0276142 A1 | 11/2011 | Niemiec |
| 2011/0301713 A1 | 12/2011 | Theofilos |
| 2011/0319997 A1 | 12/2011 | Glerum |
| 2012/0035729 A1 | 2/2012 | Glerum |
| 2012/0059470 A1 | 3/2012 | Weiman |
| 2012/0059472 A1 | 3/2012 | Weiman |
| 2012/0059475 A1 | 3/2012 | Weiman |
| 2012/0109308 A1 | 5/2012 | Lechmann |
| 2012/0130496 A1 | 5/2012 | Duffield |
| 2012/0165945 A1 | 6/2012 | Hansell |
| 2012/0185049 A1 | 7/2012 | Varela |
| 2012/0209386 A1 | 8/2012 | Triplett |
| 2012/0215313 A1 | 8/2012 | Saidha |
| 2012/0265309 A1 | 10/2012 | Glerum |
| 2012/0277870 A1 | 11/2012 | Wolters |
| 2012/0323329 A1 | 12/2012 | Jimenez |
| 2012/0330426 A1 | 12/2012 | McLaughlin |
| 2013/0023993 A1 | 1/2013 | Weiman |
| 2013/0023994 A1 | 1/2013 | Glerum |
| 2013/0158664 A1 | 6/2013 | Palmatier et al. |
| 2013/0158669 A1 | 6/2013 | Sungarian |
| 2013/0190825 A1 | 7/2013 | Perrow et al. |
| 2014/0277471 A1 | 9/2014 | Gray et al. |
| 2014/0277489 A1 | 9/2014 | Davenport et al. |
| 2015/0057755 A1 | 2/2015 | Suddaby et al. |
| 2015/0112437 A1 | 4/2015 | Davis et al. |
| 2015/0223946 A1 | 8/2015 | Weiman et al. |
| 2015/0374512 A1 | 12/2015 | Glerum et al. |
| 2016/0361176 A1 | 12/2016 | Weiman et al. |
| 2017/0268561 A1 | 9/2017 | Hess et al. |

FOREIGN PATENT DOCUMENTS

| | | |
|---|---|---|
| DE | 4327054 C1 | 4/1995 |
| EP | 0576379 B1 | 6/1993 |
| EP | 0610837 B1 | 7/1994 |
| FR | 2794968 | 12/2000 |
| JP | 2000-513263 | 10/2000 |
| JP | 2008-522722 A | 7/2008 |
| JP | 6-249221 A | 7/2015 |
| JP | 2016-512108 A | 4/2016 |
| SU | 1424826 A1 | 9/1988 |
| WO | 9201428 A1 | 2/1992 |
| WO | 9525485 A1 | 9/1995 |
| WO | 199942062 A1 | 8/1999 |
| WO | 199966867 A1 | 12/1999 |
| WO | 2002045625 A1 | 6/2002 |
| WO | 2004019829 A1 | 3/2004 |
| WO | 2004069033 A2 | 8/2004 |
| WO | 2006045094 A2 | 4/2006 |
| WO | 2006047587 A2 | 5/2006 |
| WO | 2006113080 A2 | 10/2006 |
| WO | 2008044057 A1 | 4/2008 |
| WO | 2008134515 A1 | 11/2008 |
| WO | 2009114381 A1 | 9/2009 |
| WO | 2009124269 A1 | 10/2009 |
| WO | 2012031267 A1 | 3/2012 |
| WO | 2014165319 A1 | 10/2014 |
| WO | 2015187569 A1 | 12/2015 |
| WO | 2016069796 A1 | 5/2016 |
| WO | 2017015244 A2 | 1/2017 |
| WO | 2017015244 A3 | 1/2017 |
| WO | 2017117513 A1 | 7/2017 |
| WO | 2017136620 A1 | 8/2017 |

* cited by examiner

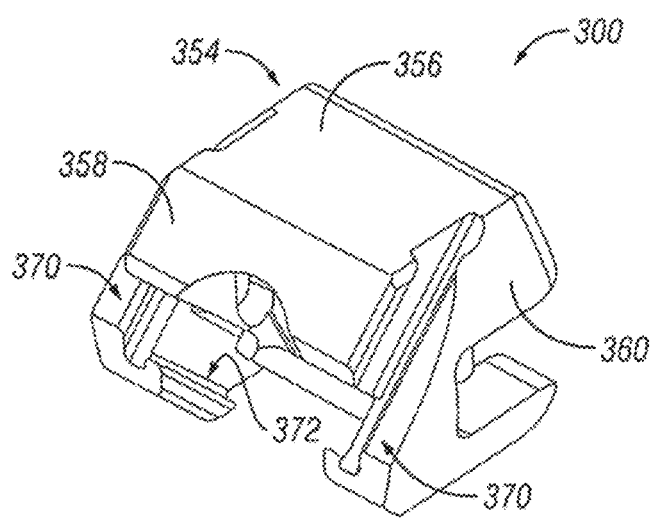
FIG. 47
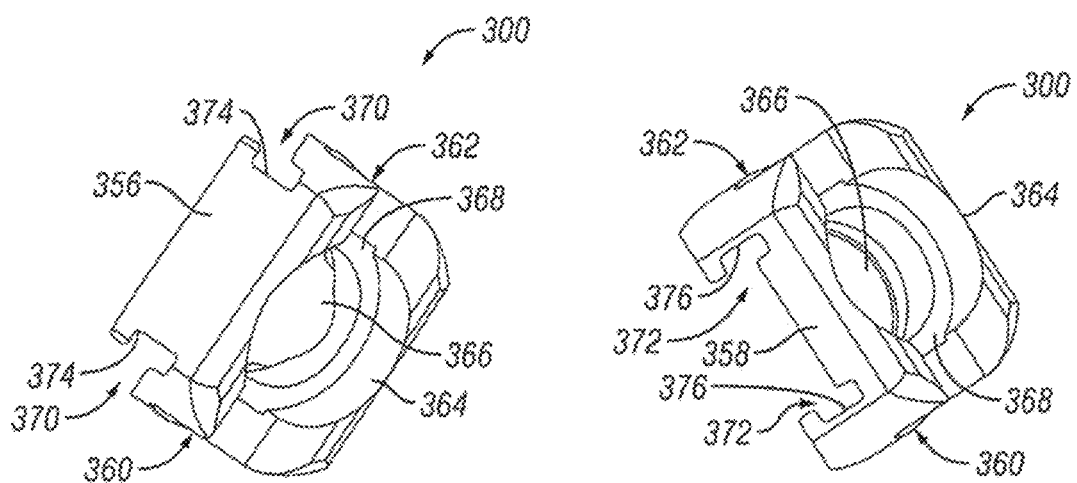
FIG. 48
FIG. 49

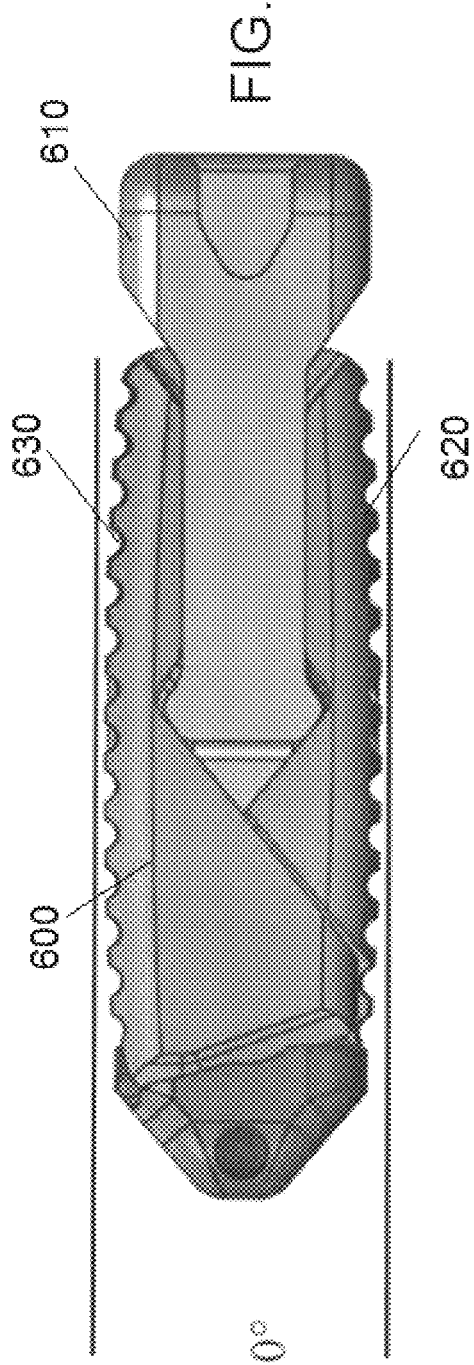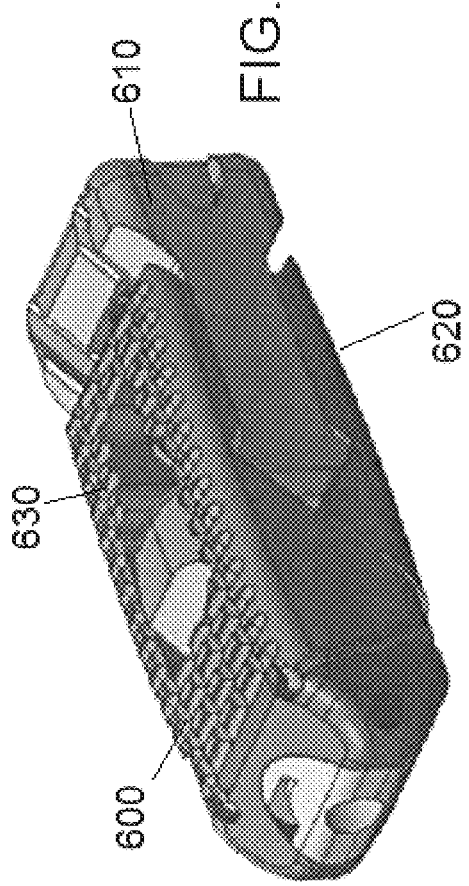

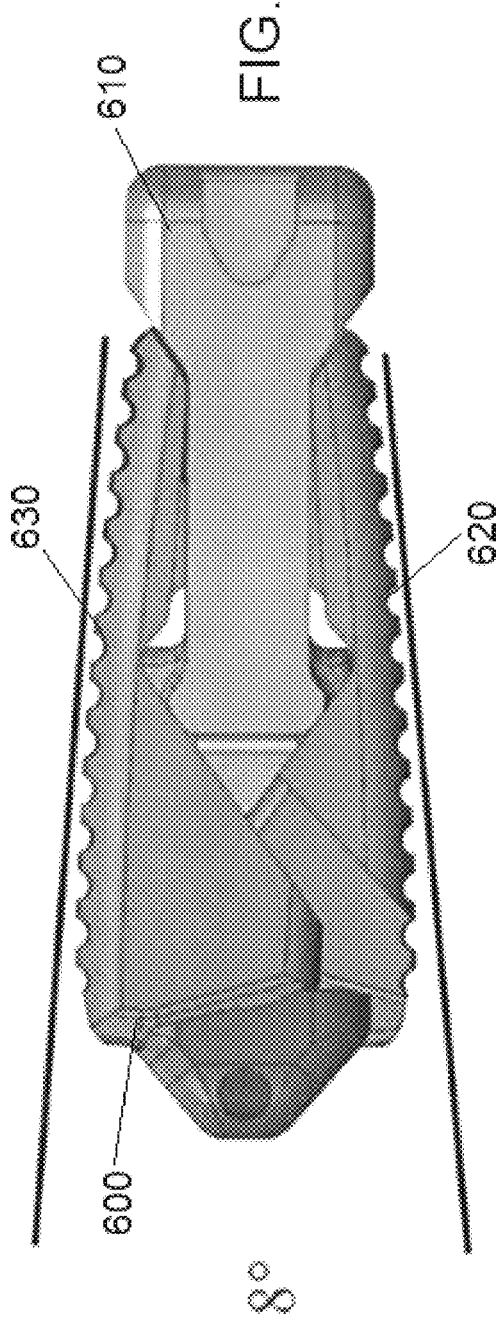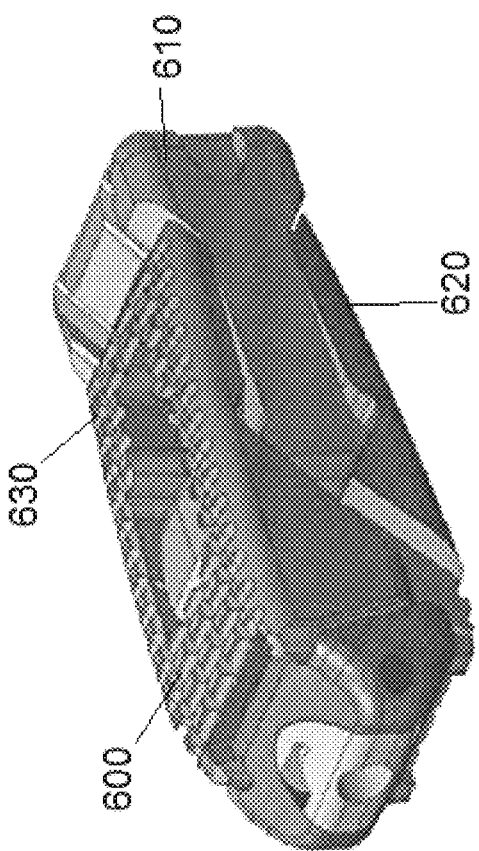

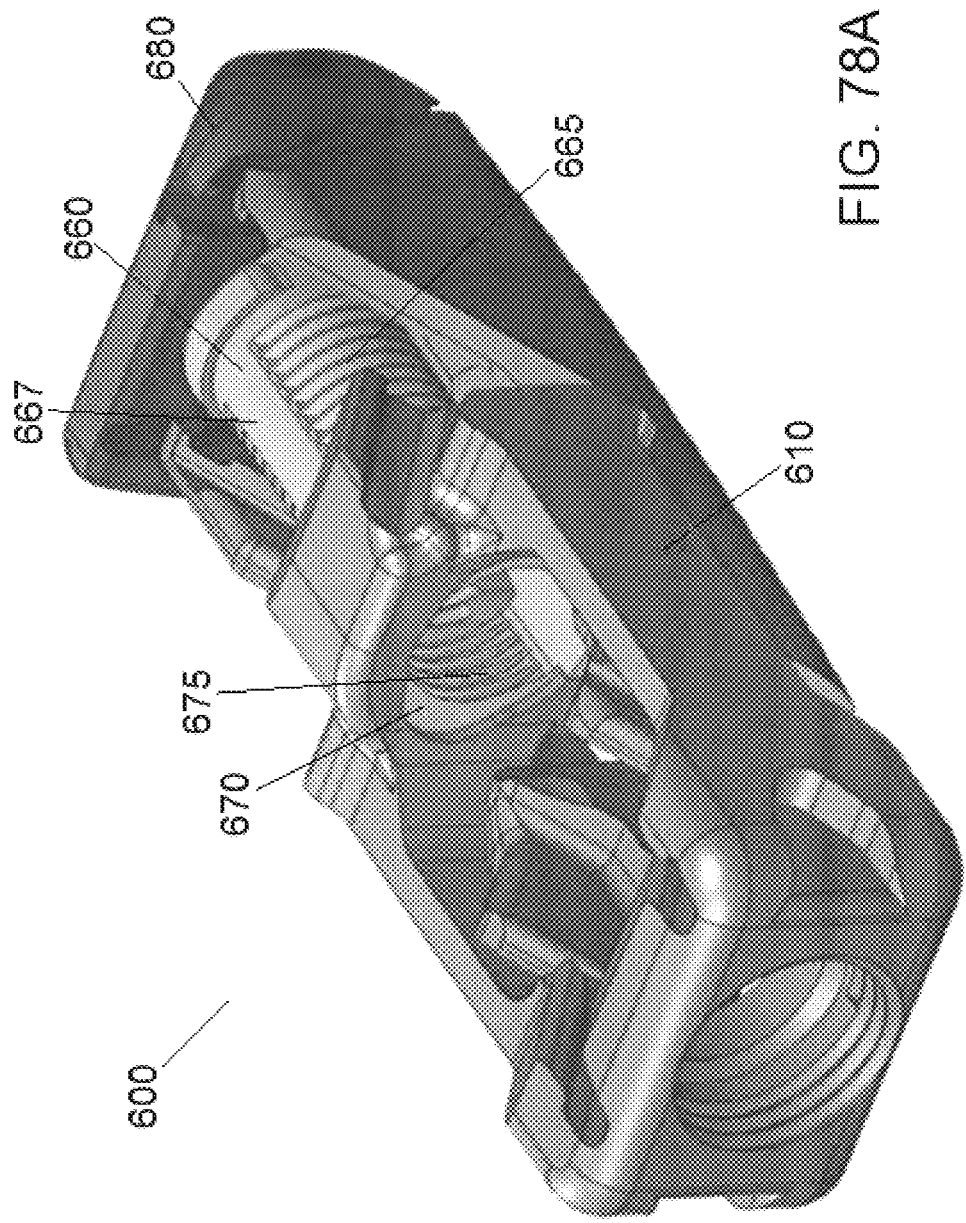

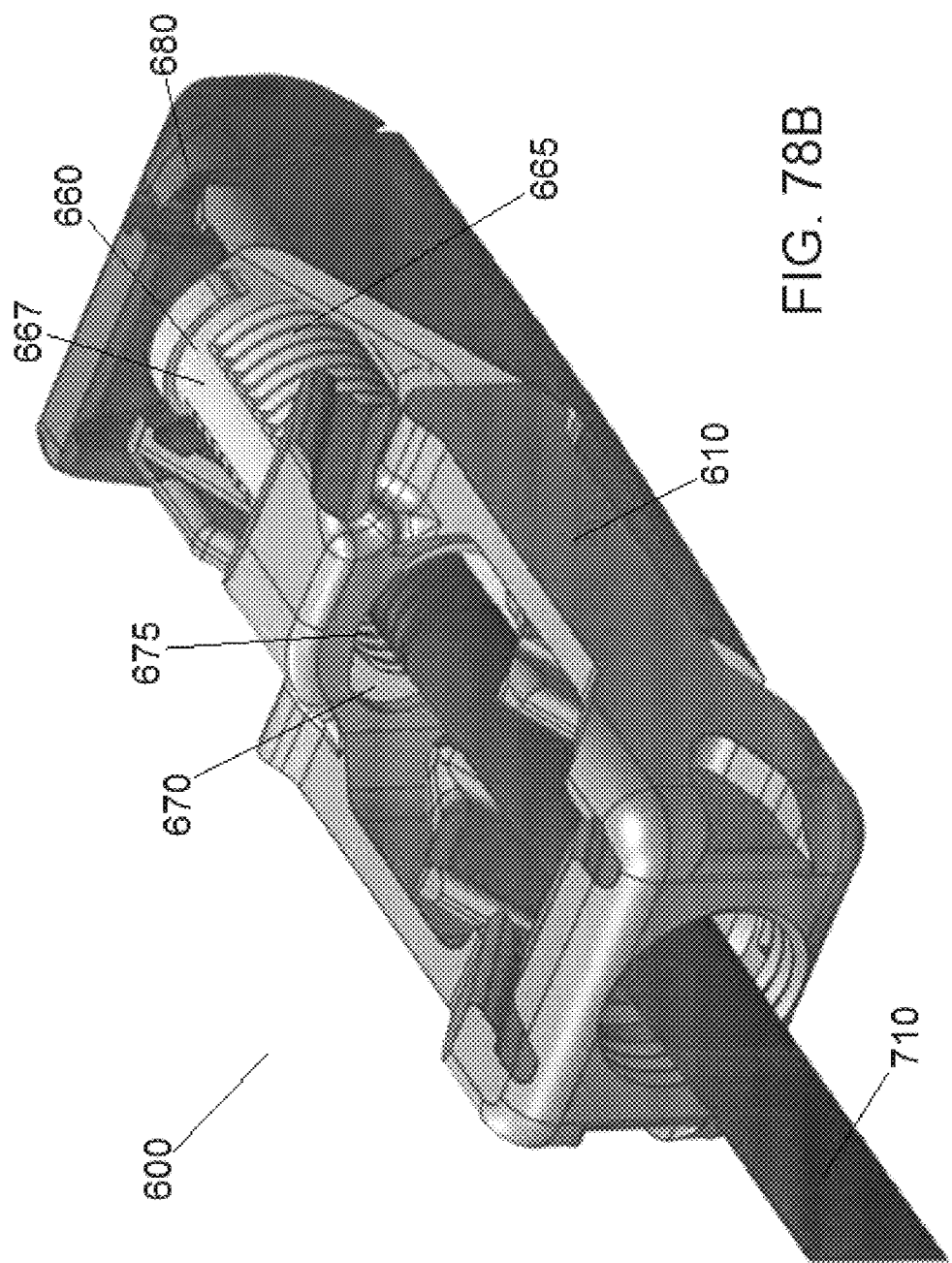

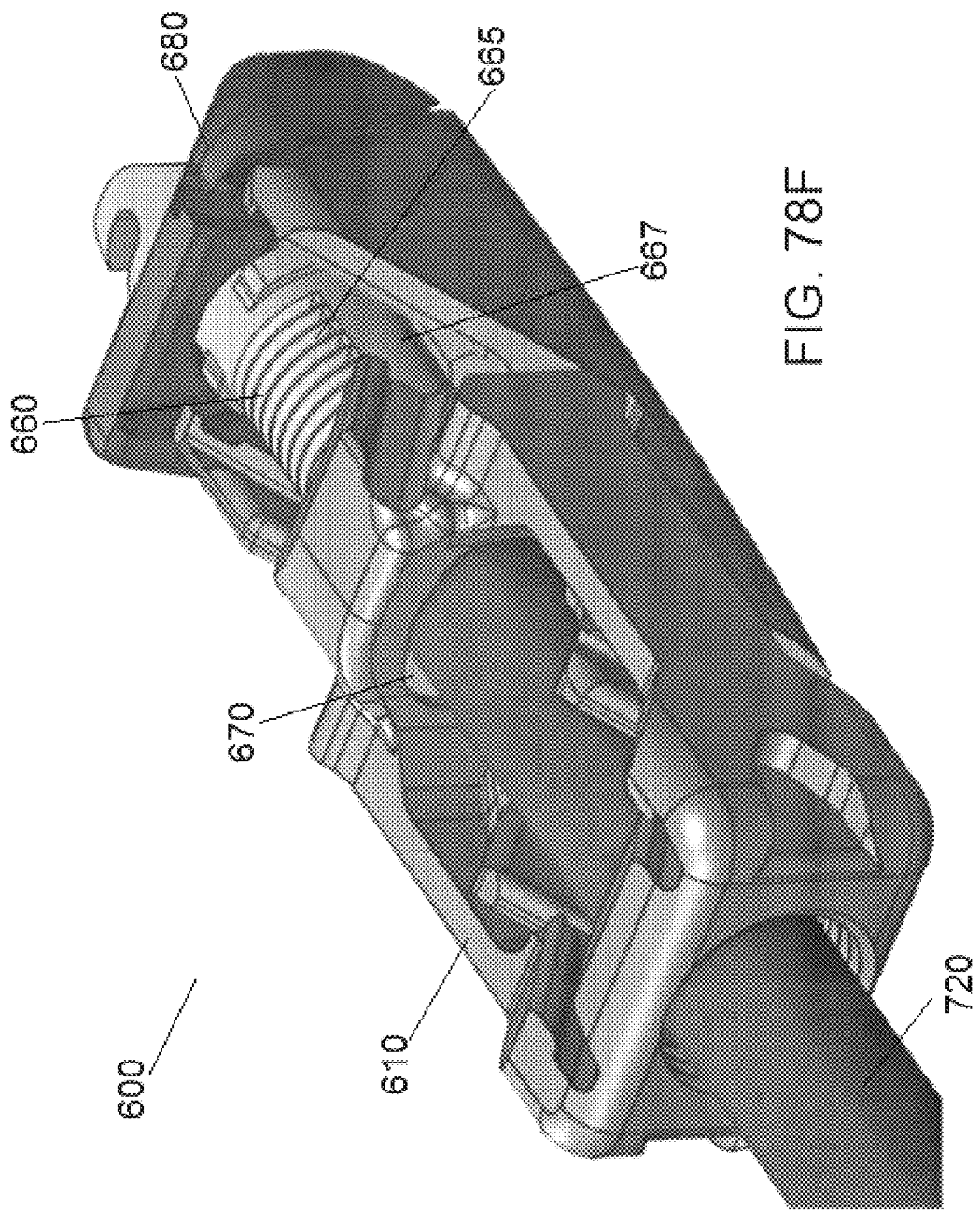

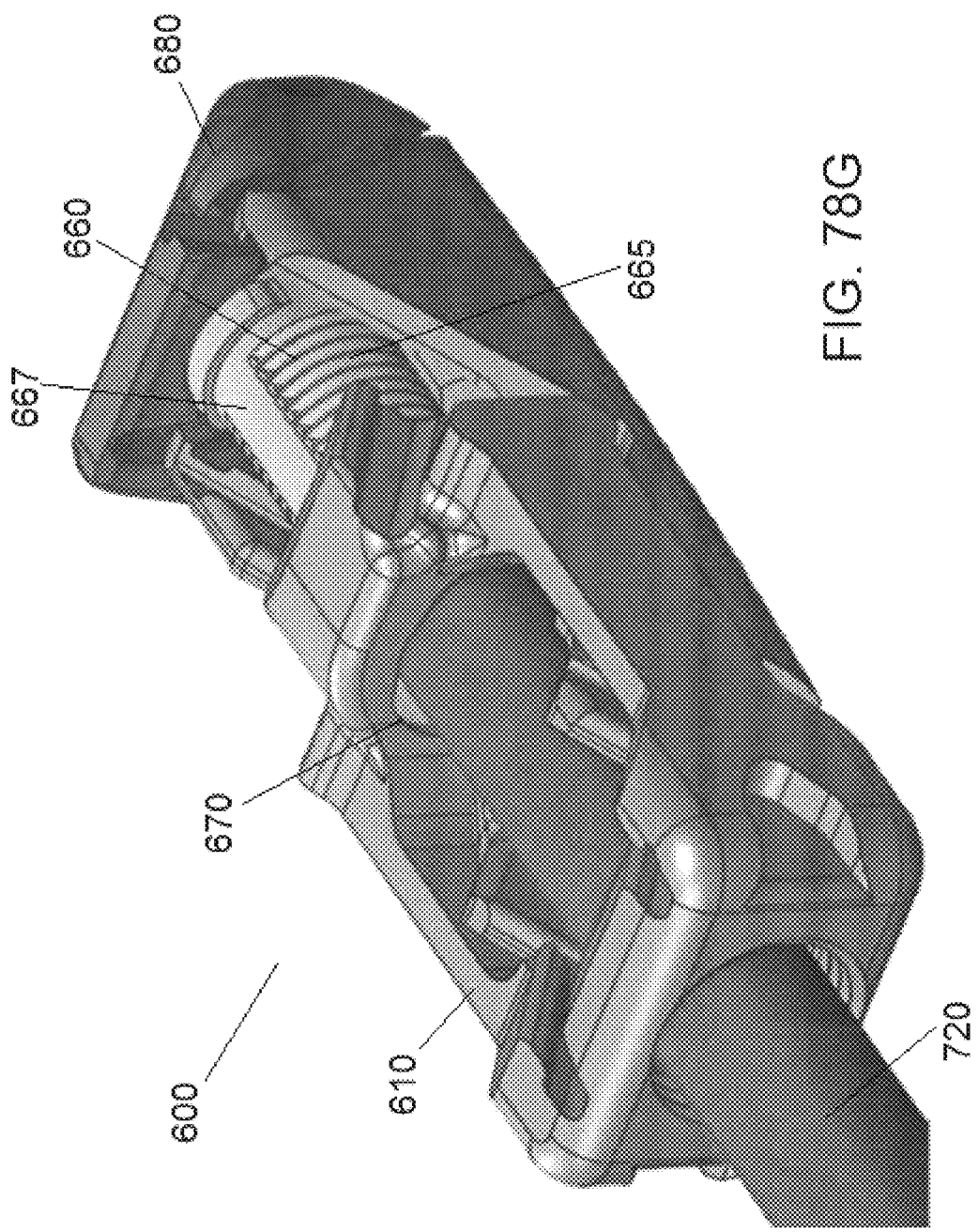

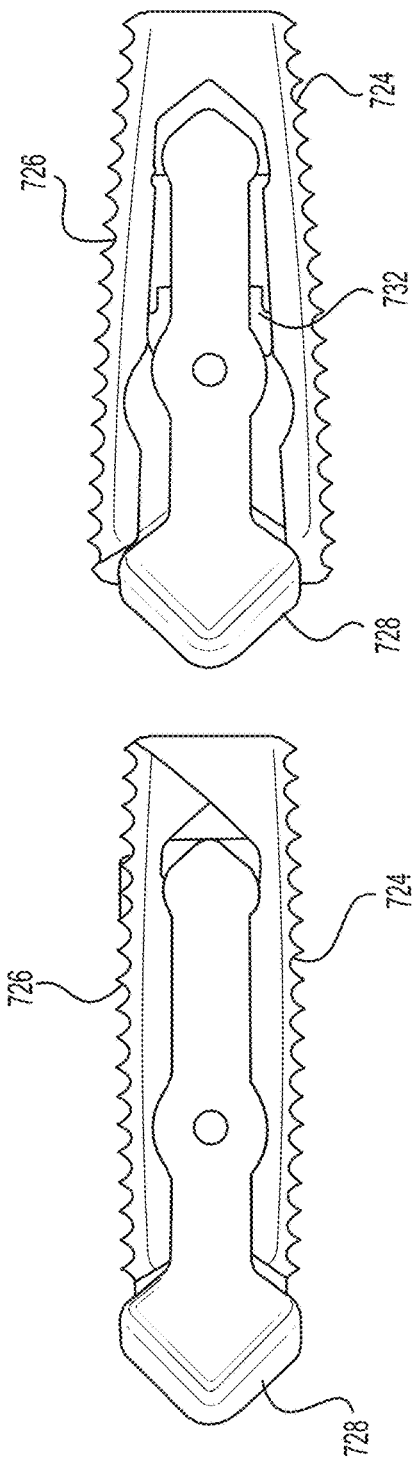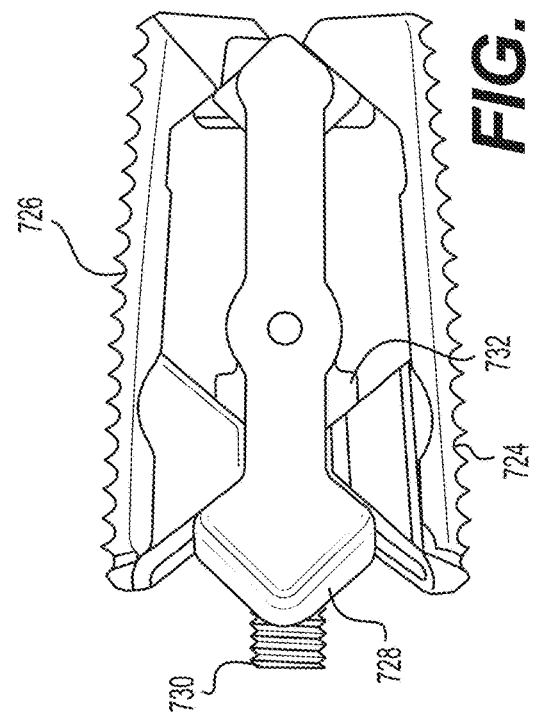

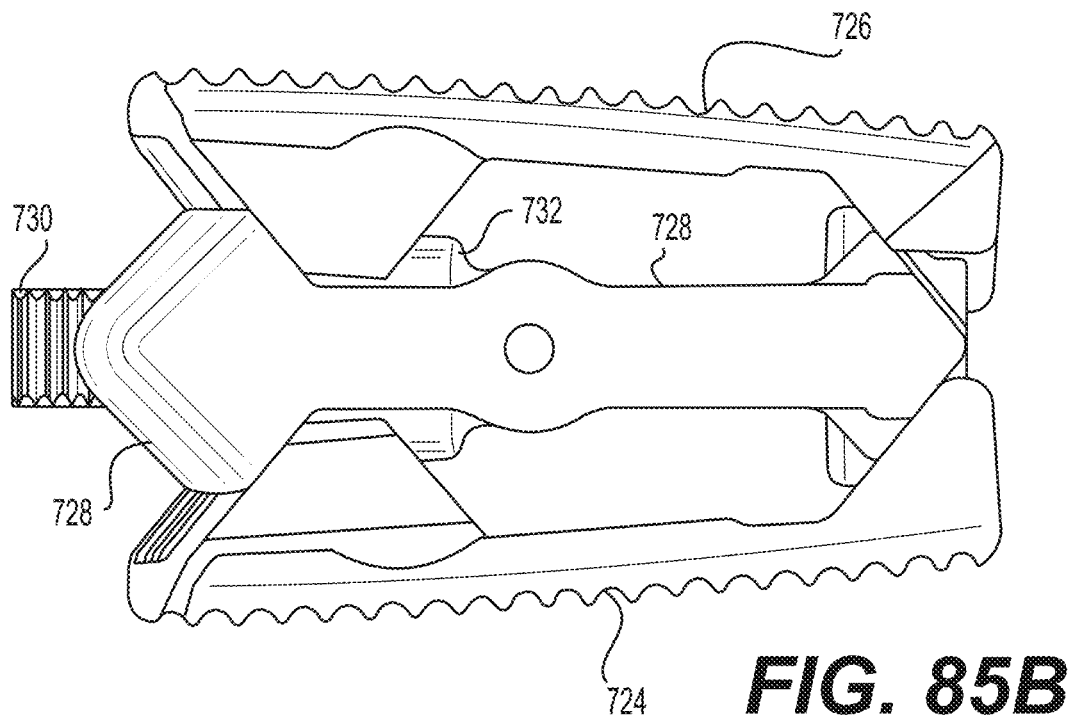
FIG. 85B
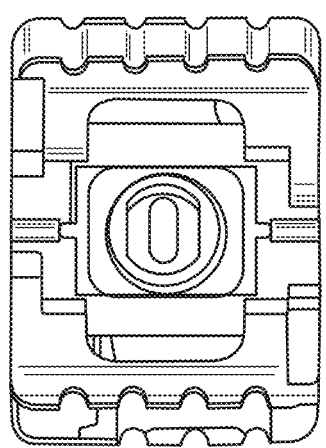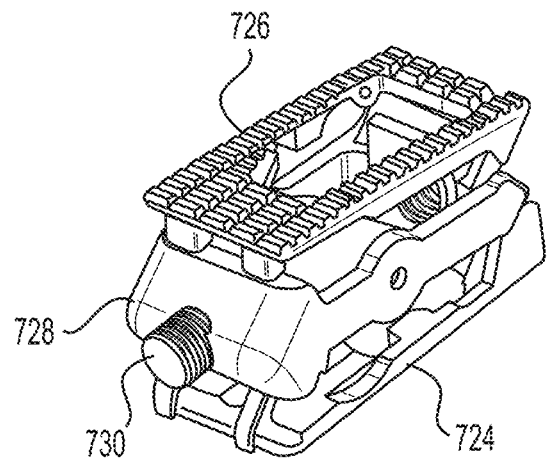
FIG. 85C

EXPANDABLE FUSION DEVICE AND METHOD OF INSTALLATION THEREOF

CROSS-REFERENCE TO RELATED APPLICATIONS

This patent application is a continuation-in-part of U.S. application Ser. No. 15/189,188, filed on Jun. 22, 2016, which is a continuation-in-part of U.S. Ser. No. 15/014,189, filed Feb. 3, 2016, which is a continuation-in-part of U.S. patent Ser. No. 14/109,429 filed on Dec. 17, 2013, which is a divisional application of U.S. patent application Ser. No. 12/875,818 filed on Sep. 3, 2010, now U.S. Pat. No. 8,632,595, the entire disclosures of which are incorporated by reference herein.

BACKGROUND

A common procedure for handling pain associated with intervertebral discs that have become degenerated due to various factors such as trauma or aging is the use of intervertebral fusion devices for fusing one or more adjacent vertebral bodies. Generally, to fuse the adjacent vertebral bodies, the intervertebral disc is first partially or fully removed. An intervertebral fusion device is then typically inserted between neighboring vertebrae to maintain normal disc spacing and restore spinal stability, thereby facilitating an intervertebral fusion.

There are a number of known conventional fusion devices and methodologies in the art for accomplishing the intervertebral fusion. These include screw and rod arrangements, solid bone implants, and fusion devices which include a cage or other implant mechanism which, typically, is packed with bone and/or bone growth inducing substances. These devices are implanted between adjacent vertebral bodies in order to fuse the vertebral bodies together, alleviating the associated pain.

However, there are drawbacks associated with the known conventional fusion devices and methodologies. For example, present methods for installing a conventional fusion device often require that the adjacent vertebral bodies be distracted to restore a diseased disc space to its normal or healthy height prior to implantation of the fusion device. In order to maintain this height once the fusion device is inserted, the fusion device is usually dimensioned larger in height than the initial distraction height. This difference in height can make it difficult for a surgeon to install the fusion device in the distracted intervertebral space.

As such, there exists a need for a fusion device capable of being installed inside an intervertebral disc space at a minimum to no distraction height and for a fusion device that can maintain a normal distance between adjacent vertebral bodies when implanted.

SUMMARY

In an exemplary embodiment, the present invention provides an expandable fusion device capable of being installed inside an intervertebral disc space to maintain normal disc spacing and restore spinal stability, thereby facilitating an intervertebral fusion. In one embodiment, the fusion device includes a central ramp, a first endplate, and a second endplate. The central ramp may be capable of moving in a first direction to push the first and second endplates outwardly and into an unexpanded configuration. The expandable fusion device may be capable of being placed into the disc space down an endoscopic tube and then expanded into an expanded configuration.

In an exemplary embodiment, an apparatus may be provided comprising: a first endplate for an intervertebral implant, wherein the first endplate may comprise a first plate portion having a first upper surface and a first lower surface, wherein the first endplate further comprises first front ramped portions extending away from the first lower surface and first rear ramped portions extending away from first lower surface. The apparatus may further comprise a second endplate for an intervertebral implant, wherein the second endplate may comprise a second plate portion having a second upper surface and a second lower surface, wherein the second endplate further comprises second front ramped portions extending away from the second lower surface and second rear ramped portions extending away from second lower surface. The apparatus may further comprise a body positioned between the first endplate and the second endplate, wherein the body may comprise rear endplate engaging ramps. The apparatus may further comprise a driving ramp positioned at a front end of the apparatus, wherein the driving ramp comprises front endplate engaging ramps. When the apparatus is in an unexpanded configuration, the rear endplate engaging ramps and the front endplate engaging ramps may have ramp angles with respect to a longitudinal axis of the apparatus that differ from ramp angles of the first rear ramped portions and first front ramped portions of the first endplate with respect to the longitudinal axis. The apparatus may be configured such that movement of the driving ramp in one direction causes the first and second endplates to move apart and a movement of the driving ramp in a second direction causes the first and second endplates to move towards one another.

Further areas of applicability of the present invention will become apparent from the detailed description provided hereinafter. It should be understood that the detailed description and specific examples, while indicating the preferred or exemplary embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIGS. 47-49 are perspective views of the driving ramp of the expandable fusion device of FIG. 40 in accordance with one embodiment of the present invention;

FIGS. 70A-70C are different views of the expandable fusion device of FIG. 68 in a contracted state in accordance with some embodiments.

FIGS. 71A-71C are different views of the expandable fusion device of FIG. 68 in a tipped state without full expansion in accordance with some embodiments.

FIGS. 78A-78G are top perspective views of the expandable fusion device of FIG. 68 transitioning from a locked configuration to a disengaged configuration in accordance with some embodiments.

FIGS. 82A-82C are side views of the expandable fusion device of FIG. 79 in the process of expansion in accordance with some embodiments.

FIGS. 85A-85C are different views of the expandable fusion device of FIG. 79 in a fully expanded state according to one embodiment of the present invention.

DETAILED DESCRIPTION

Figure 1:
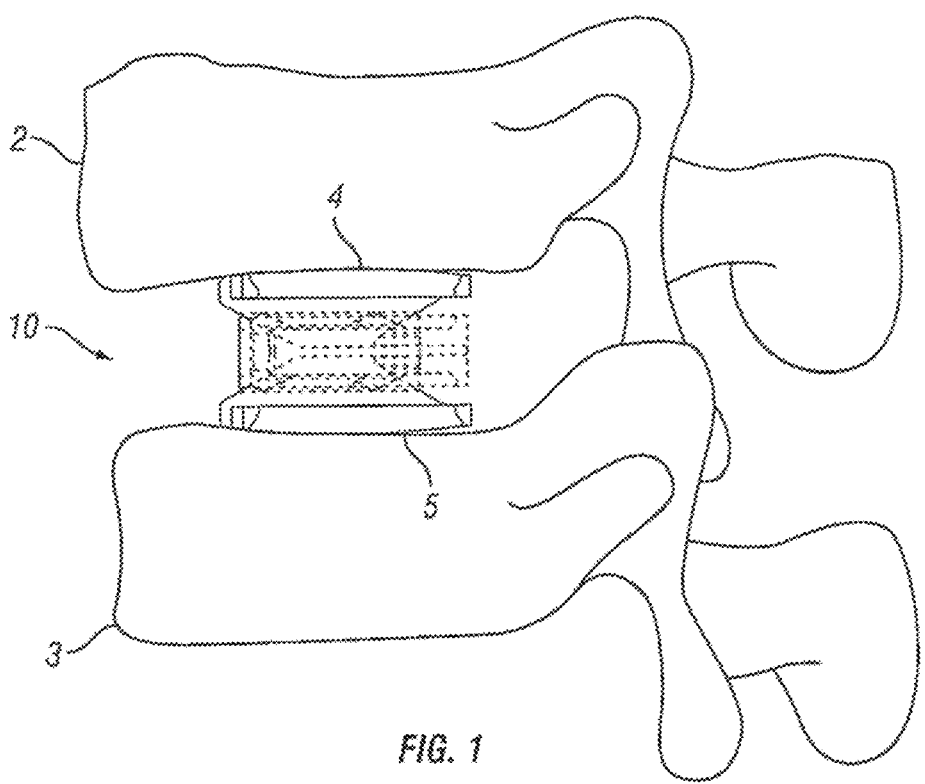
FIG. 1 is a side view of an embodiment of an expandable fusion device shown between adjacent vertebrae according to the present invention.
Figure 2:
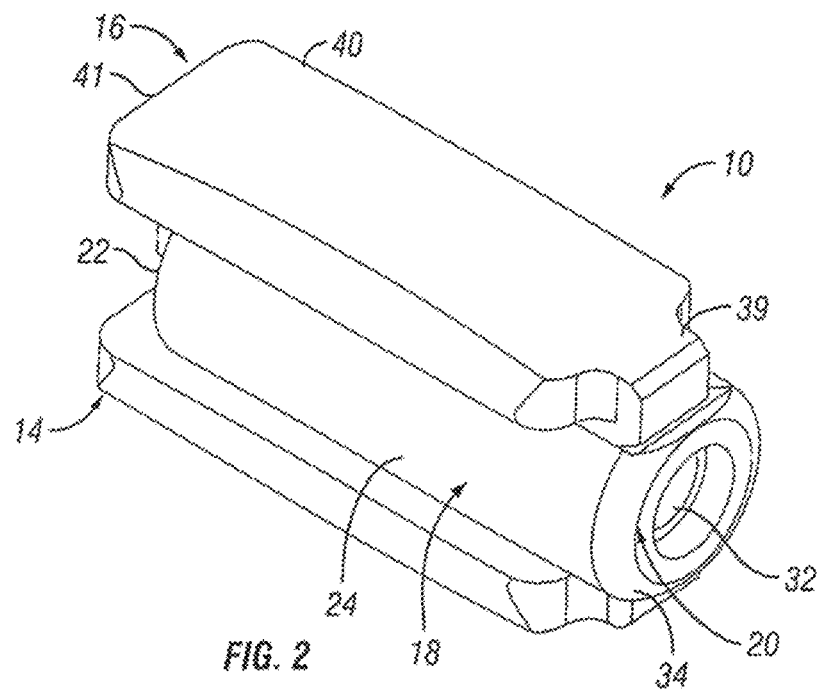
FIG. 2 is a front perspective view of the expandable fusion device of FIG. 1 shown in an unexpanded position in accordance with one embodiment of the present invention.
Figure 3:
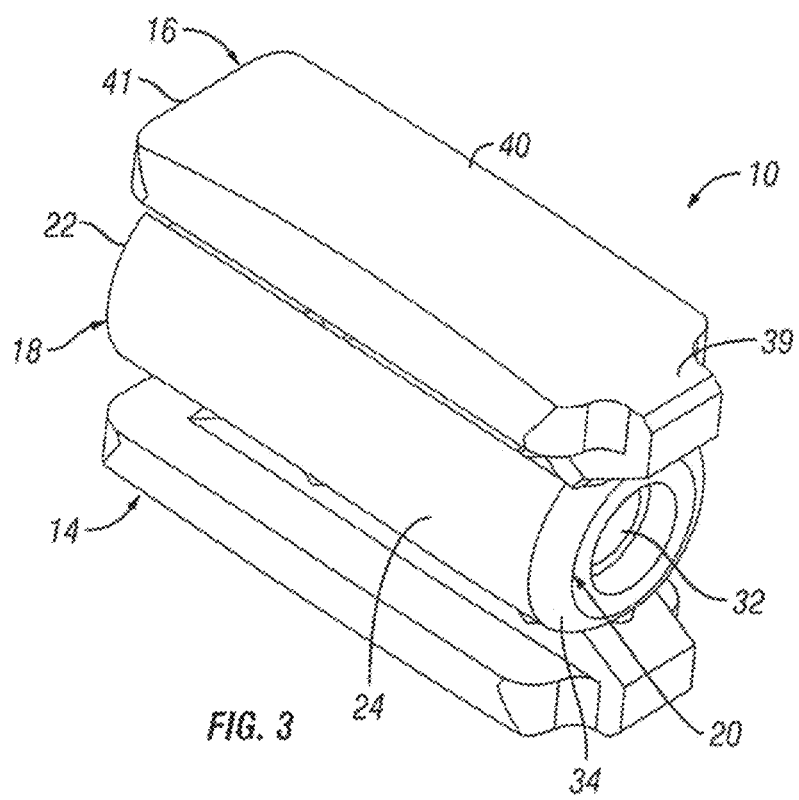
FIG. 3 is a front perspective view of the expandable fusion device of FIG. 1 shown in an expanded position in accordance with one embodiment of the present invention.
Figure 4:
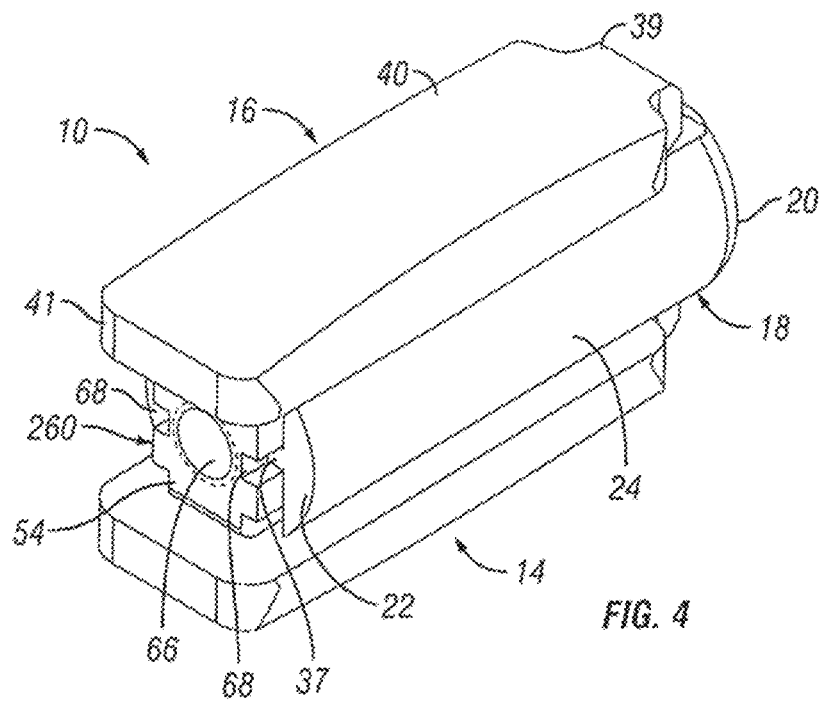
FIG. 4 is a rear perspective view of the expandable fusion device of FIG. 1 shown in an unexpanded position in accordance with one embodiment of the present invention.
Figure 5:
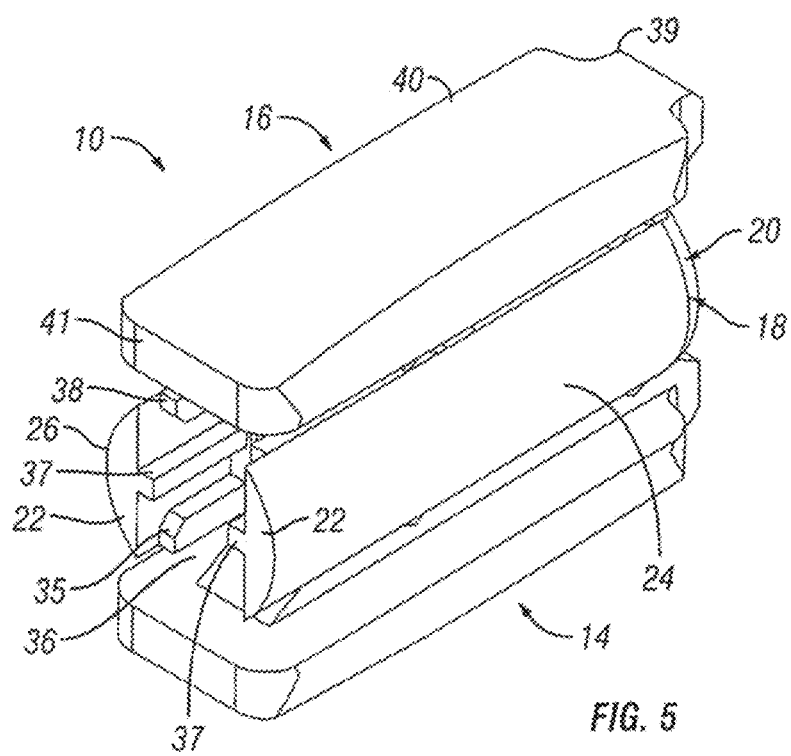
FIG. 5 is a rear perspective view of the expandable fusion device of FIG. 1 shown in an expanded position in accordance with one embodiment of the present invention.
Figure 6:
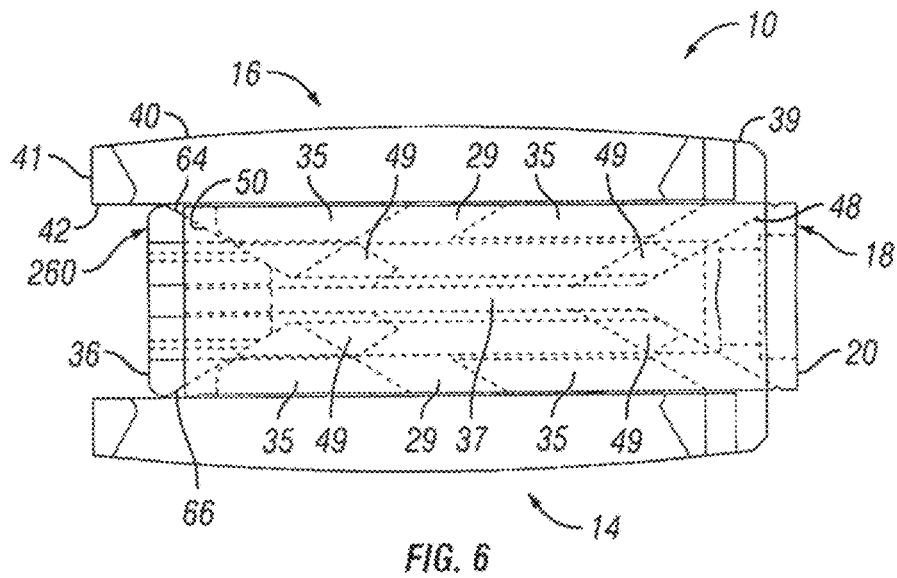
FIG. 6 is a side view of the expandable fusion device of FIG. 1 shown in an unexpanded position in accordance with one embodiment of the present invention.

The following description of the preferred embodiment(s) is merely exemplary in nature and is in no way intended to limit the invention, its application, or uses.

A spinal fusion is typically employed to eliminate pain caused by the motion of degenerated disk material. Upon successful fusion, a fusion device becomes permanently fixed within the intervertebral disc space. Looking at FIG. 1, an exemplary embodiment of an expandable fusion device 10 is shown between adjacent vertebral bodies 2 and 3. The fusion device 10 engages the endplates 4 and 5 of the adjacent vertebral bodies 2 and 3 and, in the installed position, maintains normal intervertebral disc spacing and restores spinal stability, thereby facilitating an intervertebral fusion. The expandable fusion device 10 can be manufactured from a number of materials including titanium, stainless steel, titanium alloys, non-titanium metallic alloys, polymeric materials, plastics, plastic composites, PEEK, ceramic, and elastic materials. In an embodiment, the expandable fusion device 10 can be configured to be placed down an endoscopic tube and into the disc space between the adjacent vertebral bodies 2 and 3.

In an exemplary embodiment, bone graft or similar bone growth inducing material can be introduced around and within the fusion device 10 to further promote and facilitate the intervertebral fusion. The fusion device 10, in one embodiment, is preferably packed with bone graft or similar bone growth inducing material to promote the growth of bone through and around the fusion device. Such bone graft may be packed between the endplates of the adjacent vertebral bodies prior to, subsequent to, or during implantation of the fusion device.

With reference to FIGS. 2-7, an embodiment of the fusion device 10 is shown. In an exemplary embodiment, the fusion device 10 includes a first endplate 14, a second endplate 16, a central ramp 18, and a driving ramp 260. In an embodiment, the expandable fusion device 10 can be configured to be placed down an endoscopic tube and into the disc space between the adjacent vertebral bodies 2 and 3. One or more components of the fusion device 10 may contain features, such as through bores, that facilitate placement down an endoscopic tube. In an embodiment, components of the fusion device 10 are placed down the endoscopic tube with assembly of the fusion device 10 in the disc space.

Although the following discussion relates to the second endplate 16, it should be understood that it also equally applies to the first endplate 14 as the second endplate 16 is substantially identical to the first endplate 14 in embodiments of the present invention. Turning now to FIGS. 2-7 and 10, in an exemplary embodiment, the second endplate 16 has a first end 39 and a second end 41. In the illustrated embodiment, the second endplate 16 further comprise an upper surface 40 connecting the first end 39 and the second end 41, and a lower surface 42 connecting the first end 39 and the second end 41. In an embodiment, the second endplate 16 further comprises a through opening 44, as seen on FIG. 11. The through opening 44, in an exemplary embodiment, is sized to receive bone graft or similar bone growth inducing material and further allow the bone graft or similar bone growth inducing material to be packed in the central opening in the central ramp 18.

Figure 7:
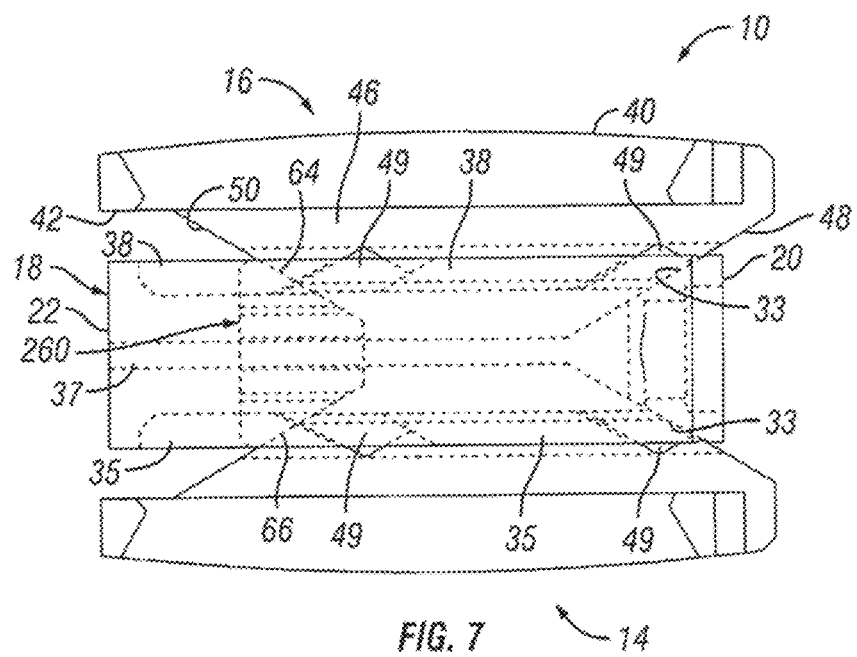
FIG. 7 is a side view of the expandable fusion device of FIG. 1 shown in an expanded position in accordance with one embodiment of the present invention.
Figure 10:
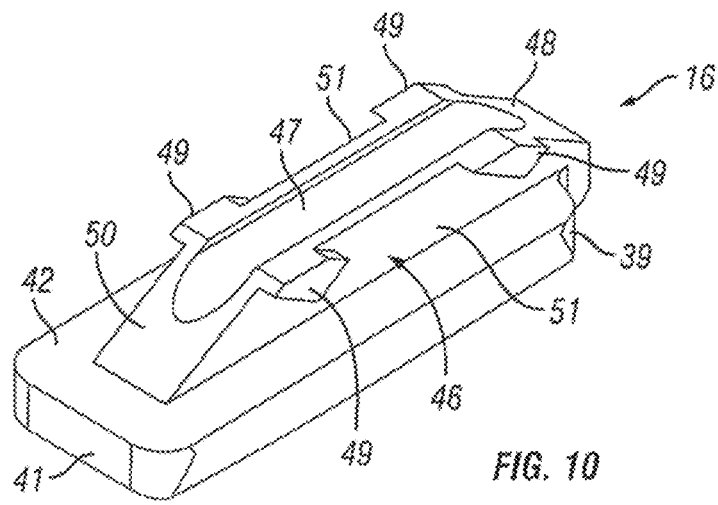
FIG. 10 is a perspective of an endplate of the expandable fusion device of FIG. 1 in accordance with one embodiment of the present invention.

As best seen in FIGS. 7 and 10, the lower surface 42 includes at least one extension 46 extending along at least a portion of the lower surface 42, in an embodiment. In an exemplary embodiment, the extension 46 can extend along a substantial portion of the lower surface 42, including, along the center of the lower surface 42. In the illustrated embodiment, the extension 46 includes a generally concave surface 47. The concave surface 47 can form a through bore with the corresponding concave surface 47 (not illustrated) of the first endplate 14, for example, when the device 10 is in an unexpanded configuration. In another exemplary embodiment, the extension 46 includes at least one ramped surface 48. In another exemplary embodiment, there are two ramped surfaces 48, 50 with the first ramped surface 48 facing the first end 39 and the second ramped surface facing the second end 41. In an embodiment, the first ramped surface 48 can be proximate the first end 39, and the second ramped surface 50 can be proximate the second end 41. It is contemplated that the slope of the ramped surfaces 48, 50 can be equal or can differ from each other. The effect of varying the slopes of the ramped surfaces 48, 50 is discussed below.

In one embodiment, the extension 46 can include features for securing the endplate 16 when the expandable fusion device 10 is in an expanded position. In an embodiment, the extension 46 includes one or more protuberances 49 extending from the lateral sides 51 of the extension. In the illustrated embodiment, there are two protuberances 49 extending from each of the lateral sides 51 with each of the sides 53 having one of the protuberances 49 extending from a lower portion of either end. As will be discussed in more detail below, the protuberances 49 can be figured to engage the central ramp 18 preventing and/or restricting longitudinal movement of the endplate 16 when the device 10 is in an expanded position.

Figure 15:
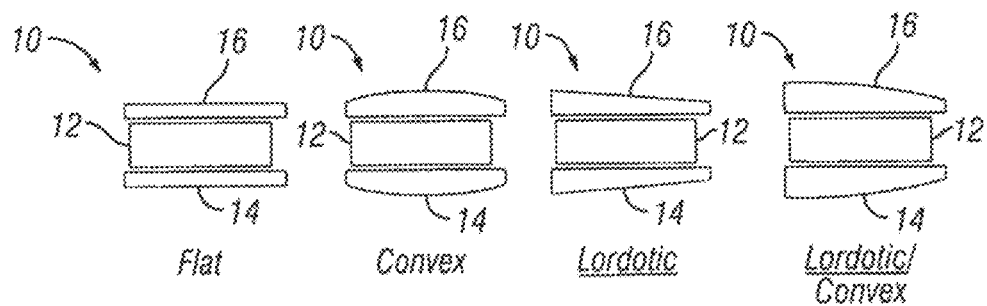
FIG. 15 is a side schematic view of the expandable fusion device of FIG. 1 having different endplates.

As illustrated in FIGS. 2-5, in one embodiment, the upper surface 40 of the second endplate 16 is flat and generally planar to allow the upper surface 40 of the endplate 16 to engage with the adjacent vertebral body 2. Alternatively, as shown in FIG. 15, the upper surface 40 can be curved convexly or concavely to allow for a greater or lesser degree of engagement with the adjacent vertebral body 2. It is also contemplated that the upper surface 40 can be generally planar but includes a generally straight ramped surface or a curved ramped surface. The ramped surface allows for engagement with the adjacent vertebral body 2 in a lordotic fashion. While not illustrated, in an exemplary embodiment, the upper surface 40 includes texturing to aid in gripping the adjacent vertebral bodies. Although not limited to the following, the texturing can include teeth, ridges, friction increasing elements, keels, or gripping or purchasing projections.

Referring now to FIGS. 2-8, in an exemplary embodiment, the central ramp 18 has a first end 20, a second end 22, a first side portion 24 connecting the first end 20 and the second end 22, and a second side portion 26 (best seen on FIG. 5) on the opposing side of the central ramp 12 connecting the first end 20 and the second end 22. The first side portion 24 and the second side portion 26 may be curved, in an exemplary embodiment. The central ramp 18 further includes a lower end 28, which is sized to receive at least a portion of the first endplate 14, and an upper end 30, which is sized to receive at least a portion of the second endplate 16.

The first end 20 of the central ramp 18, in an exemplary embodiment, includes an opening 32. The opening 32 can be configured to receive an endoscopic tube in accordance with one or more embodiments. The first end 20 of the central ramp 18, in an exemplary embodiment, includes at least one angled surface 33, but can include multiple angled surfaces. The angled surface 33 can serve to distract the adjacent vertebral bodies when the fusion device 10 is inserted into an intervertebral space.

The second end 22 of the central ramp 18, in an exemplary embodiment, includes an opening 36. The opening 36 extends from the second end 22 of the central ramp 18 into a central guide 37 in the central ramp 18.

Figure 8:
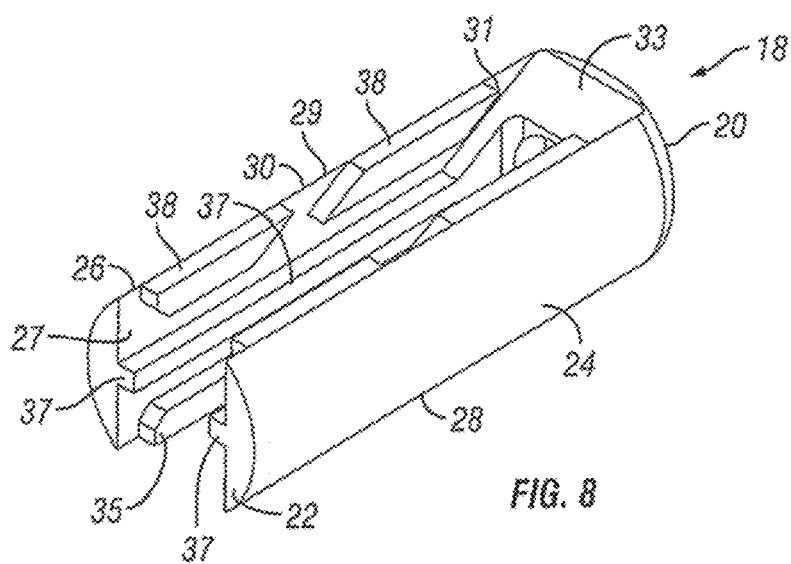
FIG. 8 is a perspective view of the central ramp of the expandable fusion device of FIG. 1 in accordance with one embodiment of the present invention.
Figure 9:
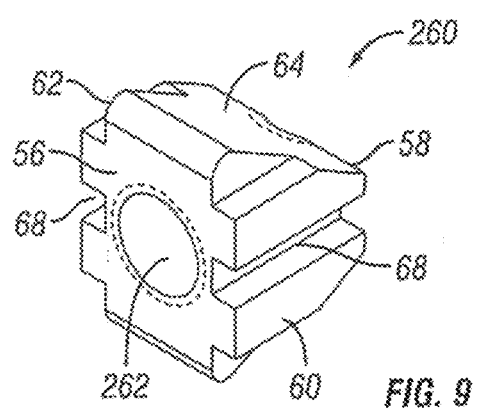
FIG. 9 is a perspective view of the driving ramp of the expandable fusion device of FIG. 1 in accordance with one embodiment of the present invention.

In an embodiment, the central ramp 18 further includes one or more ramped surfaces 33. As best seen in FIG. 8, the one or more ramped surfaces 33 positioned between the first side portion 24 and the second side portion 26 and between the central guide 37 and the second end 22. In an embodiment, the one or more ramped surfaces 33 face the second end 22 of the central ramp 18. In one embodiment, the central ramp 18 includes two ramped surfaces 33 with one of the ramped surfaces 33 being sloped upwardly and the other of the ramped surfaces 33 being sloped downwardly. The ramped surfaces 33 of the central ramp can be configured and dimensioned to engage the ramped surface 48 in each of the first and second endplates 14, 16.

Although the following discussion relates to the second side portion 26 of the central ramp 18, it should be understood that it also equally applies to the first side portion 24 in embodiments of the present invention. In the illustrated embodiment, the second side portion 26 includes an inner surface 27. In an embodiment, the second side portion 26 further includes a lower guide 35, a central guide 37, and an upper guide 38. In the illustrated embodiment, the lower guide 35, central guide 37, and the upper guide 38 extend out from the inner surface 27 from the second end 22 to the one or more ramped surfaces 31. In the illustrated embodiment, the second end 22 of the central ramp 18 further includes one or more guides 38. The guides 38 can serve to guide the translational movement of the first and second endplates 14, 16 with respect to the central ramp 18. For example, protuberances 49 on the second endplate 16 may be sized to be received between the central guide 37 and the upper guide 38. Protuberances 49 of the first endplate 16 may be sized to be received between the central guide 37 and the lower guide 35. A first slot 29 may be formed proximate the middle of the upper guide 38. A second slot 31 may be formed between end of the upper guide 38 and the one or more ramped surfaces 33. The protuberances 49 may be sized to be received within the first slot 29 and/or the second slot 31 when the device 10 is in the expanded position.

Referring now to FIGS. 4-7 and 9, the driving ramp 260 has a through bore 262. In an embodiment, the driving ramp 260 is generally wedge-shaped. As illustrated, the driving ramp 260 may comprise a wide end 56, a narrow end 58, a first side portion 60 connecting the wide end 56 and the narrow end 58, and a second side portion 62 connecting the wide end 56 and the narrow end 58. The driving ramp 260 further may comprise ramped surfaces, including an upper ramped surface 64 and an opposing lower ramped surface 66. The upper ramped surface 64 and the lower ramped surface 66 may be configured and dimensioned to engage the ramped surface 50 proximate the second end 41 in of the first and the second endplates 14, 16. The first and second side portions 60, 62 may each include grooves 68 that extend, for example, in a direction parallel to the longitudinal axis of the through bore 262. The grooves 68 may be sized to receive the central guide 37 on the interior surface 27 of each of the side portions 24, 26 of the central ramp 18. In this manner, the grooves 68 together with the central guide 37 can surface to guide the translational movement of the driving ramp 260 in the central ramp 18.

A method of installing the expandable fusion device 10 of FIG. 1 is now discussed in accordance with one embodiment of the present invention. Prior to insertion of the fusion device 10, the intervertebral space is prepared. In one method of installation, a discectomy is performed where the intervertebral disc, in its entirety, is removed. Alternatively, only a portion of the intervertebral disc can be removed. The endplates of the adjacent vertebral bodies 2, 3 are then scraped to create an exposed end surface for facilitating bone growth across the intervertebral space. One or more endoscopic tubes can then be inserted into the disc space. The expandable fusion device 10 can then be introduced into the intervertebral space down an endoscopic tube and seated in an appropriate position in the intervertebral disc space.

After the fusion device 10 has been inserted into the appropriate position in the intervertebral disc space, the fusion device 10 can then be expanded into the expanded position. To expand the fusion device 10, the driving ramp 260 may move in a first direction with respect to the central ramp 18. Translational movement of the driving ramp 260 through the central ramp 18 may be guided by the central guide 37 on each of the first and second side portions 24, 26 of the central ramp 18. As the driving ramp 260 moves, the upper ramped surface 64 pushes against the ramped surface 50 proximate the second end 41 of the second endplate 16, and the lower ramped surface 66 pushes against the ramped surface 50 proximate the second end 41 of the first endplate 14. In addition, the ramped surfaces 33 in the central ramp 18 push against the ramped surface 48 proximate the first end 41 of the first and second endplates 14, 16. In this manner, the first and second endplates 14, 16 are pushed outwardly into an expanded configuration. As discussed above, the central ramp 16 includes locking features for securing the endplates 14, 16.

Figure 16:
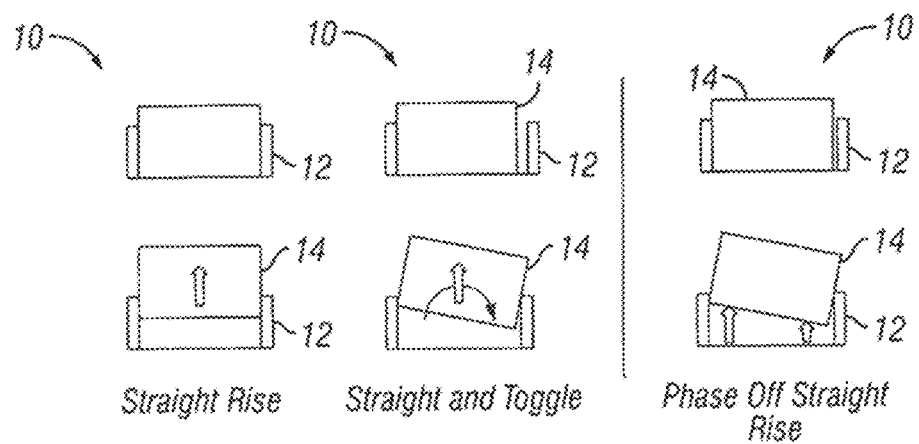
FIG. 16 is a partial side schematic view of the expandable fusion device of FIG. 1 showing different modes of endplate expansion.

It should also be noted that the expansion of the endplates 14, 16 can be varied based on the differences in the dimensions of the ramped surfaces 48, 50 and the angled surfaces 62, 64. As best seen in FIG. 16, the endplates 14, 16 can be expanded in any of the following ways: straight rise expansion, straight rise expansion followed by a toggle into a lordotic expanded configuration, or a phase off straight rise into a lordotic expanded configuration.

Turning back to FIGS. 2-7, in the event the fusion device 10 needs to be repositioned or revised after being installed and expanded, the fusion device 10 can be contracted back to the unexpanded configuration, repositioned, and expanded again once the desired positioning is achieved. To contract the fusion device 10, the central ramp 18 is moved with respect to the central ramp 260 away from the central ramp 260. As the central ramp 18 moves, the ramped surfaces 33 in the central ramp 18 ride along the ramped surfaces 48 of the first and second endplates 14, 16 with the endplates 14, 16 moving inwardly into the unexpanded position.

Figure 17:
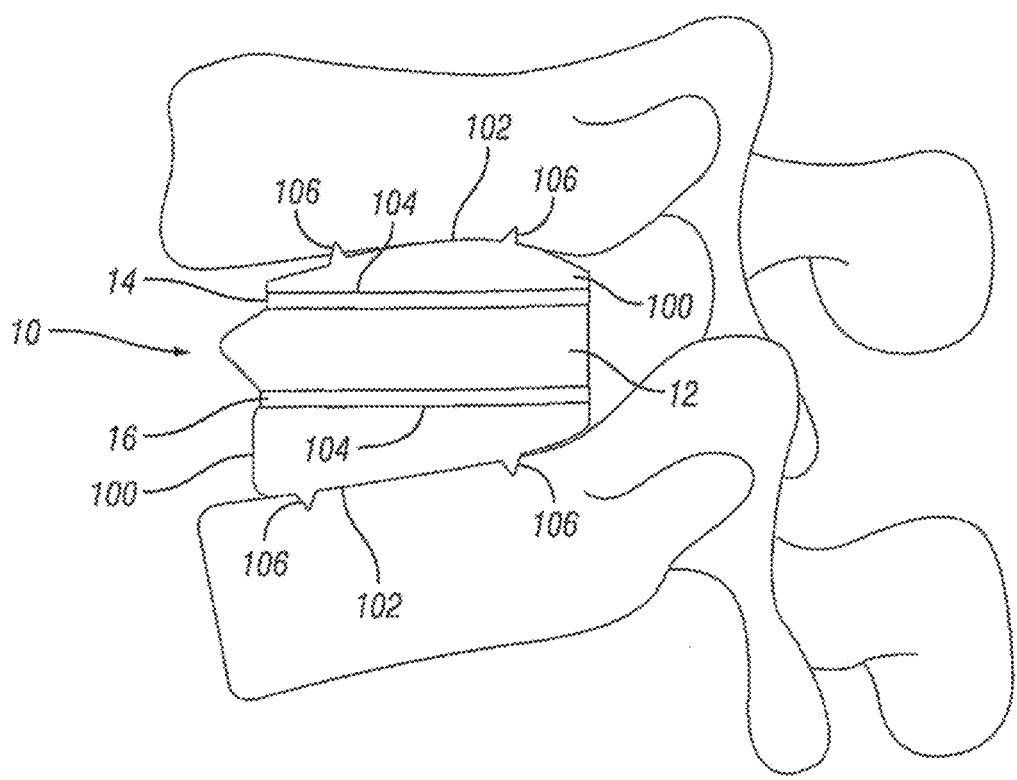
FIG. 17 is a side schematic view of the expandable fusion device of FIG. 1 with artificial endplates shown between adjacent vertebrae.
Figure 18:
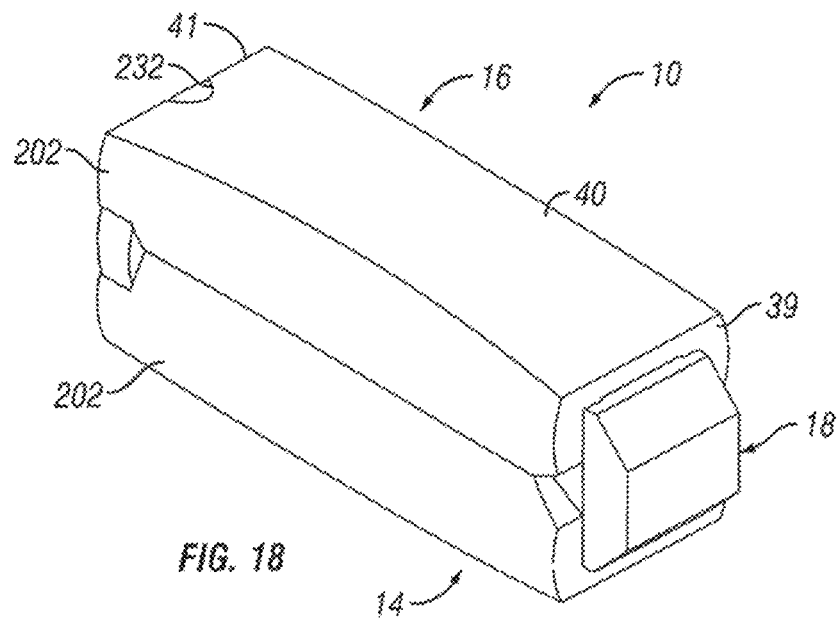
FIG. 18 is a front perspective view of an alternative embodiment of an expandable fusion device shown in an unexpanded position in accordance with one embodiment of the present invention.

With reference now to FIG. 17, fusion device 10 is shown with an exemplary embodiment of artificial endplates 100. Artificial endplates 100 allows the introduction of lordosis even when the endplates 14 and 16 of the fusion device 10 are generally planar. In one embodiment, the artificial endplates 100 have an upper surface 102 and a lower surface 104. The upper surfaces 102 of the artificial endplates 100 have at least one spike 106 to engage the adjacent vertebral bodies. The lower surfaces 104 have complementary texturing or engagement features on their surfaces to engage with the texturing or engagement features on the upper endplate 14 and the lower endplate 16 of the fusion device 10. In an exemplary embodiment, the upper surface 102 of the artificial endplates 100 have a generally convex profile and the lower surfaces 104 have a generally parallel profile to achieve lordosis. In another exemplary embodiment, fusion device 10 can be used with only one artificial endplate 100 to introduce lordosis even when the endplates 14 and 16 of the fusion device 10 are generally planar. The artificial endplate 100 can either engage endplate 14 or engage endplate 16 and function in the same manner as described above with respect to two artificial endplates 100.

Figure 11:
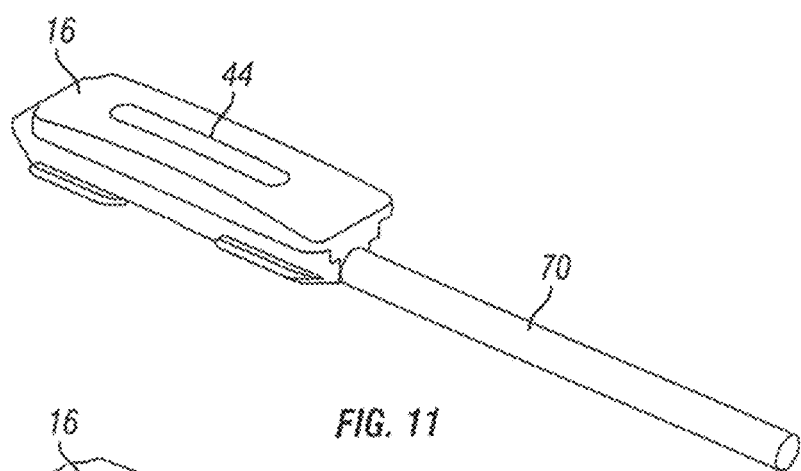
FIG. 11 a perspective view showing placement of the first endplate of an embodiment of an expandable fusion device down an endoscopic tube and into the disc space in accordance with one embodiment of the present invention.
Figure 12:
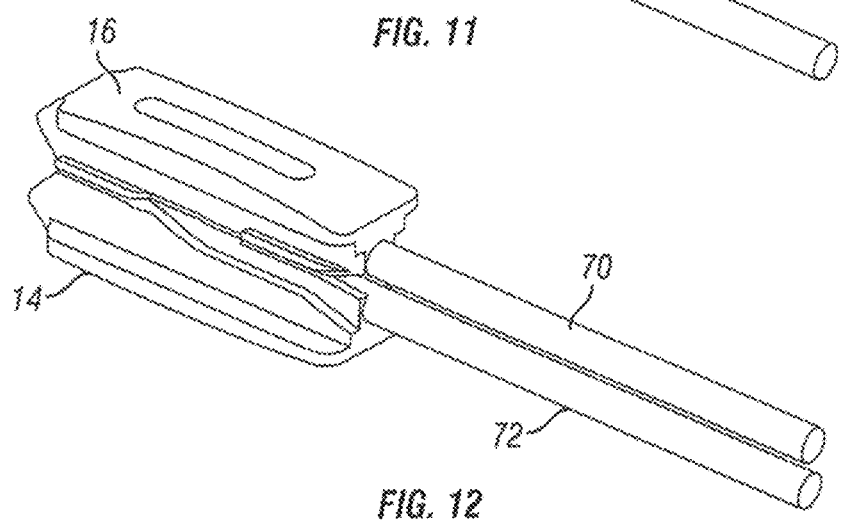
FIG. 12 is a perspective view showing placement of the second endplate of the expandable fusion device down an endoscopic tube and into the disc space in accordance with one embodiment of the present invention.
Figure 13:
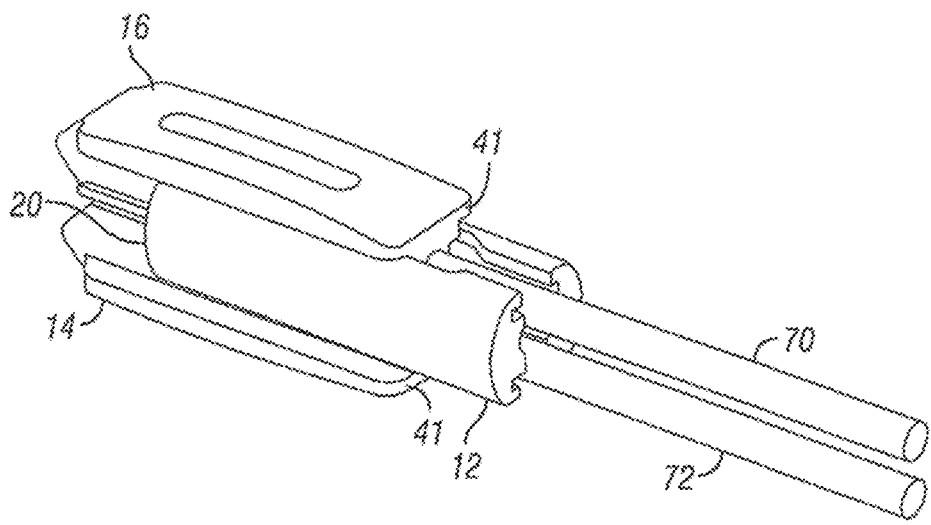
FIG. 13 is a perspective view showing placement of the central ramp of the expandable fusion device down an endoscopic tube and into the disc space in accordance with one embodiment of the present invention.
Figure 14:
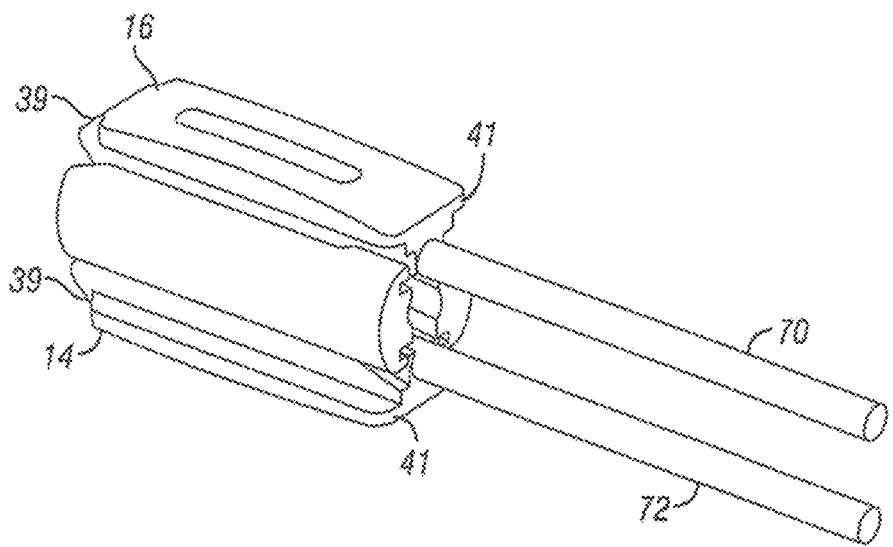
FIG. 14 is a perspective view showing expansion of the expandable fusion device in accordance with one embodiment of the present invention.

With reference to FIGS. 11-14, an embodiment for placing an expandable fusion device 10 into an intervertebral disc space is illustrated. The expandable fusion device 10 can be introduced into the intervertebral space down an endoscopic tube utilizing a tool 70 that is attached to endplate 16, with the second endplate 16 being first placed down the tube with tool 70 and into the disc space, as seen in FIG. 11. After insertion of the second endplate 16, the first endplate 14 can be placed down the same endoscopic tube with tool 72 and into the disc space, as shown on FIG. 12. Following the first endplate 14, the central ramp 12 can be placed down the same endoscopic tube and into the disc space guided by tools 70 and 72, as shown on FIGS. 13 and 14.

Referring now to FIGS. 18-23, an alternative embodiment of the expandable fusion device 10 is shown. In an exemplary embodiment, the fusion device 10 includes a first endplate 14, a second endplate 16, a central ramp 18, and an actuator assembly 200. As will be discussed in more detail below, the actuator assembly 200 drives the central ramp 18 which forces apart the first and second endplates 14, 16 to place the expandable fusion device in an expanded position. One or more components of the fusion device 10 may contain features, such as through bores, that facilitate placement down an endoscopic tube. In an embodiment, components of the fusion device 10 are placed down the endoscopic tube with assembly of the fusion device 10 in the disc space.

Although the following discussion relates to the second endplate 16, it should be understood that it also equally applies to the first endplate 14 as the second endplate 16 is substantially identical to the first endplate 14 in embodiments of the present invention. With additional reference to FIG. 24, in an exemplary embodiment, the second endplate 16 has a first end 39 and a second end 41. In the illustrated embodiment, the second endplate 16 further comprise an upper surface 40 connecting the first end 39 and the second end 41, and a lower surface 42 connecting the first end 39 and the second end 41. While not illustrated, in an embodiment, the second endplate 16 further comprises a through opening. The through opening, in an exemplary embodiment, is sized to receive bone graft or similar bone growth inducing material.

In one embodiment, the upper surface 40 of the second endplate 16 is flat and generally planar to allow the upper surface 40 of the endplate 16 to engage with the adjacent vertebral body 2. Alternatively, as shown in FIG. 15, the upper surface 40 can be curved convexly or concavely to allow for a greater or lesser degree of engagement with the adjacent vertebral body 2. It is also contemplated that the upper surface 40 can be generally planar but includes a generally straight ramped surface or a curved ramped surface. The ramped surface allows for engagement with the adjacent vertebral body 2 in a lordotic fashion. While not illustrated, in an exemplary embodiment, the upper surface 40 includes texturing to aid in gripping the adjacent vertebral bodies. Although not limited to the following, the texturing can include teeth, ridges, friction increasing elements, keels, or gripping or purchasing projections.

In one embodiment, the second endplate 16 further comprises a first side portion 202 connecting the first end 39 and the second end 41, and a second side portion 204 connecting the first end 39 and the second end 41. In the illustrated embodiment, the first and second side portions 202, 204 are extensions from the lower surface 42. In an exemplary embodiment, the first and second side portions 202, 204 each include ramped surfaces 206, 208. In the illustrated embodiment, the ramped surfaces 206, 208 extend from the first end 39 of the second endplate 16 to bottom surfaces 210, 212 of each of the side portions 202, 204. In one embodiment, the ramped surfaces 206, 208 are forward facing in that the ramped surfaces 206, 208 face the first end 39 of the second endplate. As previously discussed, the slope of the ramped surfaces 206, 208 may be varied as desired for a particular application.

Figure 24:
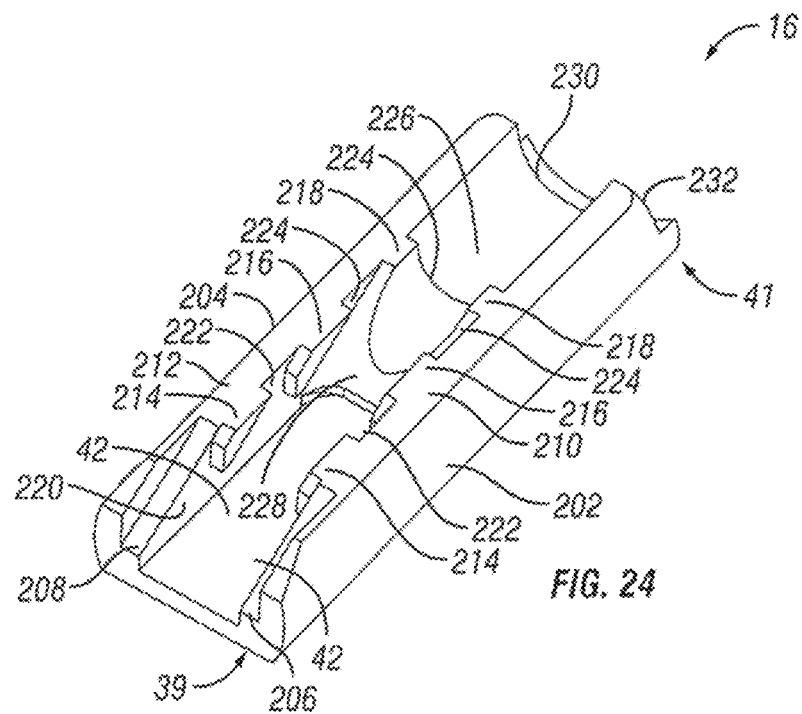
FIG. 24 is a perspective of an endplate of the expandable fusion device of FIG. 18 in accordance with one embodiment of the present invention.

In an embodiment, the first and second side portions 202, 204 each comprise at least one protuberance 214. In an exemplary embodiment, the first and second side portions 202, 204 each comprise a first protuberance 214, a second protuberance 216, and a third protuberance 218. In one embodiment, the protuberances 214, 216, 218 extend from the interior surface 220 of the first and second side portions 202, 204. In an exemplary embodiment, the protuberances 214, 216, 218 extend at the lower side of the interior surface 220. As best seen in FIG. 24, the first and the second protuberances 214, 216 form a first slot 222, and the second and third protuberances 216, 218 form a second slot 224.

As best seen in FIG. 24, the lower surface 42 of the second endplate 16, in an embodiment, includes a central extension 224 extending along at least a portion of the lower surface. In the illustrated embodiment, the central extension 224 extends between the first and second side portions 202 and 204. In an exemplary embodiment, the central extension 224 can extend from the second end 41 of the endplate 16 to the central portion of the endplate. In one embodiment, the central extension 224 includes a generally concave surface 226 configured and dimensioned to form a through bore with the corresponding concave surface 226 (not illustrated) of the first endplate 14. The central extension 224 can further include, in an exemplary embodiment, a ramped surface 228. In the illustrated embodiment, the ramped surface 228 faces the first end 39 of the endplate 16. The ramped surface 228 can be at one end of the central extension 224. In an embodiment, the other end of the central extension 224 forms a stop 230. In the illustrated embodiment, the stop 230 is recessed from the second end 41 of the second endplate 16.

Figure 25:
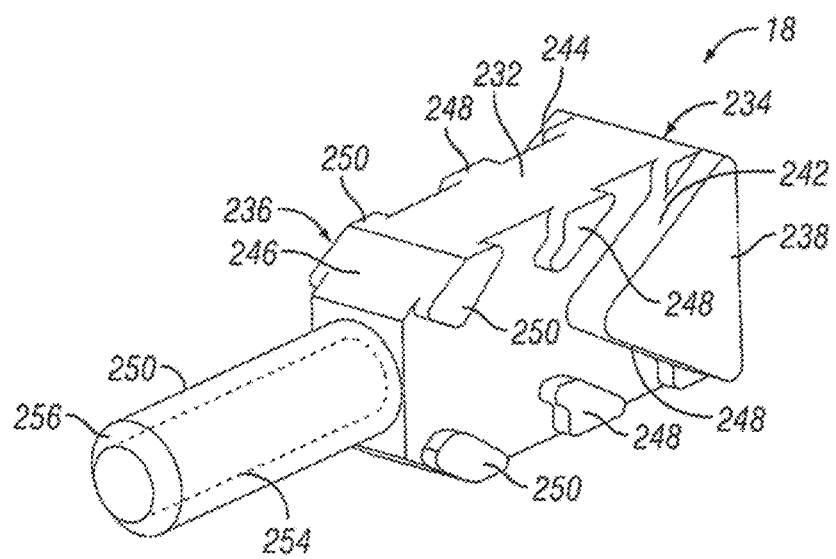
FIG. 25 is a perspective view of the central ramp of the expandable fusion device of FIG. 18 in accordance with one embodiment of the present invention.
Figure 26:
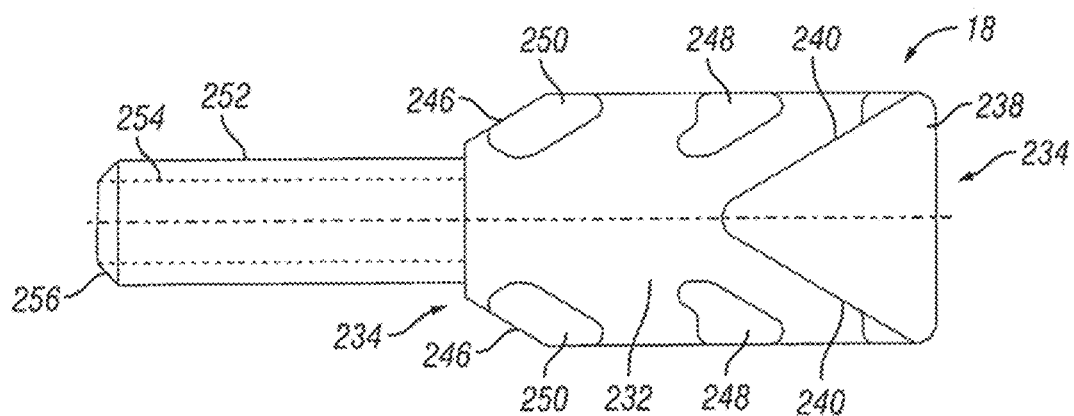
FIG. 26 is a side view of the central ramp of the expandable fusion device of FIG. 18 in accordance with one embodiment of the present invention.
Figure 27:
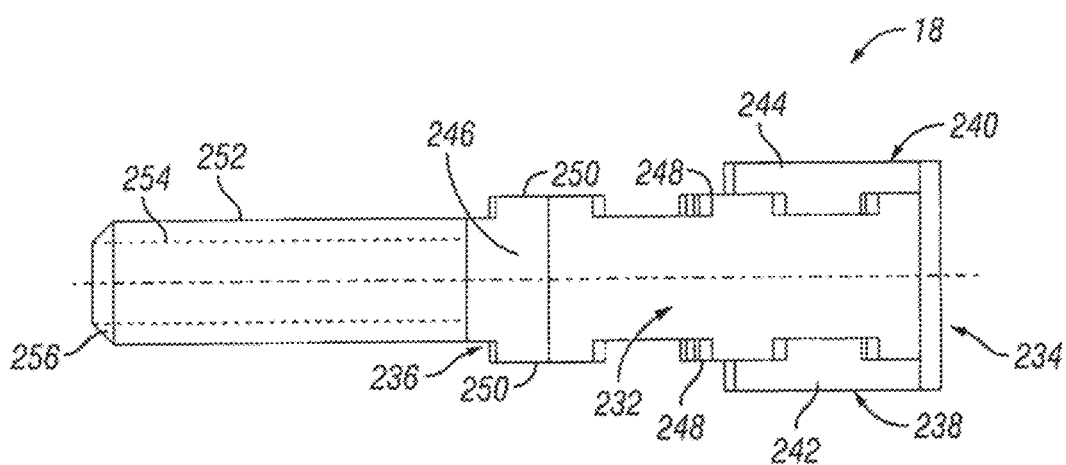
FIG. 27 is a top view of the central ramp of the expandable fusion device of FIG. 18 in accordance with one embodiment of the present invention.

Referring to FIGS. 25-27, in an exemplary embodiment, the central ramp 18 includes a body portion 232 having a first end 234 and a second end 236. In an embodiment, the body portion 232 includes at least a first expansion portion 238. In an exemplary embodiment, the body portion 232 includes a first expansion portion 238 and a second expansion portion 240 extending from opposing sides of the body portion with each of the first and second expansion portions 238, 240 having a generally triangular cross-section. In one embodiment, the expansion portions 238, 240 each have angled surfaces 242, 244 configured and dimensioned to engage the ramped surfaces 206, 208 of the first and second endplates 14, 16 and force apart the first and second endplates 14, 16. In an embodiment, the engagement between the angled surfaces 242, 244 of the expansion portions 238, 240 with the ramped surfaces 206, 208 of the first and second endplates 14, 16 may be described as a dovetail connection.

The second end 236 of the central ramp 18, in an exemplary embodiment, includes opposing angled surfaces 246. The angled surfaces 246 can be configured and dimensioned to engage the ramped surface 228 in the central extension 224 in each of the first and second endplates 14, 16. In other words, one of the angled surfaces 246 can be upwardly facing and configured, in one embodiment, to engage the ramped surface 228 in the central extension 224 in the second endplate 16. In an embodiment, the engagement between the angled surfaces 246 of the second end 236 of the central ramp 18 with the ramped surface 228 in the first and second endplates 14, 16 may be described as a dovetail connection.

The second end 236, in an exemplary embodiment, can further include an extension 252. In the illustrated embodiment, the extension 252 is generally cylindrical in shape with a through bore 254 extending longitudinally therethrough. In one embodiment, the extension 252 can include a beveled end 256. While not illustrated, at least a portion of the extension 252 can be threaded.

Figure 19:
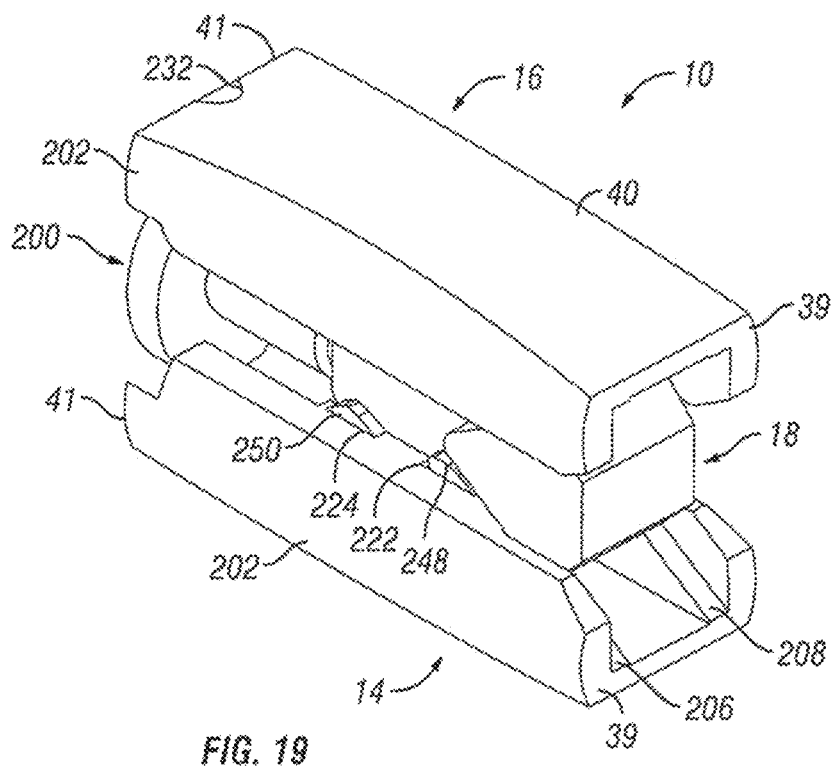
FIG. 19 is a front perspective view of the expandable fusion device of FIG. 18 shown in an expanded position in accordance with one embodiment of the present invention.
Figure 20:
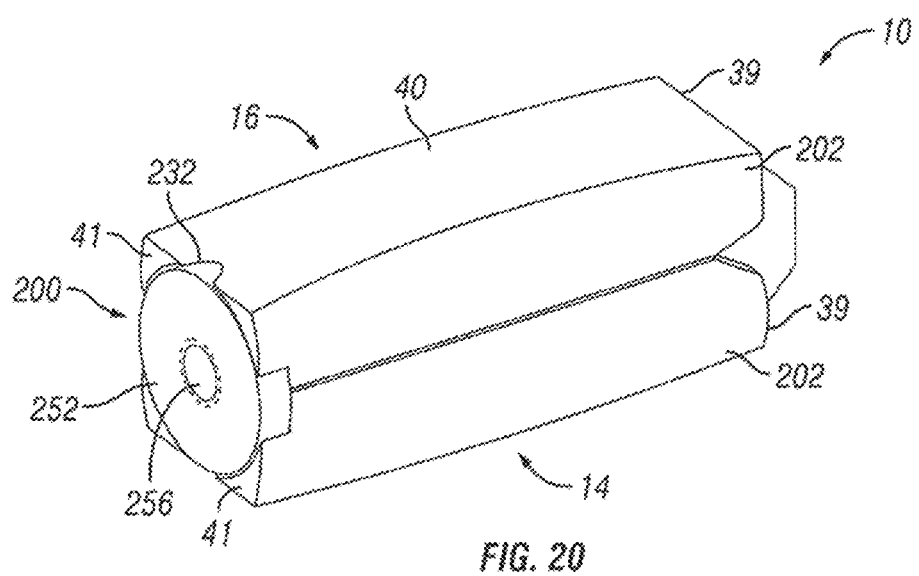
FIG. 20 is a rear perspective view of the expandable fusion device of FIG. 18 shown in an unexpanded position in accordance with one embodiment of the present invention.
Figure 21:
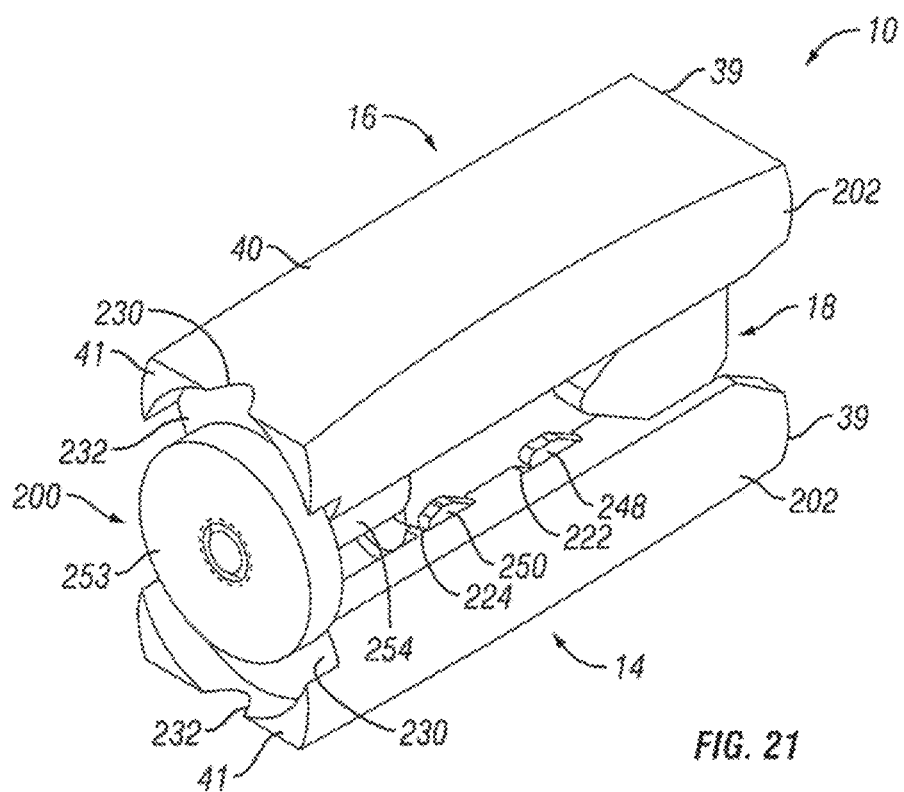
FIG. 21 is a rear perspective view of the expandable fusion device of FIG. 18 shown in an expanded position in accordance with one embodiment of the present invention.

Referring still to FIGS. 25-27, the central ramp 18 can further include features for securing the first and second endplates 14, 16 when the expandable fusion device 10 is in an expanded position. In an embodiment, the body portion 232 of the central ramp 18 includes one or more protuberances 248, 250 extending from opposing sides of the body portion 232. As illustrated, the protuberances 248, 250, in one embodiment, can be spaced along the body portion 232. In an exemplary embodiment, the protuberances 248, 250 can be configured and dimensioned for insertion into the corresponding slots 222, 224 in the first and second endplates 14, 16 when the device 10 is in an expanded position, as best seen in FIGS. 19 and 21. The protuberances 248, 250 can engage the endplates 14, 16 preventing and/or restricting movement of the endplates 14, 16 with respect to the central ramp 18 after expansion of the device 10.

With reference to FIGS. 20-23, in an exemplary embodiment, the actuator assembly 200 has a flanged end 253 configured and dimensioned to engage the stop 232 in the central extension 224 of the first and the second endplates 14, 16. In an embodiment, the actuator assembly 200 further includes an extension 254 that extends from the flanged end 253. In a further embodiment, the actuator assembly 200 includes a threaded hole 256 that extends through the actuator assembly 200. It should be understood that, while the threaded hole 256 in the actuator assembly 200 is referred to as threaded, the threaded hole 256 may only be partially threaded in accordance with one embodiment. In an exemplary embodiment, the threaded hole 256 is configured and dimensioned to threadingly receive the extension 252 of the central ramp 18.

Figure 28:
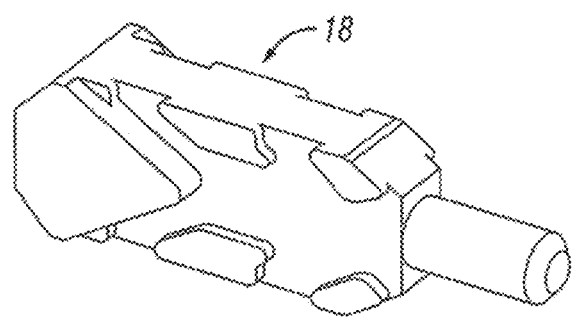
FIG. 28 a perspective view showing placement of the central ramp of the expandable fusion device of FIG. 18 in accordance with one embodiment of the present invention.
Figure 29:
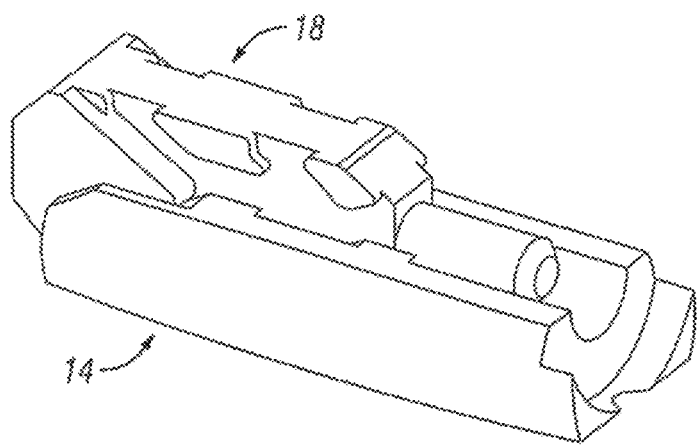
FIG. 29 is a perspective view showing placement of the first endplate of the expandable fusion device of FIG. 18 in accordance with one embodiment of the present invention.
Figure 30:
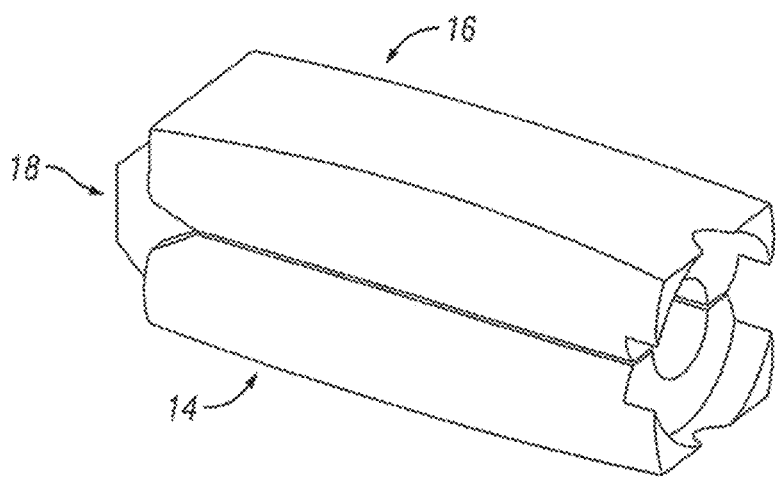
FIG. 30 is a perspective view showing placement of the second endplate of the expandable fusion device of FIG. 18 in accordance with one embodiment of the present invention.
Figure 31:
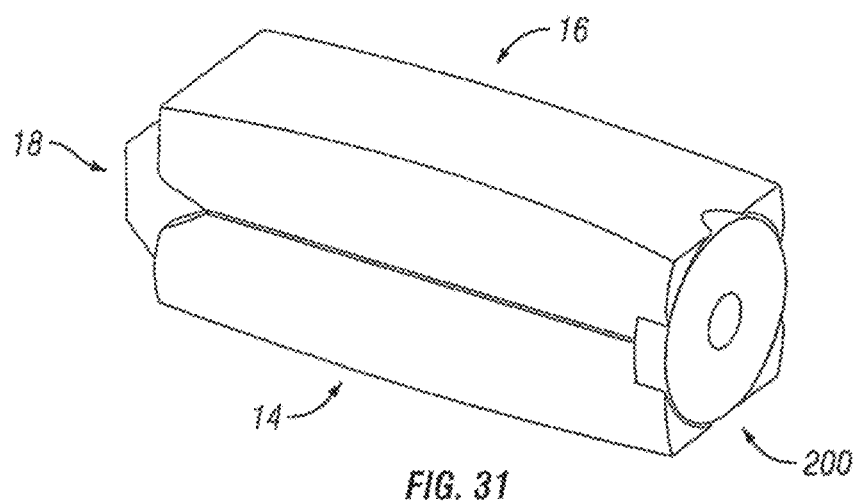
FIG. 31 is a perspective view showing placement of the actuation member of the expandable fusion device of FIG. 18 in accordance with one embodiment of the present invention.
Figure 32:
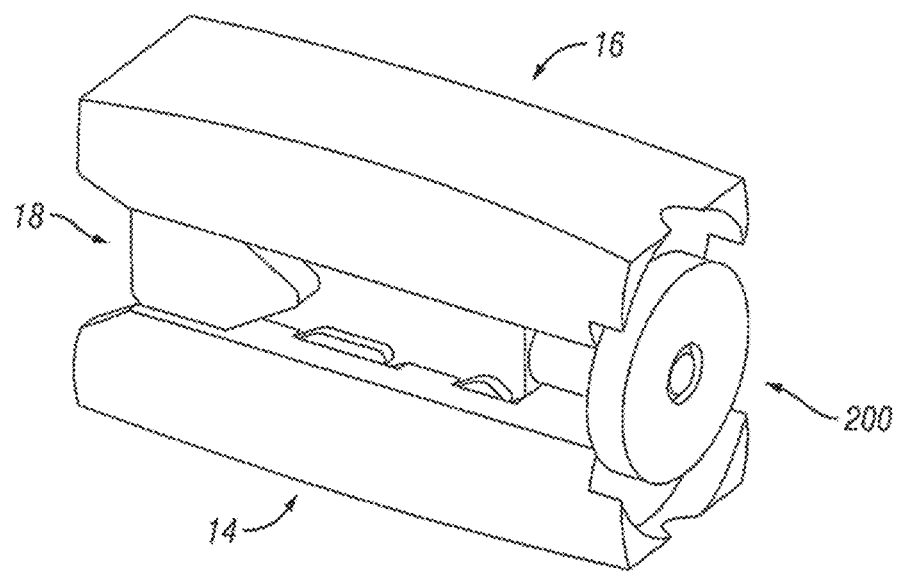
FIG. 32 is a perspective view showing expansion of the expandable fusion device of FIG. 18 in accordance with one embodiment of the present invention.
Figure 33:
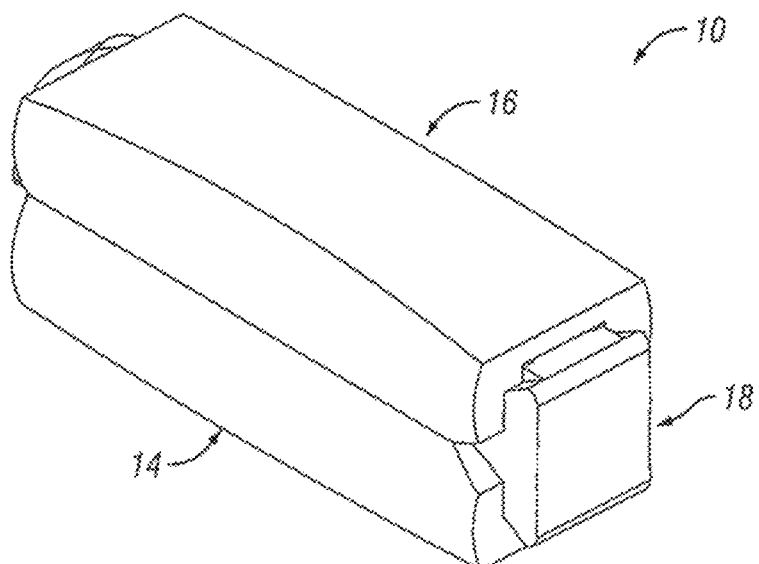
FIG. 33 is a front perspective view of an alternative embodiment of an expandable fusion device shown in an unexpanded position in accordance with one embodiment of the present invention.
Figure 34:
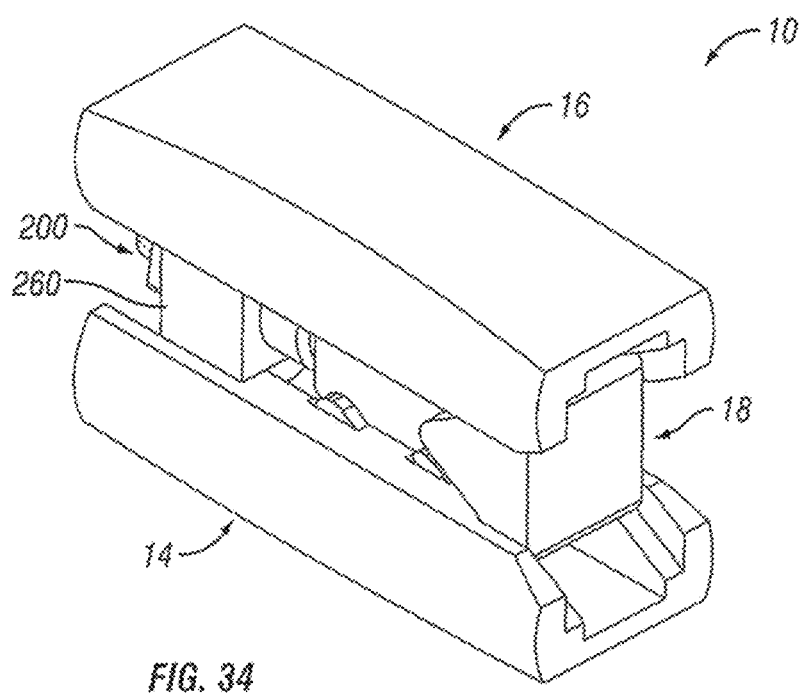
FIG. 34 is a front perspective view of the expandable fusion device of FIG. 33 shown in an expanded position in accordance with one embodiment of the present invention.
Figure 35:
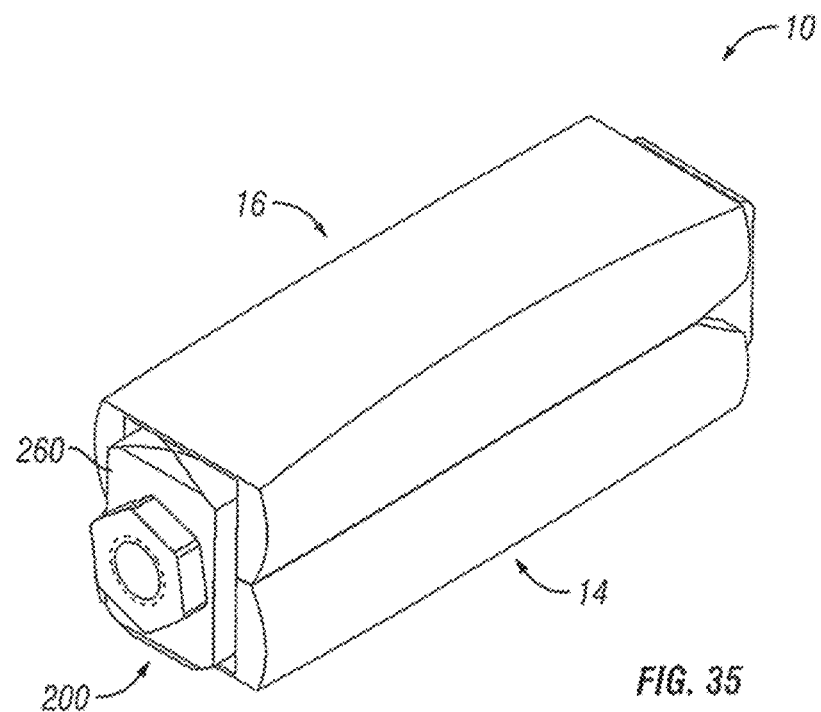
FIG. 35 is a rear perspective view of the expandable fusion device of FIG. 33 shown in an unexpanded position in accordance with one embodiment of the present invention.
Figure 36:
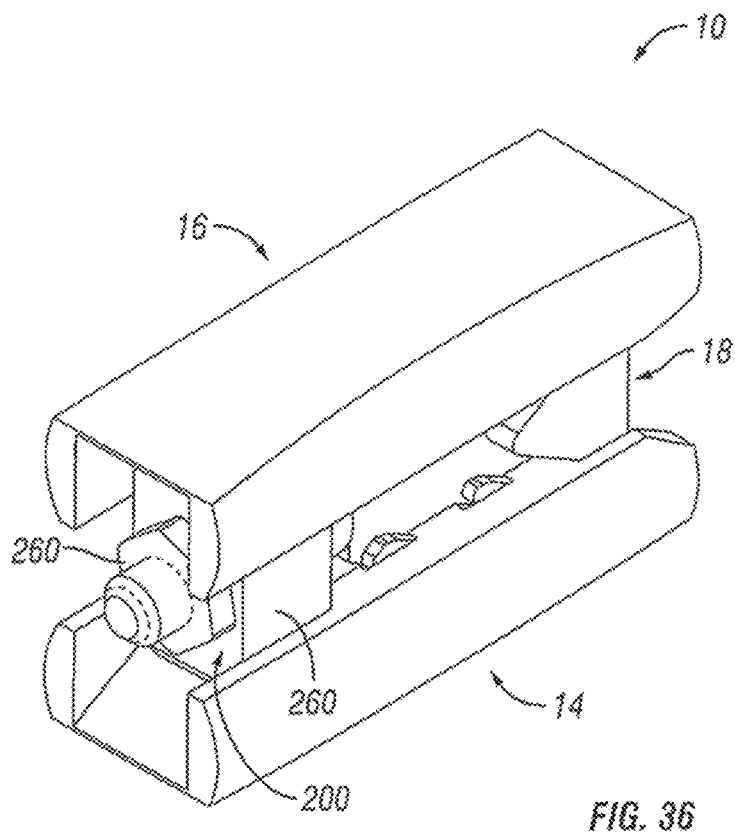
FIG. 36 is a rear perspective view of the expandable fusion device of FIG. 33 shown in an expanded position in accordance with one embodiment of the present invention.
Figure 37:
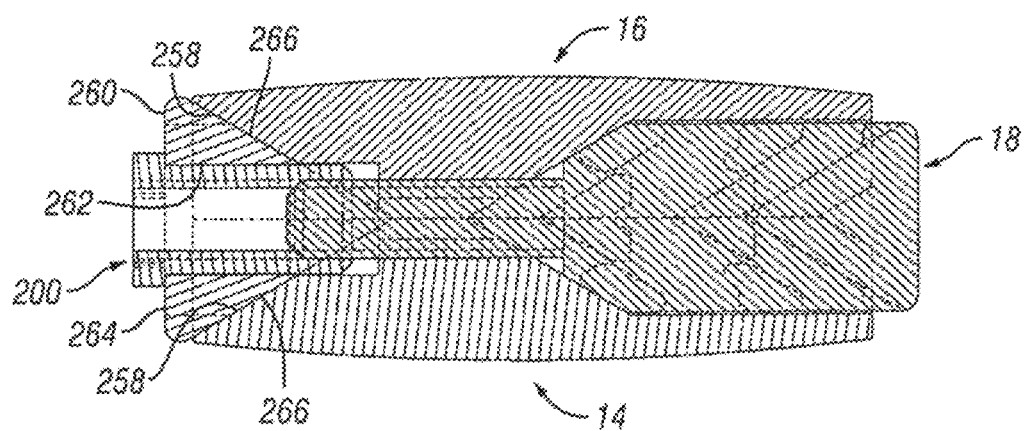
FIG. 37 is a side cross-sectional view of the expandable fusion device of FIG. 33 shown in an unexpanded position in accordance with one embodiment of the present invention.
Figure 38:
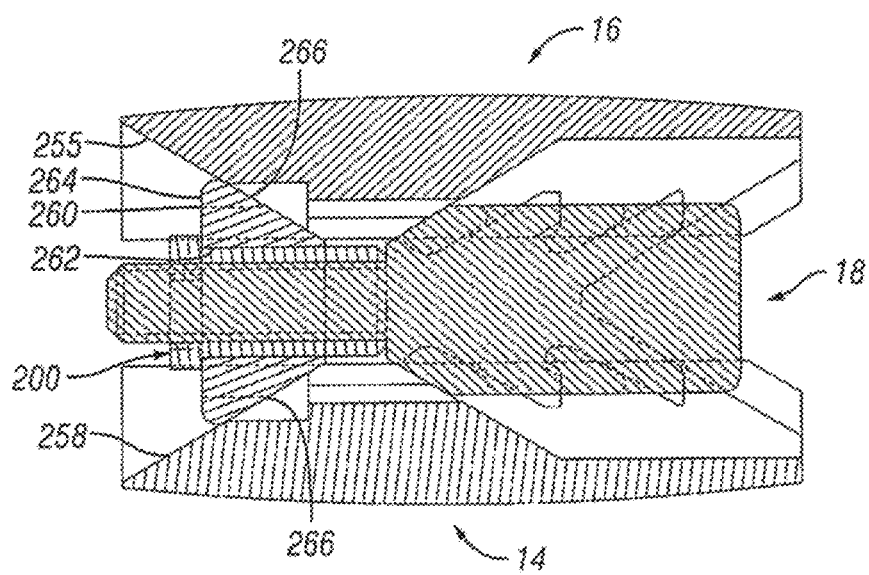
FIG. 38 is a side cross-sectional view of the expandable fusion device of FIG. 33 shown in an expanded position in accordance with one embodiment of the present invention.

With additional reference to FIGS. 28-32, a method of installing the expandable fusion device 10 of FIGS. 18-27 is now discussed in accordance with one embodiment of the present invention. Prior to insertion of the fusion device, the disc space may be prepared as described above and then one or more endoscopic tubes may then inserted into the disc space. The expandable fusion device 10 can then be inserted into and seated in the appropriate position in the intervertebral disc space, as best seen in FIGS. 28-32. The expandable fusion device 10 can be introduced into the intervertebral space down an endoscopic tube (not illustrated), with the central ramp 18 being first placed down the tube and into the disc space, as seen in FIG. 28. After insertion of the central ramp, the first endplate 14 can be placed down an endoscopic tube, as shown on FIG. 29, followed by insertion of the second endplate 16, as shown on FIG. 30. After the second endplate 16, the actuator assembly 200 can then be inserted to complete assembly of the device 10, as best seen in FIG. 31.

Figure 22:
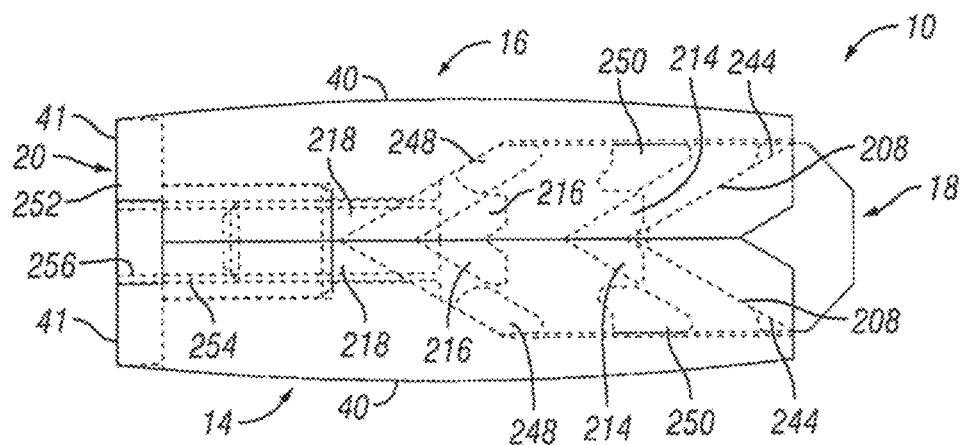
FIG. 22 is a side view of the expandable fusion device of FIG. 18 shown in an unexpanded position in accordance with one embodiment of the present invention.
Figure 23:
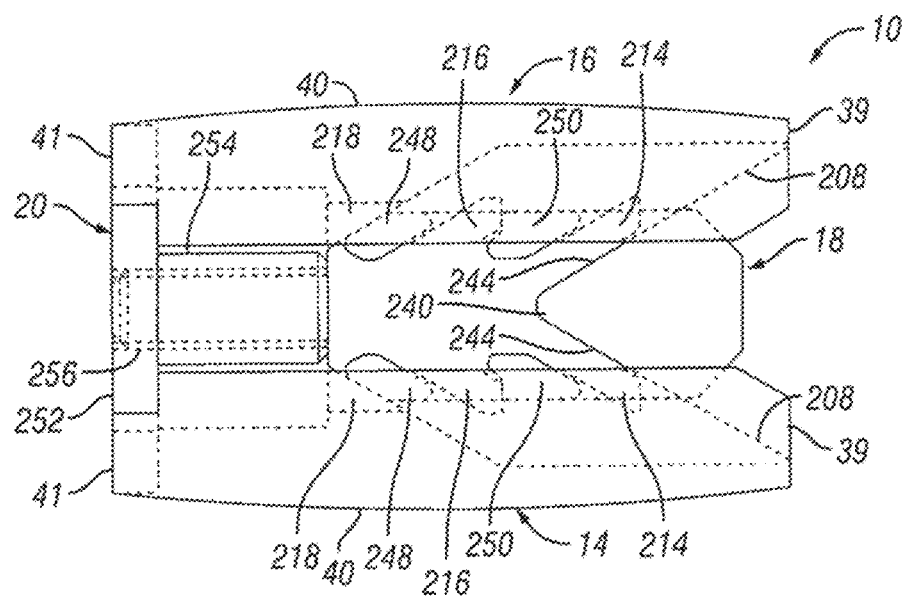
FIG. 23 is a side view of the expandable fusion device of FIG. 18 shown in an expanded position in accordance with one embodiment of the present invention.

After the fusion device 10 has been inserted into and assembled in the appropriate position in the intervertebral disc space, the fusion device 10 can then be expanded into the expanded position. To expand the fusion device 10, the actuator assembly 200 can be rotated. As discussed above, the actuator assembly 200 is in threaded engagement with the extension 250 of the central ramp 18. Thus, as the actuator assembly 200 is rotated in a first direction, the central ramp 18 moves toward the flanged end 253 of the actuator assembly 200. In another exemplary embodiment, the actuator assembly 200 can be moved in a linear direction with the ratchet teeth as means for controlling the movement of the central ramp 18. As the central ramp 18 moves, the angled surfaces 242, 244 in the expansion portions 238, 240 of the central ramp 18 push against the ramped surfaces 206, 208 in the first and second side portions 202, 204 of the first and second endplates 14, 16. In addition, the angled surfaces 246 in the second end 236 of the central ramp 18 also push against the ramped surfaces 228 in the central extension 224 of each of the endplates 14, 16. This is best seen in FIGS. 22-23.

Since the expansion of the fusion device 10 is actuated by a rotational input, the expansion of the fusion device 10 is infinite. In other words, the endplates 14, 16 can be expanded to an infinite number of heights dependent on the rotational advancement of the actuator assembly 200. As discussed above, the central ramp 16 includes locking features for securing the endplates 14, 16.

In the event the fusion device 10 needs to be repositioned or revised after being installed and expanded, the fusion device 10 can be contracted back to the unexpanded configuration, repositioned, and expanded again once the desired positioning is achieved. To contract the fusion device 10, the actuator assembly 200 can be rotated in a second direction. As discussed above, actuator assembly 200 is in threaded engagement with the extension 250 of the central ramp 18; thus, as the actuator assembly 200 is rotated in a second direction, opposite the first direction, the central ramp 18 moves with respect to the actuator assembly 200 and the first and second endplates 14, 16 away from the flanged end 253. As the central ramp 18 moves, the first and second endplates are pulled inwardly into the unexpanded position.

Referring now to FIGS. 33-38, an alternative embodiment of the expandable fusion device 10 is shown. In the illustrated embodiment, the fusion device includes a first endplate 14, a second endplate 16, a central ramp 18, and an actuator assembly 200. The fusion device 10 of FIGS. 33-38 and its individual components are similar to the device 10 illustrated on FIGS. 18-23 with several modifications. The modifications to the device 10 will be described in turn below.

Figure 39:
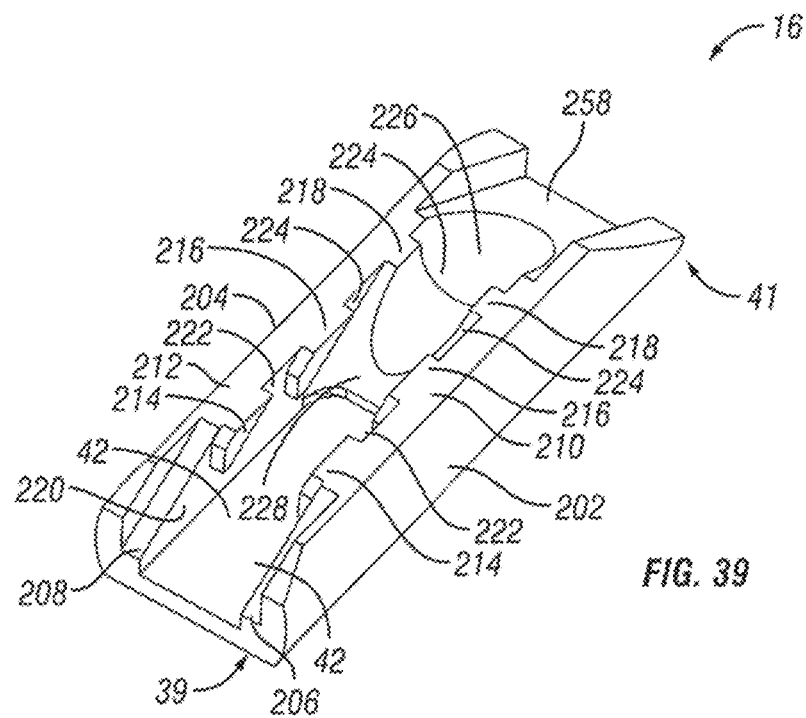
FIG. 39 is a perspective of an endplate of the expandable fusion device of FIG. 33 in accordance with one embodiment of the present invention.

Although the following discussion relates to the second endplate 16, it should be understood that it also equally applies to the first endplate 14 as the second endplate 16 is substantially identical to the first endplate 14 in embodiments of the present invention. With additional reference to FIG. 39, in an exemplary embodiment, the lower surface 42 of the second endplate 16 has been modified. In one embodiment, the central extension 224 extending from the lower surface 42 has been modified to include a second ramped surface 258 rather than a stop. In an exemplary embodiment, the second ramped surface 258 faces the second end 41 of the second endplate 16. In contrast, ramped surface 228 on the central extension 228 faces the first end 39 of the second endplate. The concave surface 228 connects the ramped surface 228 and the second ramped surface 258.

With reference to FIGS. 35-38, in an exemplary embodiment, the actuator assembly 200 has been modified to further include a driving ramp 260. In the illustrated embodiment, the driving ramp 260 has a through bore 262 through which the extension 254 extends. In an embodiment, the driving ramp 260 is generally wedge-shaped. As illustrated, the driving ramp 260 may comprise a blunt end 264 in engagement with the flanged end 253. In an exemplary embodiment, the driving ramp 260 further comprises angled surfaces 266 configured and dimensioned to engage the second ramped surface 258 of each of the endplates 14, 16 and force apart the first and second endplates 14, 16.

Referring now to FIGS. 40-44, an alternative embodiment of the expandable fusion device 10 is shown. In the illustrated embodiment, the fusion device 10 includes a first endplate 14, a second endplate 16, a central ramp 18, an actuator assembly 200, and a driving ramp 300. As will be discussed in more detail below, the actuator assembly 200 functions, in an embodiment, to pull the central ramp 18 and the driving ramp 300 together, which forces apart the first and second endplates 14, 16.

Although the following discussion relates to the first endplate 14, it should be understood that it also equally applies to the second endplate 16 as the second endplate 16 is substantially identical to the first endplate 14 in embodiments of the present invention. With reference to FIGS. 40-45, in an exemplary embodiment, the first endplate 14 has a first end 39 and a second end 41. In the illustrated embodiment, the first endplate 14 further comprises an upper surface 40 connecting the first end 39 and the second end 41, and a lower surface 42 connecting the first end 39 and the second end 41. While not illustrated, in an embodiment, the first endplate 14 may comprise further comprises a through opening. The through opening, in an exemplary embodiment, is sized to receive bone graft or similar bone growth inducing material.

In one embodiment, the upper surface 40 of the first endplate 14 is flat and generally planar to allow the upper surface 40 of the endplate 14 to engage with the adjacent vertebral body 2. Alternatively, as shown in FIG. 15, the upper surface 40 can be curved convexly or concavely to allow for a greater or lesser degree of engagement with the adjacent vertebral body 2. It is also contemplated that the upper surface 40 can be generally planar but includes a generally straight ramped surface or a curved ramped surface. The ramped surface allows for engagement with the adjacent vertebral body 2 in a lordotic fashion. While not illustrated, in an exemplary embodiment, the upper surface 40 includes texturing to aid in gripping the adjacent vertebral bodies. Although not limited to the following, the texturing can include teeth, ridges, friction increasing elements, keels, or gripping or purchasing projections.

In one embodiment, the first endplate 14 further comprises a first side portion 202 connecting the first end 39 and the second end 41, and a second side portion 204 connecting the first end 39 and the second end 41. In the illustrated embodiment, the first and second side portions 202, 204 are extensions from the lower surface 42. In an embodiment, the first and second side portions each have an interior surface 302 and an exterior surface 304. In an exemplary embodiment, the first and second side portions 202, 204 each include one or more ramped portions. In the illustrated embodiment, the first and second side portions 202, 204 include first ramped portions 306, 308 at the first end 39 of the endplate 14 and second ramped portions 310, 312 at the second end 41 of the endplate. The first and second side portions 202, 204 each can include a bridge portion 314 connecting the first ramped portions 306, 308 and the second ramped portions 310, 312. In an embodiment, the first ramped portions 306, 308 abut the exterior surface 304 of the respective side portions 202, 204, and the second ramped portions 310, 312 abut the interior surface 302 of the respective side portions 202, 204. As illustrated, the first ramped portions 306, 308 may include tongue portions 316, 318 with the tongue portions 316, 318 extending in an oblique direction with respect to the upper surface 40 of the endplate 14. As further illustrated, the second ramped portions 310, 312 may include tongue portions 320, 322 that extend in an oblique direction with respect to the upper surface 40 of the endplate 14.

Figure 45:
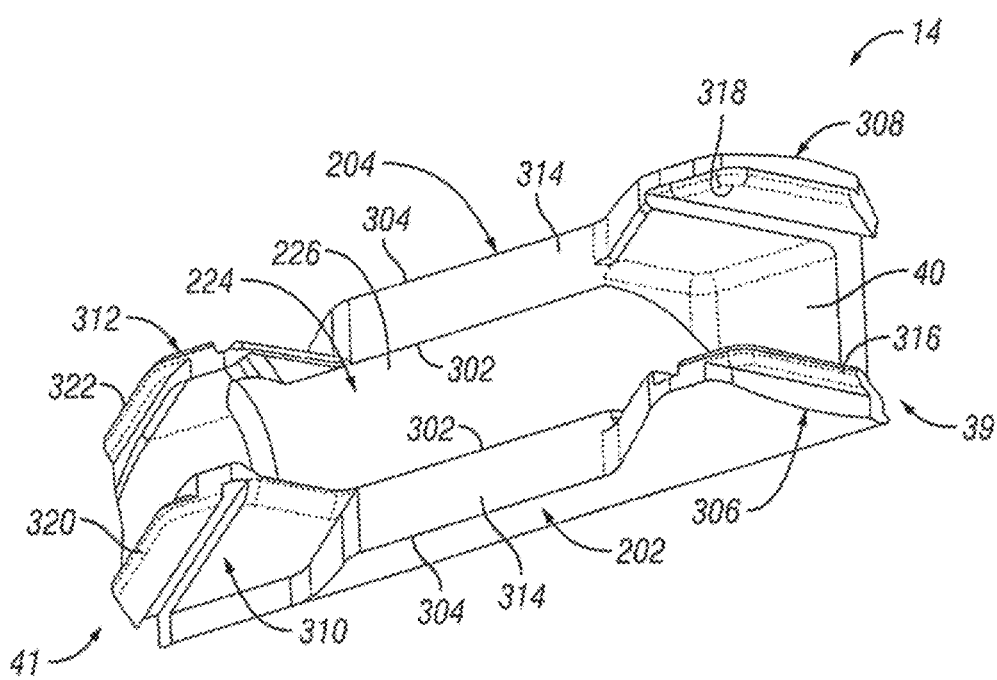
FIG. 45 is a perspective view of an endplate of the expandable fusion device of FIG. 40 in accordance with one embodiment of the present invention.

As best seen in FIG. 45, the lower surface 42 of the second endplate 16, in an embodiment, includes a central extension 224 extending along at least a portion of the lower surface. In the illustrated embodiment, the central extension 224 extends between the first and second side portions 202 and 204. In an exemplary embodiment, the central extension 224 can extend generally between the first ramped portions 306, 308 and the second ramped portions 310, 312. In one embodiment, the central extension 224 includes a generally concave surface 226 configured and dimensioned to form a through bore with the corresponding concave surface 226 (not illustrated) of the second endplate 16.

Figure 43:
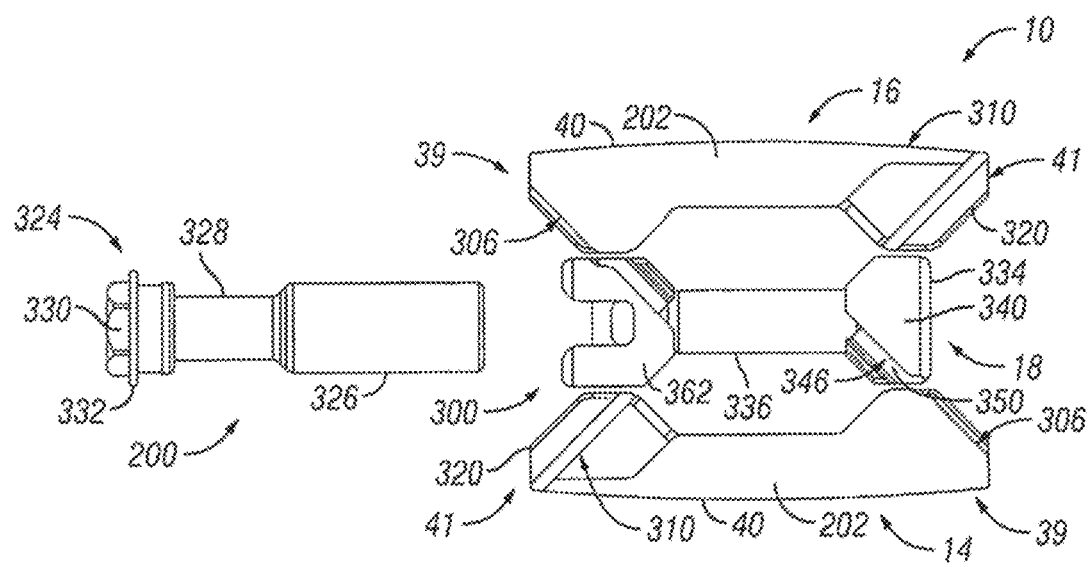
FIG. 43 is a side exploded view of the expandable fusion device of FIG. 40 in accordance with one embodiment of the present invention.
Figure 44:
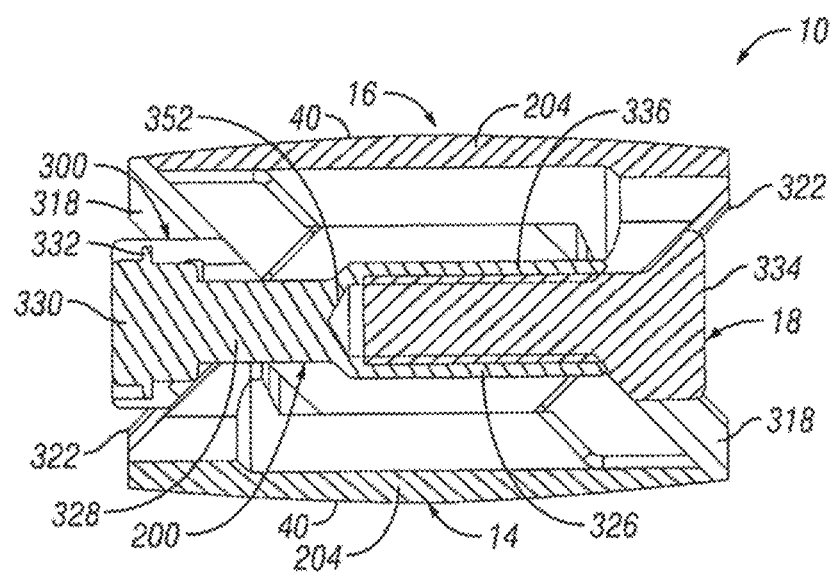
FIG. 44 is a side cross-sectional view of the expandable fusion device of FIG. 40 shown in an unexpanded position in accordance with one embodiment of the present invention.

With reference to FIGS. 43 and 44, the actuator assembly 200 includes a head portion 324, a rod receiving extension 326, and a connecting portion 328 that connecting portions that connects the head portion 324 and the rod receiving extension 326. As illustrated, the head portion 324 may include one or more instrument gripping features 330 that can allow it to be turned by a suitable instrument. In addition, the head portion 324 has a larger diameter than the other components of the actuator assembly 200 to provide a contact surface with the driving ramp 300. In the illustrated embodiment, the head portion 324 includes a rim 332 that provides a surface for contacting the driving ramp 300. As can be seen in FIG. 44, in an exemplary embodiment, the rod receiving extension 326 includes an opening sized and dimensioned to receive the extension 336 of the central ramp 18. In an embodiment, the rod receiving extension 326 includes threading for threadingly engaging the extension 336. In another embodiment, the rod receiving extension 326 includes ratchet teeth for engaging the extension 336. In the illustrated embodiment, the head portion 324 and the rod receiving extension 326 are connected by connecting portion 328 which can be generally cylindrical in shape.

Figure 46:
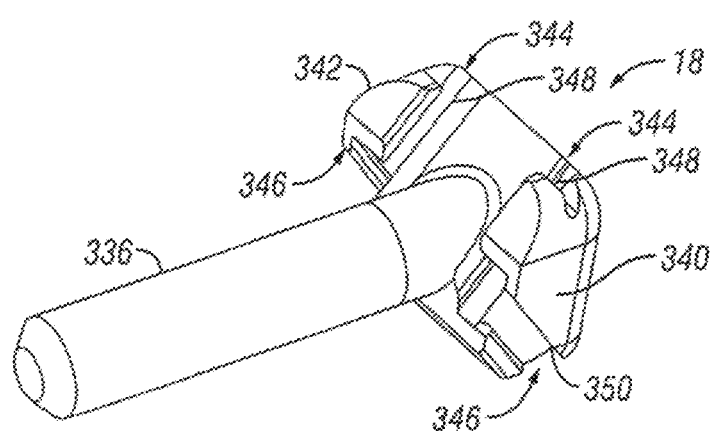
FIG. 46 is a perspective view of the central ramp of the expandable fusion device of FIG. 40 in accordance with one embodiment of the present invention.
Figure 50:
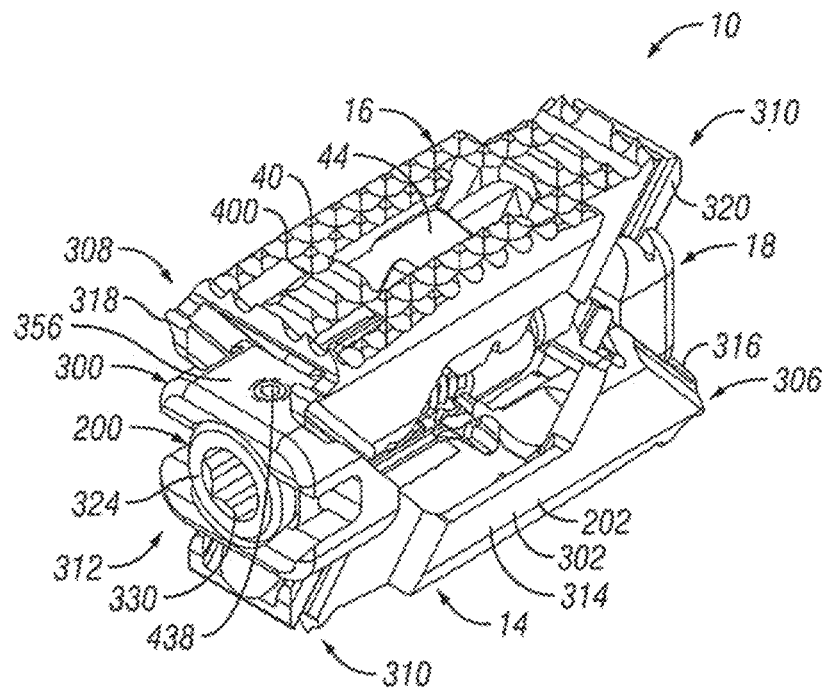
FIG. 50 is a rear perspective view of an alternative embodiment of an expandable fusion device shown in an expanded position in accordance with one embodiment of the present invention.

With reference to FIGS. 43, 44, and 46, the central ramp 18 includes expansion portion 334 and extension 336. As best seen in FIG. 46, the expansion portion 334 may include an upper portion 338 and side portions 340, 342 that extend down from the upper portion 338. In an embodiment, each of the side portions 340, 342 include dual, overlapping ramped portions. For example, side portions 340, 342 each include a first ramped portion 344 that overlaps a second ramped portion 346. In the illustrated embodiment, the first ramped portion 344 faces the extension 336 while the second ramped portion 344 faces away from the extension 336. In one embodiment, angled grooves 348, 350 are formed in each of the first and second ramped portions 344, 346. In another embodiment, the angled grooves 348, 350 are sized to receive the corresponding tongues 316, 318, 320, 322 in the first and second endplates with angled grooves 348 receiving tongues 320, 322 in the second endplate 16 and angled grooves 350 receiving tongues 316, 318 in the first endplate 14. Although the device 10 is described with tongues 316, 318, 320, 322 on the endplates 14, 16 and angled grooves 348, 350 on the central ramp 18, it should be understood that that device 10 can also be configured with grooves on the endplates 14, 16 and tongues on the central ramp 18, in accordance with one embodiment of the present invention.

In an exemplary embodiment, the extension 336 is sized to be received within the rod receiving extension 326 of the actuator assembly 200. In one embodiment, the extension 336 has threading with the extension 336 being threadingly received within the rod receiving extension 326. In another embodiment, the extension 336 has ratchet teeth with the extension 336 being ratcheted into the rod receiving extension 336. In an embodiment, the extension 336 include nose 352 at the end of the extension 336.

With reference to FIGS. 47-49, in an exemplary embodiment, the driving ramp 300 includes an upper portion 354 having an upper surface 356 and an oblique surface 358. In an embodiment, the driving ramp 300 further includes side portions 360, 362 that extend from the upper portion 354 connecting the upper portion 354 with the lower portion 364 of the driving ramp 300. As best seen in FIGS. 48-49, the driving ramp 300 further includes a bore 366, in an exemplary embodiment, sized to receive the connection portion 328 of the actuator assembly 200. In one embodiment, the driving ramp 300 moves along the connection portion 328 when the actuator assembly 200 is pushing the driving ramp 300. In an exemplary embodiment, the driving ramp 300 further includes contact surface 368 that engages the rim 332 of the head portion 324 of the actuator assembly 200. In the illustrated embodiment, the contact surface 368 has a generally annular shape.

In an exemplary embodiment, the side portions 360, 362 of the driving ramp 300 each include overlapping ramped portions. For example, the side portions 360, 362 each include first ramped portions 370 that overlap second ramped portions 372. In the illustrated embodiment, the first ramped portions 370 face central ramp 18 while the second ramped portions 372 face the opposite direction. In one embodiment, angled grooves 374, 376 are formed in each of the first and second ramped portions 370, 372. FIG. 48 is a perspective view of the driving ramp 300 that shows the top ends of the angled grooves 374 in ramped portions 370. FIG. 49 is a perspective view of the driving ramp 300 that shows the top ends of the angled grooves 376 in ramped portions 372. In an exemplary embodiment, the angled grooves 374, 376 are sized to receive corresponding tongues 316, 318, 320, 322 in the first and second endplates 14, 16 with angled grooves 370 receiving tongues 316, 318 in the second endplate 16 and angled grooves 372 receiving tongues 320, 322 in the first endplate 14. Although the device 10 is described with tongues 316, 318, 320, 322 in the first and second endplates 14, 16 and angled grooves 370, 372, 374, 376 on the driving ramp 300, it should be understood that that device 10 can also be configured with grooves on the second endplate 16 and tongues on the driving ramp 300, in accordance with one embodiment of the present invention.

Figure 40:
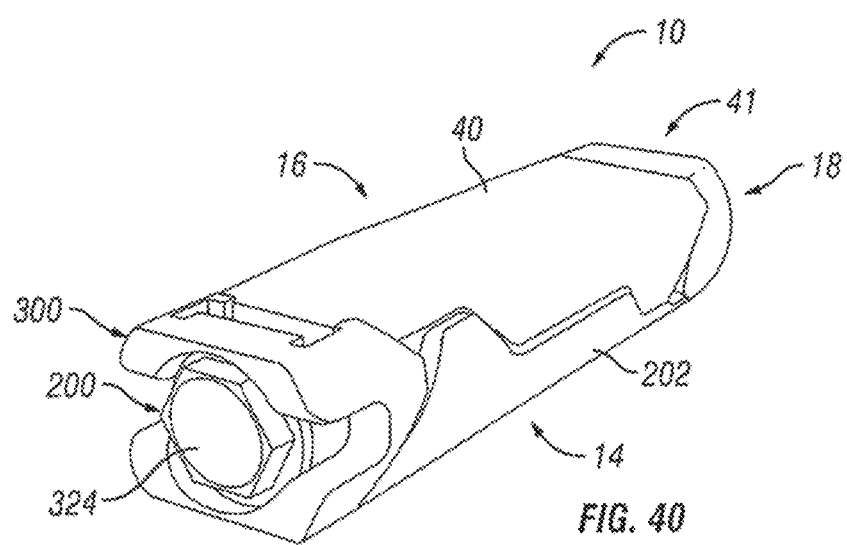
FIG. 40 is a rear perspective view of an alternative embodiment of an expandable fusion device shown in an unexpanded position in accordance with one embodiment of the present invention.
Figure 41:
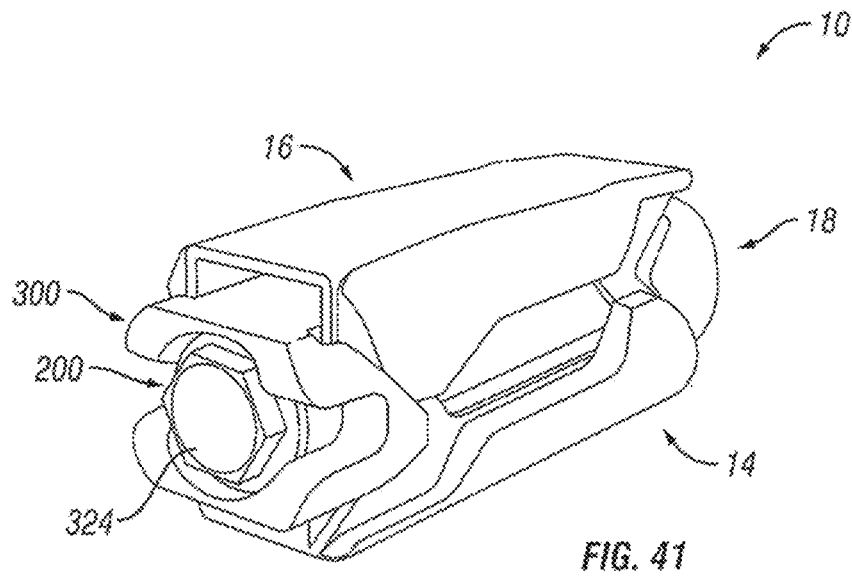
FIG. 41 is a rear perspective view of the expandable fusion device of FIG. 40 shown in a partially expanded position in accordance with one embodiment of the present invention.
Figure 42:
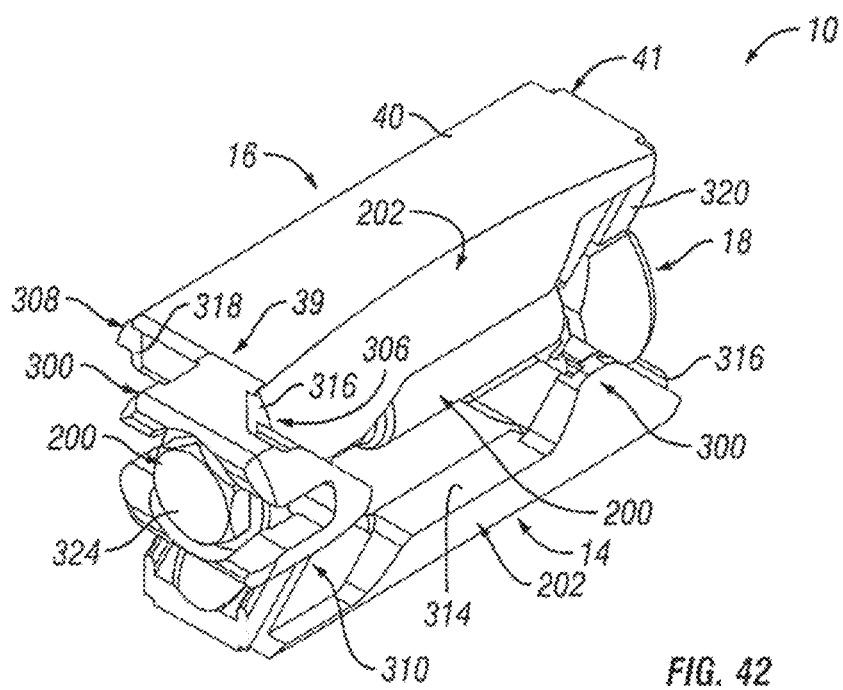
FIG. 42 is a rear perspective view of the expandable fusion device of FIG. 40 shown in an expanded position in accordance with one embodiment of the present invention.

Turning now to FIGS. 40-42, a method of installing the expandable fusion device 10 of FIGS. 40-49 is now discussed in accordance with one embodiment of the present invention. Prior to insertion of the fusion device, the disc space may be prepared as described above. The expandable fusion device 10 can then be inserted into and seated in the appropriate position in the intervertebral disc space. The expandable fusion device 10 is then introduced into the intervertebral space, with the end having the expansion portion 334 of the central ramp 18 being inserted. In an exemplary method, the fusion device 10 is in the unexpanded position when introduced into the intervertebral space. In an exemplary method, the intervertebral space may be distracted prior to insertion of the fusion device 10. The distraction provides some benefits by providing greater access to the surgical site making removal of the intervertebral disc easier and making scraping of the endplates of the vertebral bodies 2, 3 easier.

With the fusion device 10 inserted into and seated in the appropriate position in the intervertebral disc space, the fusion device can then be expanded into the expanded position, as best seen in FIG. 42. To expand the fusion device 10, an instrument is engaged with the head portion 324 of the actuator assembly 200. The instrument is used to rotate actuator assembly 200. As discussed above, actuator assembly 200 is threadingly engaged with the extension 336 of the central ramp 18; thus, as the actuator assembly 200 is rotated in a first direction, the central ramp 18 is pulled toward the actuator assembly 200. In an exemplary embodiment, the actuator assembly 200 is moved in a linear direction with the ratchet teeth engaging as means for controlling the movement of the actuator assembly 200 and the central ramp 18. As the central ramp 18 is pulled towards the actuator assembly 200, the first ramped portions 344 of the central ramp 18 push against the second ramped portions 310, 312 of the second endplate 16 and the second ramped portions 346 of the central ramp 18 push against first ramped portions 306, 308 of the first endplate 14. In this manner, the central ramp 18 acts to push the endplates 14, 16 outwardly into the expanded position. This can best be seen in FIGS. 40-42. As the endplates 14, 16 move outwardly the tongues 316, 318, 320, 322 in the endplates 14, 16 ride in the angled grooves 348, 350 with the tongues 320, 322 in the second endplate 16 riding in angled grooves 348 and the tongues 316, 318 in the first endplate 14 riding in angled grooves 350.

As discussed above, the actuator assembly 200 also engages driving ramp 300; thus, as the actuator assembly 200 is rotated in a first direction, the actuator assembly 200 pushes the driving ramp 300 towards the central ramp 18 in a linear direction. As the driving ramp 300 is pushed towards the central ramp 18, the first ramped portions 370 of the driving ramp 300 push against the first ramped portions 306, 308 of the second endplate 16 and the second ramped portions 372 of the driving ramp 300 push against the second ramped portions 310, 312 of the first endplate 14. In this manner, the driving ramp 300 also acts to push the endplates 14, 16 outwardly into the expanded position. This can best be seen in FIGS. 40-42. As the endplates 14, 16 move outwardly the tongues 316, 318, 320, 322 in the endplates 14, 16 ride in the angled grooves 370, 372 with the tongues 316, 318 in the second endplate 16 riding in angled grooves 370 and the tongues 320, 322 in the first endplate 14 riding in angled grooves 372.

Since the expansion of the fusion device 10 is actuated by a rotational input, the expansion of the fusion device 10 is infinite. In other words, the endplates 14, 16 can be expanded to an infinite number of heights dependent on the rotational advancement of the actuator assembly 200.

Referring now to FIGS. 50-54, an alternative embodiment of the expandable fusion device 10 is shown. In the illustrated embodiment, the fusion device 10 includes a first endplate 14, a second endplate 16, a central ramp 18, an actuator assembly 200, and a driving ramp 300. As will be discussed in more detail below, the actuator assembly 200 functions, in an embodiment, to pull the central ramp 18 and the driving ramp 300 together, which forces apart the first and second endplates 14, 16. In an embodiment, the expandable fusion device may contain features, such as a through bore, that facilitate placement down an endoscopic tube. In an embodiment, the assembled fusion device 10 may be placed down the endoscopic tube and then expanded.

Figure 54:
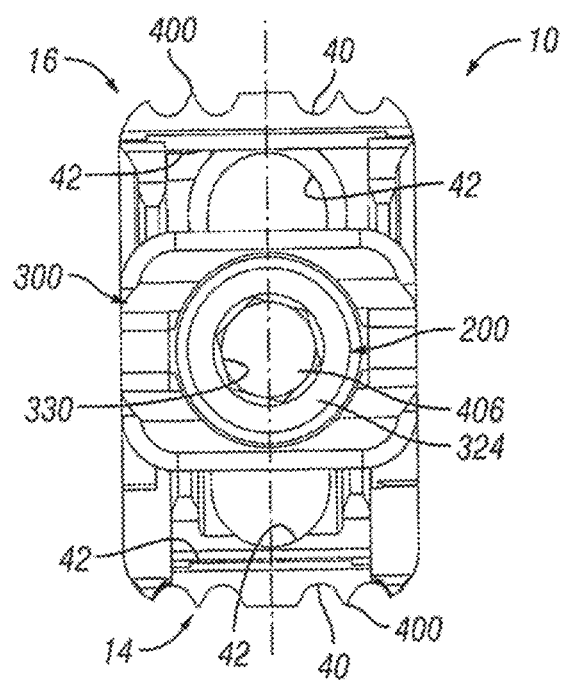
FIG. 54 is a read end view of the expandable fusion device of FIG. 50 shown in an expanded position in accordance with one embodiment of the present invention.
Figure 55:
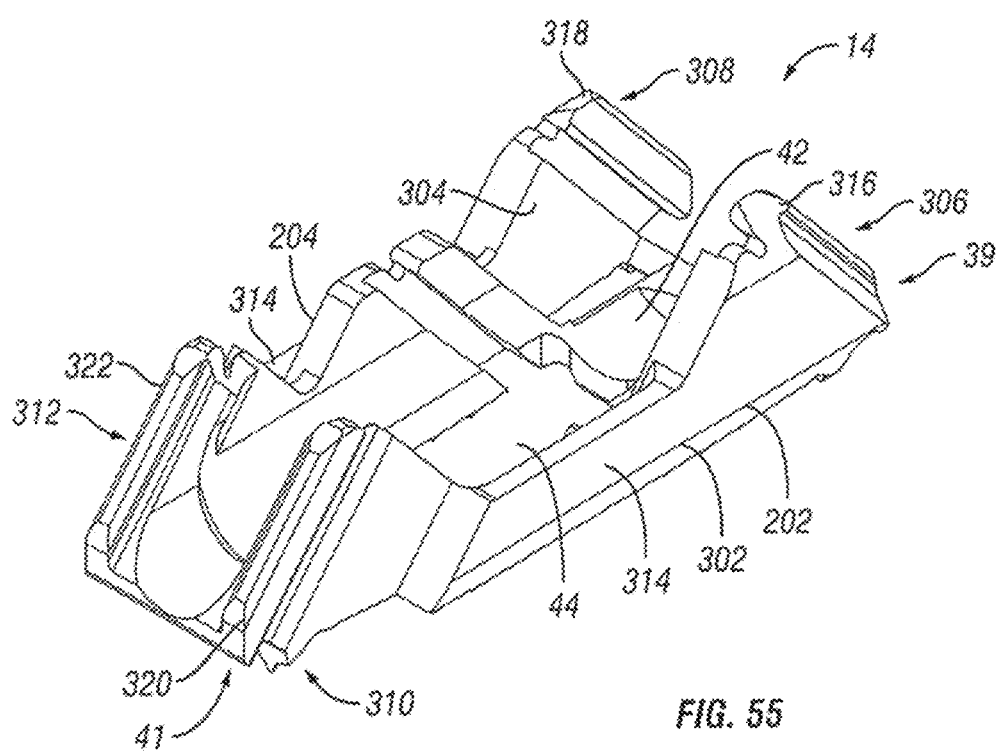
FIG. 55 is a perspective view of an endplate of the expandable fusion device of FIG. 50 in accordance with one embodiment of the present invention.

Although the following discussion relates to the first endplate 14, it should be understood that it also equally applies to the second endplate 16 as the second endplate 16 is substantially identical to the first endplate 14 in embodiments of the present invention. It should be understood that, in an embodiment, the first endplate 14 is configured to interlock with the second endplate 16. With additional reference to FIG. 55, in an exemplary embodiment, the first endplate 14 has a first end 39 and a second end 41. As illustrated, the first end 39 may be wider than the second end 41. In the illustrated embodiment, the first endplate 14 further comprises an upper surface 40 connecting the first end 39 and the second end 41, and a lower surface 42 connecting the first end 39 and the second end 41. As best seen in FIG. 54, the lower surface 42 can be curved concavely such that the first and second endplates 14, 16 form a through bore when the device 10 is in a closed position. In an embodiment, the first endplate 14 may comprise a through opening 44. The through opening 44, in an exemplary embodiment, is sized to receive bone graft or similar bone growth inducing material.

In one embodiment, the upper surface 40 of the first endplate 14 is flat and generally planar to allow the upper surface 40 of the endplate 14 to engage with the adjacent vertebral body 2. Alternatively, as shown in FIG. 15, the upper surface 40 can be curved convexly or concavely to allow for a greater or lesser degree of engagement with the adjacent vertebral body 2. It is also contemplated that the upper surface 40 can be generally planar but includes a generally straight ramped surface or a curved ramped surface. The ramped surface allows for engagement with the adjacent vertebral body 2 in a lordotic fashion. As illustrated, in an exemplary embodiment, the upper surface 40 includes texturing to aid in gripping the adjacent vertebral bodies. For example, the upper surface 40 may further comprise texturing 400 to engage the adjacent vertebral bodies. Although not limited to the following, the texturing can include teeth, ridges, friction increasing elements, keels, or gripping or purchasing projections.

In one embodiment, the first endplate 14 further comprises a first side portion 202 connecting the first end 39 and the second end 41, and a second side portion 204 connecting the first end 39 and the second end 41. In the illustrated embodiment, the first and second side portions 202, 204 are extensions from the lower surface 42. In an embodiment, the first and second side portions 202, 204 each include an interior surface 302 and an exterior surface 304. In an embodiment, the first end 39 of the first endplate 14 is generally designed and configured to fit over the second end 41 of the second endplate 16 when the device 10 is in a closed position. As illustrated, the first and second side portions 202, 204 each may include first ramped portions 306, 308, second ramped portions 310, 312, and/or central ramped portion 402.

In an embodiment, the first ramped portions 306, 308 are proximate the first end 39 of the endplate 14. In accordance with embodiment of the present invention, the first ramped portions 306, 308 of the first endplate 14 are generally designed and configured to fit over the second ramped portions 310, 312 of the second endplate 16 when the device 10 is in a closed position. In an exemplary embodiment, the first ramped portions 306, 308 generally face the first end 39 and can extend in an oblique direction with respect to the upper surface 40, for example. As illustrated, the first ramped portions 306, 308 may include tongue portions 316, 318 extending in an oblique direction with respect to the upper surface 40 of the endplate 14.

In an embodiment, the second ramped portions 310, 312 are proximate the second end 41 of the endplate 14. In an exemplary embodiment, the second ramped portions 310, 312 can extend in an oblique direction with respect to the upper surface 40 and generally face the second end 41. The first and second side portions 202, 204, in an embodiment, each can include a bridge portion 314 connecting the first ramped portions 306, 308 and the second ramped portions 310, 312. As further illustrated, the second ramped portions 310, 312 may include tongue portions 320, 322 that extend in an oblique direction with respect to the upper surface 40 of the endplate 14.

In an embodiment, the endplate 14 further may include a central ramped portion 402 proximate the bridge portion 314. In the illustrated embodiment, the endplate 14 includes a central ramped portion 402 proximate the bridge portion 314 of the second side portion 204. In an exemplary embodiment, the central ramped portion 402 can extend in an oblique direction with respect to the upper surface 40 and face the first end 39 of the endplate 14. As illustrated, the first ramped portions 306, 308 may include tongue portions 316, 318 with the tongue portions 316, 318 extending in an oblique direction with respect to the upper surface 40 of the endplate 14.

With reference to FIGS. 50-52 and 54, in an embodiment, the actuator assembly 200 includes a head portion 324, an extension 404, and a through bore 406 that extends longitudinally through the actuator assembly 200. As illustrated, the head portion 324 may include one or more instrument gripping features 330 that can allow it to be turned by a suitable instrument. In addition, the head portion 324 has a larger diameter than the other components of the actuator assembly 200 to provide a contact surface with the driving ramp 300. In the illustrated embodiment, the head portion 324 includes a rim 332 that provides a surface for contacting the driving ramp 300. In an embodiment, the extension 404 is a generally rod-like extension. In another embodiment, the extension 404 includes ratchet teeth for engaging the extension 336.

Figure 51:
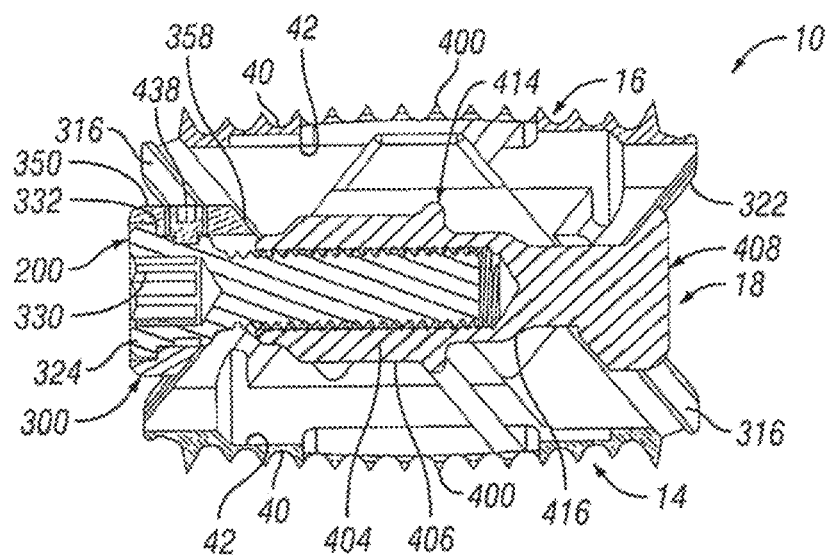
FIG. 51 is a side cross-sectional view of the expandable fusion device of FIG. 50 shown in an expanded position in accordance with one embodiment of the present invention.
Figure 52:
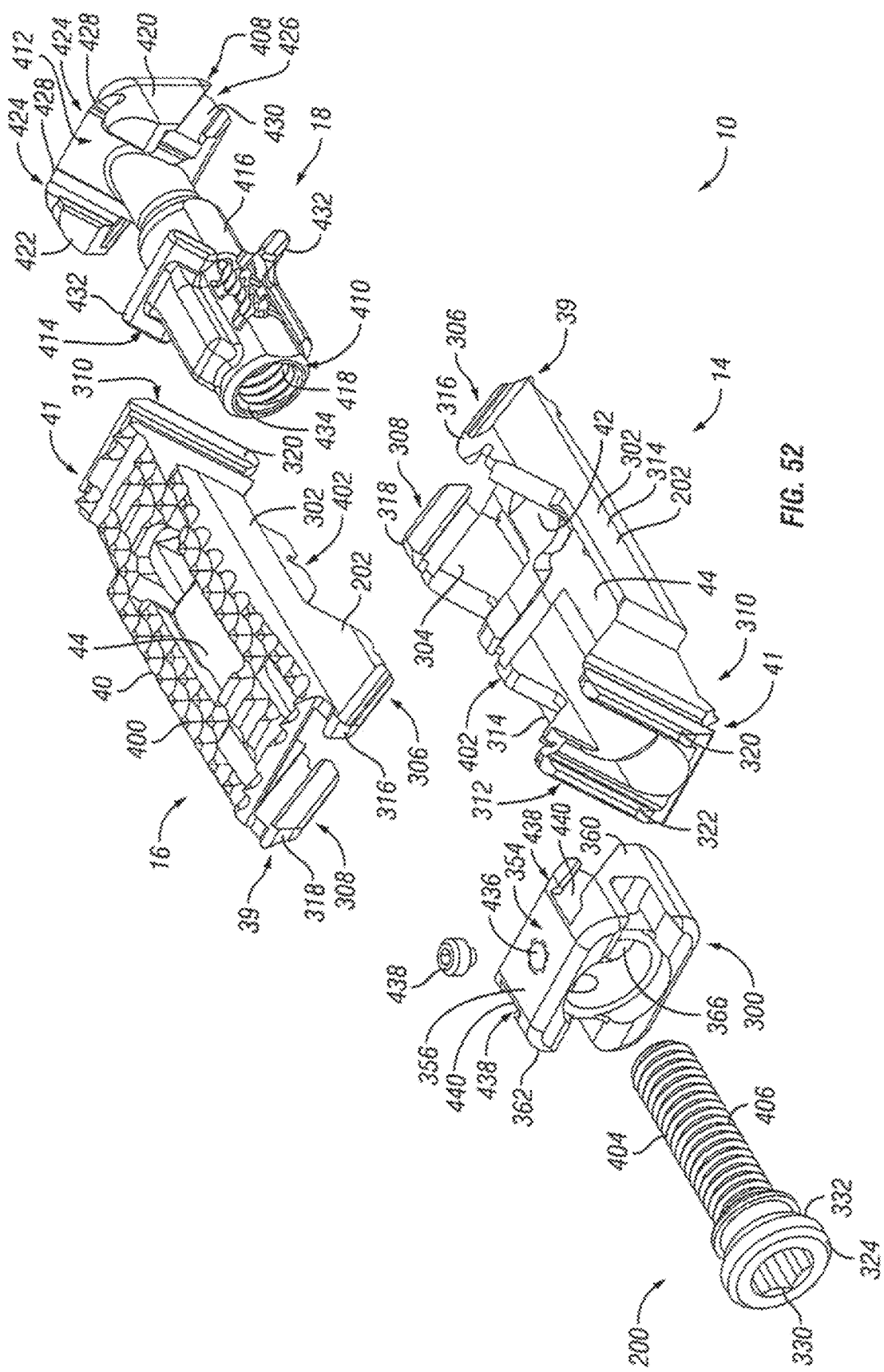
FIG. 52 is an exploded view of the expandable fusion device of FIG. 50 in accordance with one embodiment of the present invention.
Figure 53:
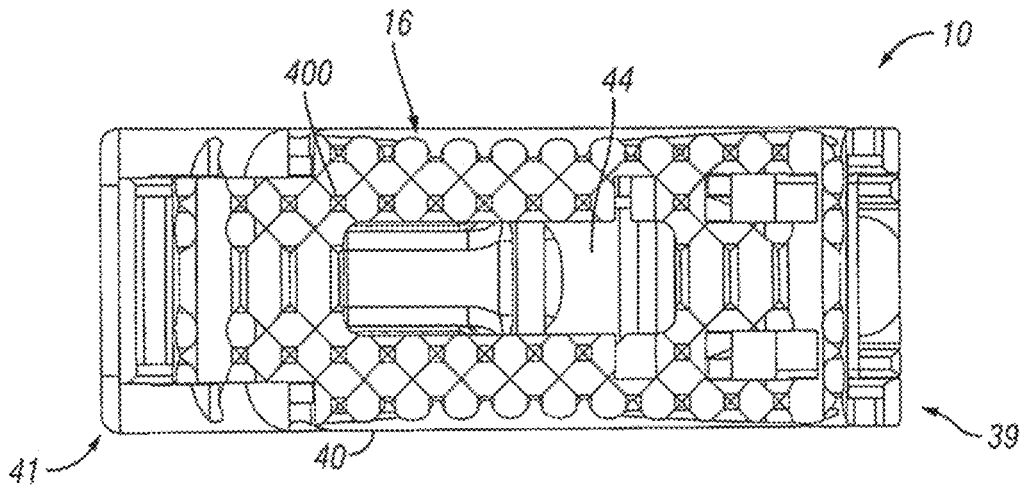
FIG. 53 is a top view of the expandable fusion device of FIG. 50 shown in an unexpanded position in accordance with one embodiment of the present invention.
Figure 56:
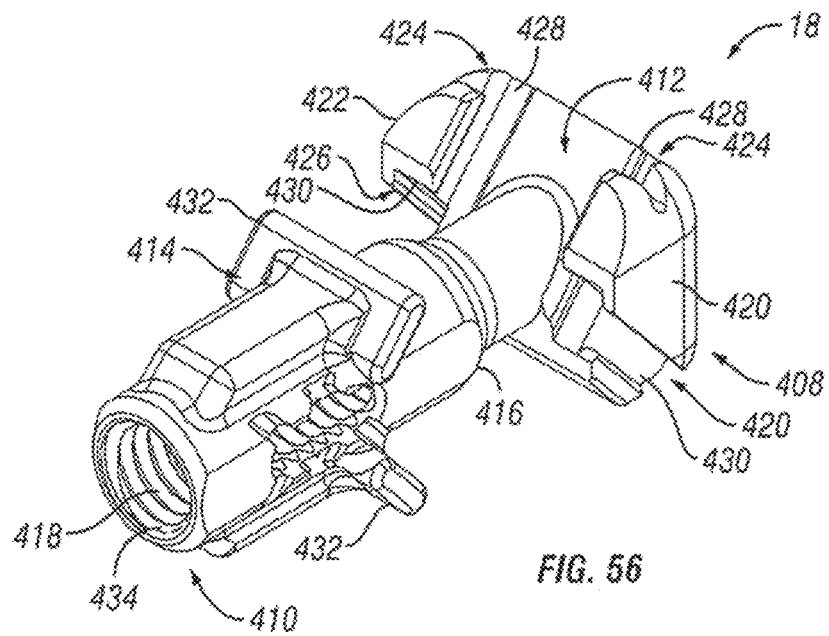
FIG. 56 is a perspective of a central ramp of the expandable fusion device of FIG. 50 in accordance with one embodiment of the present invention.
Figure 57:
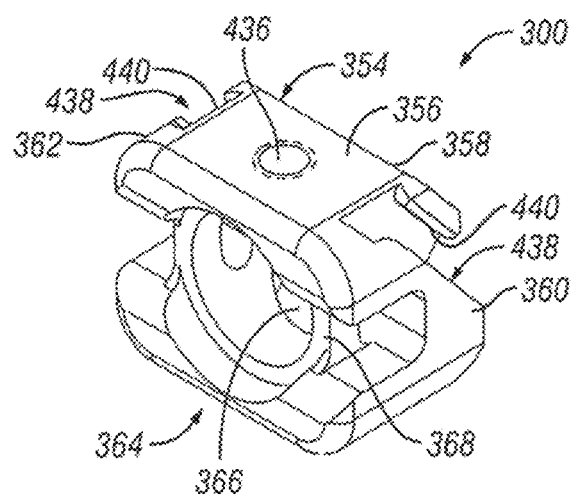
FIG. 57 is a perspective view of a driving ramp of the expandable fusion device of FIG. 50 in accordance with one embodiment of the present invention.

With reference to FIGS. 51, 52, and 56, the central ramp 18 has a first end 408 and a second end 410. In an embodiment, the central ramp 18 includes a first expansion portion 412, a second expansion portion 414, a rod-receiving extension 416, and a through bore 418 that extends longitudinally through the central ramp 18. In an exemplary embodiment, first expansion portion 412 can be proximate the first end 408 of the central ramp 18. As best seen in FIG. 56, the first expansion portion 412 may include side portions 420, 422. In an embodiment, each of the side portions 420, 422 includes dual, overlapping ramped portions that extend in oblique directions with respect to the through bore 418. For example, side portions 420, 422 each include a first ramped portion 424 that overlaps a second ramped portion 426. In the illustrated embodiment, the first ramped portion 424 faces the rod-receiving extension 416 while the second ramped portion 426 faces the opposite direction. In one embodiment, angled grooves 428, 430 are formed in each of the first and second ramped portions 424, 426. In an exemplary embodiment, the angled grooves 428, 430 are sized to receive the corresponding tongues 316, 318, 320, 322 in the first and second endplates 14, 16 with angled grooves 428 receiving tongues 320, 322 in the second endplate 16 and angled grooves 430 receiving tongues 316, 318 in the first endplate 14. Although the device 10 is described with tongues 316, 318, 320, 322 on the endplates 14, 16 and angled grooves 428, 430 on the central ramp 18, it should be understood that that device 10 can also be configured with grooves on the endplates 14, 16 and tongues on the central ramp 18, in accordance with one embodiment of the present invention.

In an embodiment, the second expansion portion 414 is located on the rod-receiving extension 416 between the first end 408 and the second end 410 of the central ramp 18. In an exemplary embodiment, the second expansion portion 414 includes central ramped portions 432. In one embodiment, the second expansion portion 414 includes two central ramped portions 432 on opposite sides of the rod-receiving extension 416. In an exemplary embodiment, the central ramped portions 424 extend in an oblique direction with respect to the through bore 418 and face the second end 410 of the central ramp 18.

The rod-receiving extension 416 extends from the first expansion portion 412 and has an opening 434 at the second end of the central ramp 18. In an embodiment, the rod-receiving extension 416 is sized and configured to receive the extension 404 of the actuator assembly 200. In an embodiment, the rod-receiving extension 416 has threading with the rod-receiving extension 416 threadingly receiving extension 404 of the actuator assembly 200. In another embodiment, the rod-receiving extension 416 has ratchet teeth with the extension 404 being ratcheted into the rod-receiving extension 416.

With reference to FIGS. 50-52 and 57, in an exemplary embodiment, the driving ramp 300 includes an upper portion 354 having an upper surface 356 and an oblique surface 358. In an embodiment, the driving ramp 300 further includes a bore 366, in an exemplary embodiment, sized to receive the extension 404 of the actuator assembly 200. In the illustrated, embodiment, the upper portion 354 has a hole 436 that extends through the upper surface 356 to the bore 366. Set screw 438 may be inserted through the hole 436 to secure the driving ramp 300 to the actuator assembly 200. In one embodiment, the driving ramp 300 further includes contact surface 368 that engages the rim 332 of the head portion 324 of the actuator assembly 200. In the illustrated embodiment, the contact surface 368 has a generally annular shape.

In an embodiment, the driving ramp 300 further includes side portions 360, 362 that extend from the upper portion 354 connecting the upper portion 354 with the lower portion 364 of the driving ramp 300. In an exemplary embodiment, the side portions 360, 362 of the driving ramp 300 each include a ramped portion 438. In the illustrated embodiment, the ramped portion 438 faces central ramp 300. In an embodiment, the ramped portion 438 is configured and dimensioned to engage the ramped portions 306, 308 at the first end 39 of the second endplate 16. In one embodiment, angled grooves 440 are formed in the ramped portions 316, 318. In an exemplary embodiment, the angled grooves 440 are sized to receive the corresponding tongues 316, 318 in the second endplate 16. Although the device 10 is described with tongues 316, 318 on the second endplate 16 and angled grooves 440 on the driving ramp 300, it should be understood that that device 10 can also be configured with grooves on the second endplate 16 and tongues on the driving ramp 300, in accordance with one embodiment of the present invention.

A method of installing the expandable fusion device 10 of FIGS. 50-57 is now discussed in accordance with one embodiment of the present invention. Prior to insertion of the fusion device, the disc space may be prepared as described above. The expandable fusion device 10 can then be inserted into and seated in the appropriate position in the intervertebral disc space. In an embodiment, the device 10 is assembled prior to insertion. The expandable fusion device 10 can be introduced into the intervertebral space, with the end having the first end 408 of the central ramp 18 being inserted. In an exemplary method, the fusion device 10 is in the unexpanded position when introduced into the intervertebral space. In an exemplary method, the intervertebral space may be distracted prior to insertion of the fusion device 10. The distraction provides some benefits by providing greater access to the surgical site making removal of the intervertebral disc easier and making scraping of the endplates of the vertebral bodies 2, 3 easier.

With the fusion device 10 inserted into and seated in the appropriate position in the intervertebral disc space, the fusion device can then expand into the expanded position. To expand the fusion device 10, an instrument is engaged with the head portion 324 of the actuator assembly 200. The instrument is used to rotate actuator assembly 200. As discussed above, actuator assembly 200 is threadingly engaged with the rod receiving extension 416 of the central ramp 18; thus, as the actuator assembly 200 is rotated in a first direction, the central ramp 18 is pulled toward the actuator assembly 200. In an exemplary embodiment, the actuator assembly 200 is moved in a linear direction with the ratchet teeth engaging as means for controlling the movement of the actuator assembly 200 and the central ramp 18.

As the central ramp space 18 is pulled towards the actuator assembly 200, the central ramp 18 acts to push endplates 14, 16 outwardly into the expanded position. By way of example, the first ramped portions 424, second ramped portions 426, and central ramped portions 432 push against the corresponding ramped portions in the first and second endplates 14, 16. The first ramped portions 424 in the first expansion portion 412 of the central ramp 18 push against the second ramped portions 310, 312 of the second endplate 16 with the corresponding tongues 320, 322 in the second ramped portions 310, 312 of the second endplate 16 riding in angled grooves 428 in the first ramped portions 424 in the first expansion portion 412. The second ramped portions 426 in the first expansion portion 412 push against the first ramped portions 316, 318 of the first endplate 14 with the corresponding tongues 316, 318 in first ramped portions 316, 318 of the first endplate 14 riding in angled grooves 430 in the second ramped portions 426 in the first expansion portion 412. The central ramped portions 432 in the second expansion portion 414 push against the central ramped portion 402 in the first and second endplates 14, 16.

As discussed above, the actuator assembly 200 also engages driving ramp 300; thus, as the actuator assembly 200 is rotated in a first direction, the actuator assembly 200 pushes the driving ramp 300 towards the central ramp 18 in a linear direction. As the driving ramp 300 is pushed towards the central ramp 18, the driving ramp 300 also acts to push the endplates 14, 16 outwardly into the expanded position. By way of example, the ramped portions 438 of the driving ramp 300 push against ramped portions 306, 308 at the first end 39 of the second endplate 16. As the endplates 14, 16 move outwardly, the tongues 316, 318 in the ramped portions 306, 308 of the second endplate 16 ride in the angled grooves 440 in the ramped portions 438 of the driving ramp 300.

It should also be noted that the expansion of the endplates 14, 16 can be varied based on the differences in the dimensions of the various ramped portions in the central ramp 18, the driving ramp 300, and the first and second endplates 14, 16. As best seen in FIG. 16, the endplates 14, 16 can be expanded in any of the following ways: straight rise expansion, straight rise expansion followed by a toggle into a lordotic expanded configuration, or a phase off straight rise into a lordotic expanded configuration.

Figure 58:
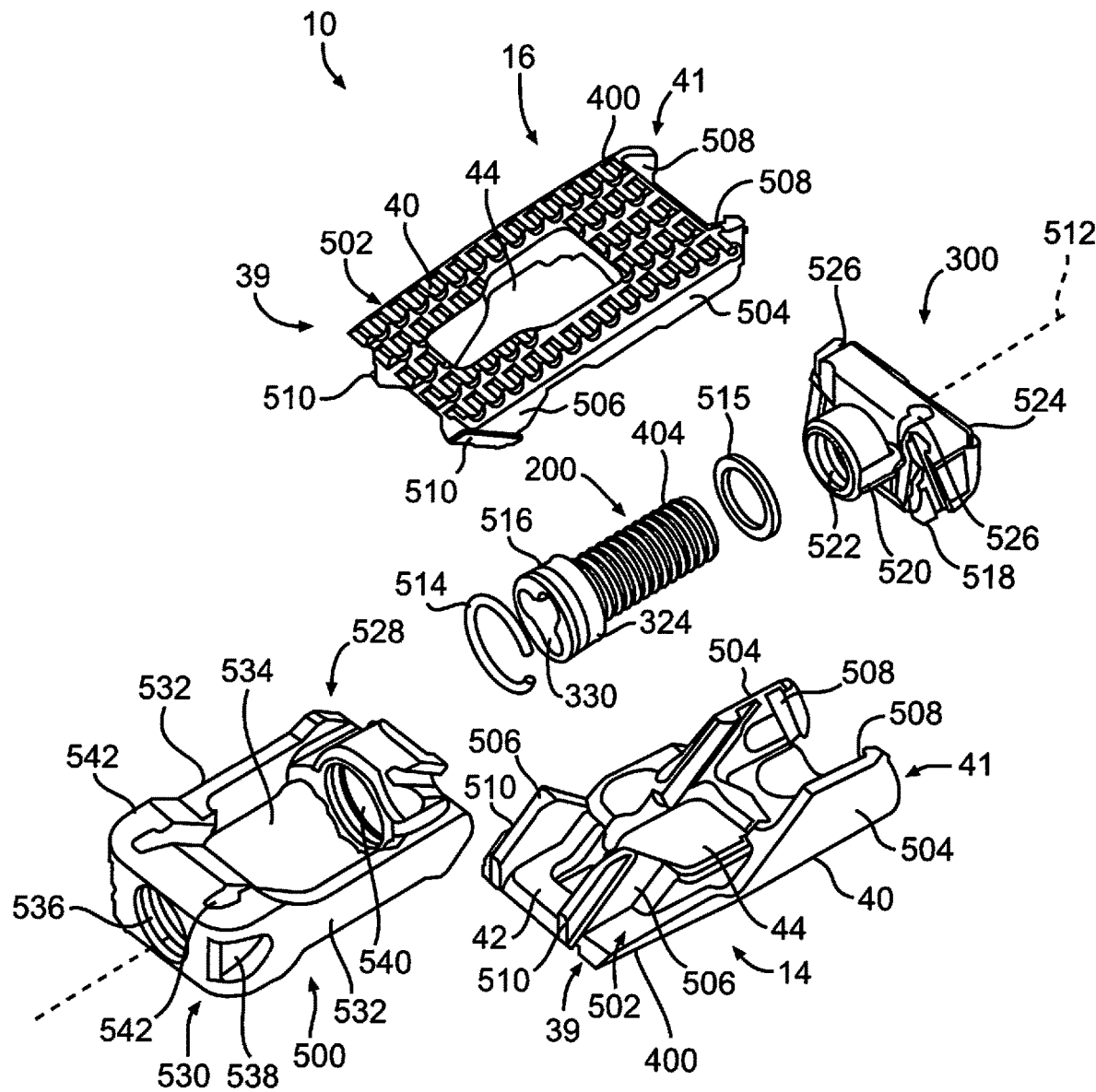
FIG. 58 is an exploded view of an alternative embodiment of an expandable fusion device in accordance with one embodiment of the present invention.
Figure 65:
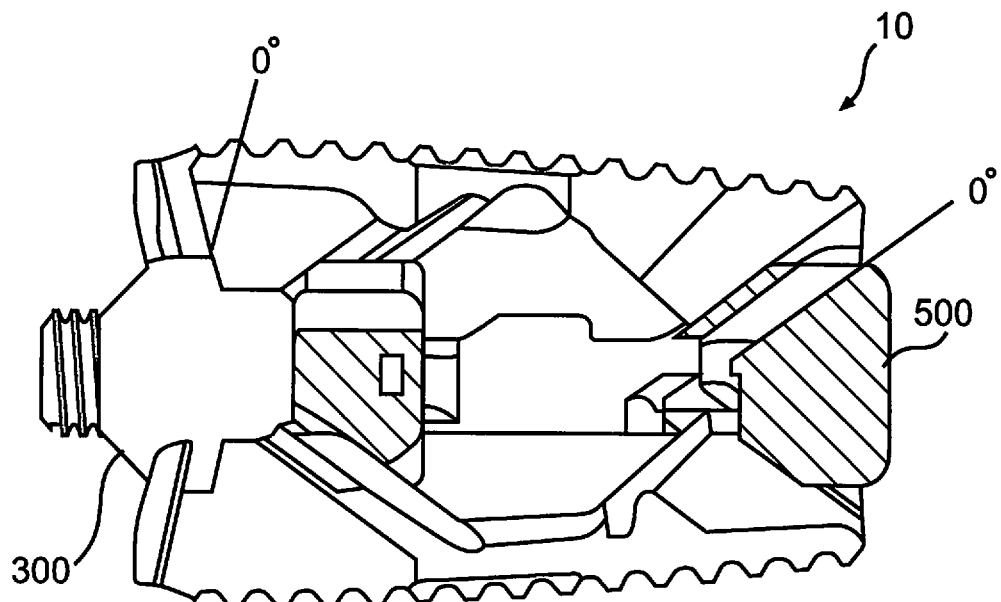
FIG. 65 is a side view of the expandable fusion device of FIG. 58 shown in partial cross-section in a fully expanded configuration in accordance with one embodiment of the present invention.
Figure 66:
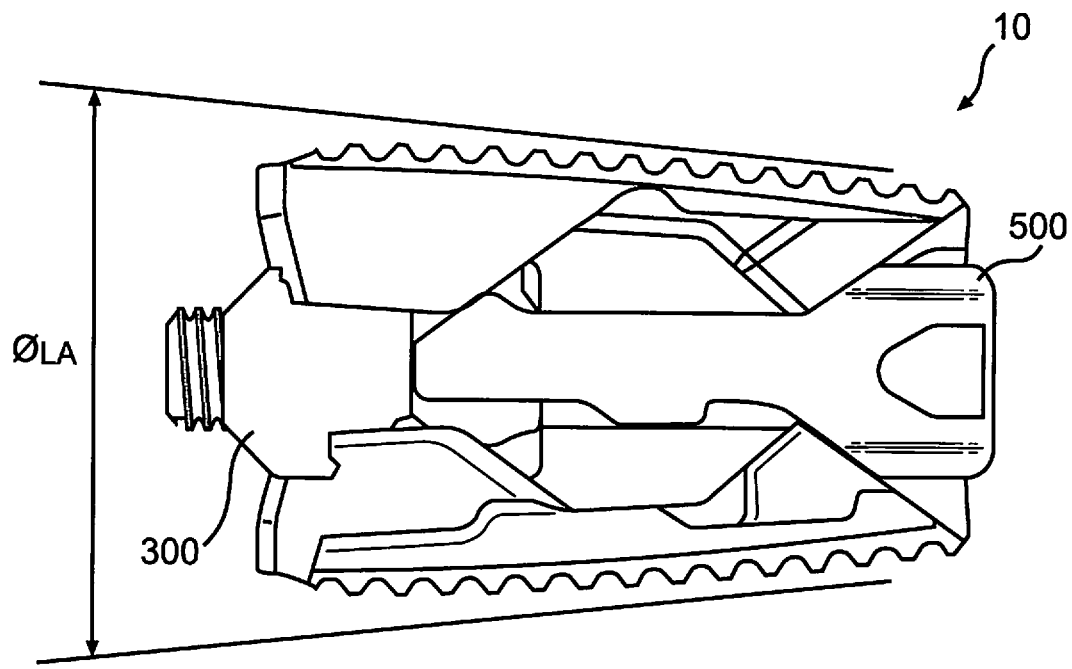
FIG. 66 is a side view of the expandable fusion device of FIG. 58 shown in a fully expanded configuration in accordance with one embodiment of the present invention.
Figure 67:
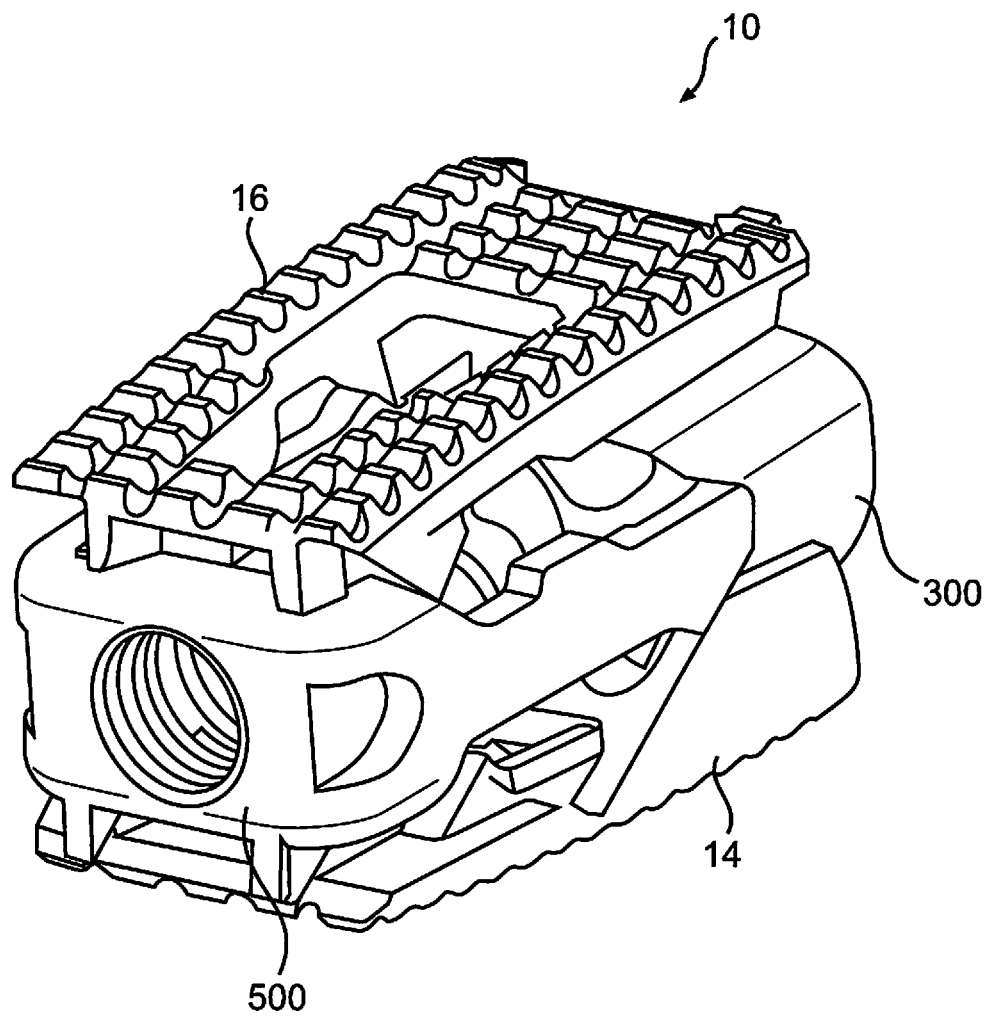
FIG. 67 is a perspective view of the expandable fusion device of FIG. 58 shown in a fully expanded configuration in accordance with one embodiment of the present invention.

Referring now to FIG. 58, an alternative embodiment of the expandable fusion device 10 is shown in which the expandable fusion device 10 expands into a lordotic expanded configuration. In the illustrated embodiment, the expandable fusion device 10 includes a first endplate 14, a second endplate 16, an actuator assembly 200, a driving ramp 300, and a body 500. As will be discussed in more detail below, the actuator assembly 200 functions, in an embodiment, to pull the driving ramp 300 and the body 500 together, which forces apart the first and second endplates 14, 16. For example, the actuator assembly 200 may be rotated to pull the driving ramp 300 toward the body 500. When this occurs, the expandable fusion device 10 first expands into a lordotic expanded configuration (FIGS. 62-64) and then expands in height until it is fully expanded (FIGS. 65-67). In embodiments, expandable fusion device 10 may have two stages of expansion, generally referred to as lordotic stage and parallel stage. In lordotic stage, the expandable fusion device 10 may expand at one end to achieve a lordotic angle. The expandable fusion device 10 may hen expand in parallel sage wherein the lordotic expansion may be maintained at both ends of the expandable fusion device 10 may expand at generally constant rates. In an embodiment, the expandable fusion device 10 may contain features, such as a through bore, that facilitate placement down an endoscopic tube. In an embodiment, the assembled fusion device 10 may be placed down the endoscopic tube and then expanded.

Although the following discussion relates to the first endplate 14, it should be understood that it also equally applies to the second endplate 16 as the second endplate 16 is substantially identical to the first endplate 14 in embodiments of the present invention. It should be understood that, in an embodiment, the first endplate 14 is configured to interlock with the second endplate 16. In an exemplary embodiment, the first endplate 14 has a first end 39 and a second end 41. In the illustrated embodiment, the first endplate 14 further comprises a plate portion 502 that may extend between first end 39 and the second end 41. Plate portion 502 may comprise an upper surface 40 and a lower surface 42. In an embodiment, the first endplate 14 may comprise a through opening 44. The through opening 44, in an exemplary embodiment, may be sized to receive bone graft or similar bone growth inducing material.

In one embodiment, the upper surface 40 of the plate portion 502 is flat and generally planar to allow the upper surface 40 of the plate portion 502 to engage with the adjacent vertebral body 2. Alternatively, as shown in FIG. 15, the upper surface 40 can be curved convexly or concavely to allow for a greater or lesser degree of engagement with the adjacent vertebral body 2. It is also contemplated that the upper surface 40 can be generally planar but includes a generally straight ramped surface or a curved ramped surface. The ramped surface allows for engagement with the adjacent vertebral body 2 in a lordotic fashion. As illustrated, in an exemplary embodiment, the upper surface 40 includes texturing to aid in gripping the adjacent vertebral bodies. For example, the upper surface 40 may further comprise texturing 400 to engage the adjacent vertebral bodies. Although not limited to the following, the texturing can include teeth, ridges, friction increasing elements, keels, or gripping or purchasing projections.

In one embodiment, the first endplate 14 further comprises front side extensions 504 that extend from plate portion 502. As illustrated, the front side extensions 504 may extend from either side of plate portion 502 proximate to second end 41 of first endplate 14. The front side extensions 504 may extend opposite from the upper surface 40 of plate portion 502. In one embodiment, the first endplate 14 may further comprise rear side extensions 506 that extend from plate portion 502. As illustrated, the rear side extensions 506 may extend from either side of plate portion 502 proximate to first end 39 of first endplate 14. The rear side extensions 506 may extend opposite from the upper surface 40 of plate portion 502. As illustrated, the front side extensions 504 and the rear side extensions 506 may each include ramped portions. For example, the front side extension 504 may include front ramped portions 508 and the rear side extensions 506 may include rear ramped portions 510. The front ramped portions 508 and the rear ramped portions 510 may be considered ramped as they may be at an oblique angle with respect to longitudinal axis 512 of expandable fusion device 10. In an exemplary embodiment, the front ramped portions 508 may generally face the second end 41, and the rear ramped portions 510 may generally face the first end 39.

Embodiments of actuator assembly 200 will now be described in more detail with reference to FIG. 58. In the illustrated embodiment, the actuator assembly 200 is in the form of a drive screw. As illustrated, the actuator assembly 200 may include a head portion 324 and an extension 404. As illustrated, the head portion 324 may include one or more instrument gripping features 330 that can allow it to be turned by a suitable instrument. In addition, the head portion 324 may have a larger diameter than the other components of the actuator assembly 200 to provide a contact surface with the body 500. In the illustrated embodiment, ring 514 may ride in groove 516 on head portion 324. In some embodiments, ring 514 may be a compressible ring, such as a c-ring as shown on FIG. 58, that is configured to retain head portion 324 in rear throughbore 536 of body 500. In an embodiment, the extension 404 is a generally rod-like extension that may be threaded for engaging a corresponding opening 522 in driving ramp 300. In another embodiment, the extension 404 may include ratchet teeth (not shown) for engaging opening 522 in driving ramp 300.

Embodiments of driving ramp 300 will now be described in more detail with respect to FIG. 58. As illustrated, the driving ramp 300 may include a ramped body portion 518 and an extension 520. In the illustrated embodiment, extension 520 may extend from ramped body portion 518 toward first end 39 of expandable fusion device 10. Extension 520 may include an opening 522 that may engage extension 404 of actuator assembly 200. In embodiments, extension 520 may threadingly engage the extension 404 of actuator assembly 200. Rotation of driving ramp 300 may be limited so that when actuator assembly 200 may be rotated, driving ramp 300 may be pulled toward body 500. Driving ramp 300 may be secured to actuator assembly 200 at a front end of expandable fusion device 10. In embodiments, the front end of expandable fusion device 10 may be the front of the expandable fusion device 10 so that the driving ramp 300 may be considered the nose of the expandable fusion device 10. In embodiments, the front end 524 of driving ramp 300 may be angled, rounded, or otherwise tapered so that the driving ramp may serve to distract the adjacent vertebral bodies when the expandable fusion device 10 is inserted into an intervertebral space.

As illustrated, driving ramp 300 may include front endplate engaging ramps 526. Front endplate engaging ramps 526 may be at an oblique angle with respect to longitudinal axis 512 of the expandable fusion device 10. As illustrated, a pair of front endplate engaging ramps 526 that engage second endplate 16 may be on one side of driving ramp while another pair of front endplate engaging ramps 526 that engage first endplate 14 may be on an opposite side of driving ramp 300. In operation, front endplate engaging ramps 526 may engage front ramped portions 508 of the first and second endplates 14, 16. The first and second endplates 14, 16 may ride up the front endplate engaging ramps 526 as the driving ramp 300 may be pulled towards the body 300 causing the first and second endplates 14, 16 to be pushed relatively apart such that a height of expandable fusion device 10 may be increased.

Embodiments of body 500 will now be described in more detail with respect to FIG. 58. As illustrated, the body 500 may have a first body end 528 and a second body end 530. Lateral sides 532 may connect the first body end 528 and the second body end 530. In the illustrated embodiment, the body 500 may have a central opening 534 that may extend through the body 500 transverse to longitudinal axis 512 of expandable fusion device. As illustrated, first body end 528, second body end 530, and lateral sides 532 may define central opening 534. Rear throughbore 536 may be formed through second body end 530. Rear throughbore 536 may be centrally positioned and generally aligned with longitudinal axis 512 of expandable fusion device 10. As previously described, head portion 324 of actuator assembly 200 may be retained in rear throughbore 536, for example, using ring 514. Washer 515 may also be retained on corresponding grooves of head portion 324. Rear throughbore 506 may also be threaded, for example, to facilitate engagement with an insertion device. Second body end 530 may also include tool engaging features, such as side recesses 538, which may facilitate use of a device for insertion of expandable fusion device 10 into a desired position in a patient. First body end 528 may include a corresponding front throughbore 540. As illustrated, front throughbore 540 may be centrally positioned and generally aligned with longitudinal axis 512 of expandable fusion device. Extension 404 of actuator assembly 200 may extend through front throughbore 540 to engage driving ramp 300.

As illustrated, second body end 530 may include rear endplate engaging ramps 542. Rear endplate engaging ramps 542 may be at an oblique angle with respect to longitudinal axis 512 of the expandable fusion device 10. In operation, rear endplate engaging ramps 542 may engage rear ramped portions 510 of the first and second endplates 14, 16. As illustrated, a pair of rear endplate engaging ramps 542 that engage second endplate 16 may be on one side of second body end 530 while another pair of rear endplate engaging ramps 542 (not seen on FIG. 58) that engage first endplate 14 may be on an opposite side of second body 530. The first and second endplates 14, 16 may ride up the rear endplate engaging ramps 542 as the driving ramp 300 may be pulled towards the body 300 causing the first and second endplates 14, 16 to be pushed relatively apart such that a height of expandable fusion device 10 may be increased.

As previously described, the expandable fusion device 10 shown on FIG. 58 may first expand lordotically and then expand in parallel until full expansion of the expandable fusion device 10 may be reached. To achieve this lordotic expansion, the front ramped portions 508 and rear ramped potions 510 of the first and second endplates 14, 16 may be at a different angle with respect to longitudinal axis 512 than the front endplate engaging ramps 526 of the driving ramp 300 and the rear endplate engaging ramps 542 of the body 500. This difference in angles may be present when the expandable fusion device 10 is in the unexpanded configuration. As the driving ramp 300 may be pulled back towards the body 500, the position of the first and second endplates 14, 16 and/or the driving ramp 300 and the body 500 with respect to body 500 may change so that the difference in angles may be reduced and potentially approach zero as the first and second endplates 14, 16 are pushed outward. As this angle is being reduced, the rear portion of the expandable fusion device may be expanding causing a lordotic angle. When this angle is reduced (or reaches approximately zero), the first and second endplates 14, 16 may then expand in parallel with the first end 39 and second end 41 expanding at approximately the same height until the expandable fusion device 10 may reach its full height. The lordotic angle may be maintained while the first and second endplates 14, 16 expand in parallel.

Figure 59:
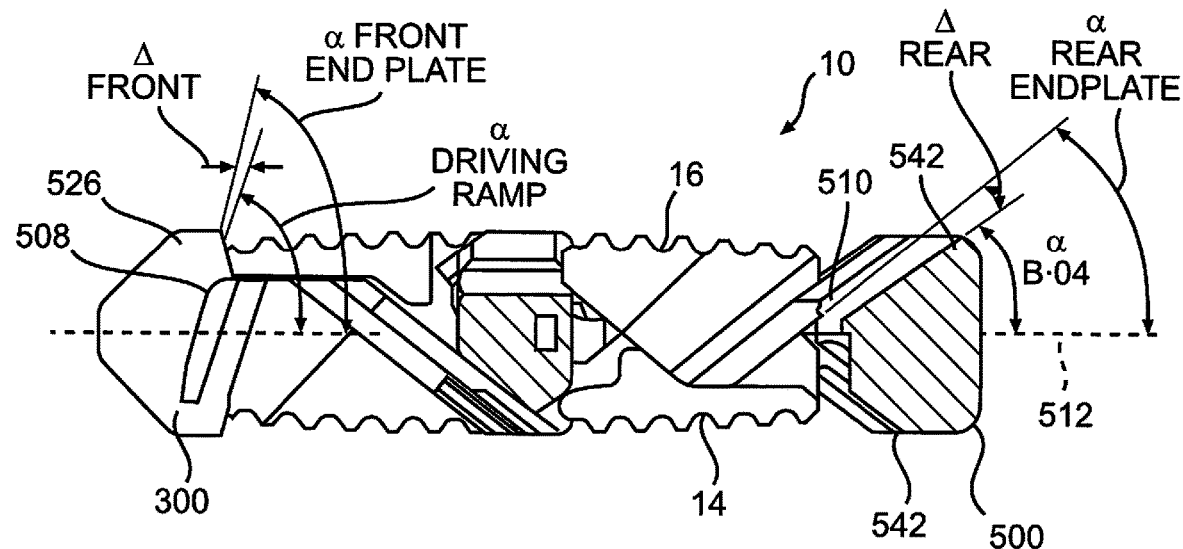
FIG. 59 is a side view of the expandable fusion device of FIG. 58 shown in partial cross-section in an unexpanded configuration in accordance with one embodiment of the present invention.
Figure 60:
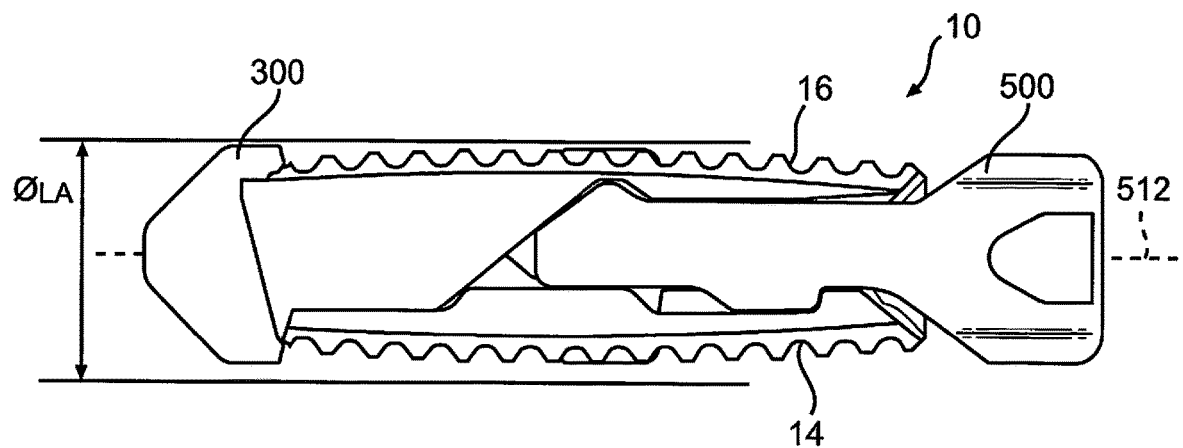
FIG. 60 is a side view of the expandable fusion device of FIG. 58 shown in an unexpanded configuration in accordance with one embodiment of the present invention.
Figure 61:
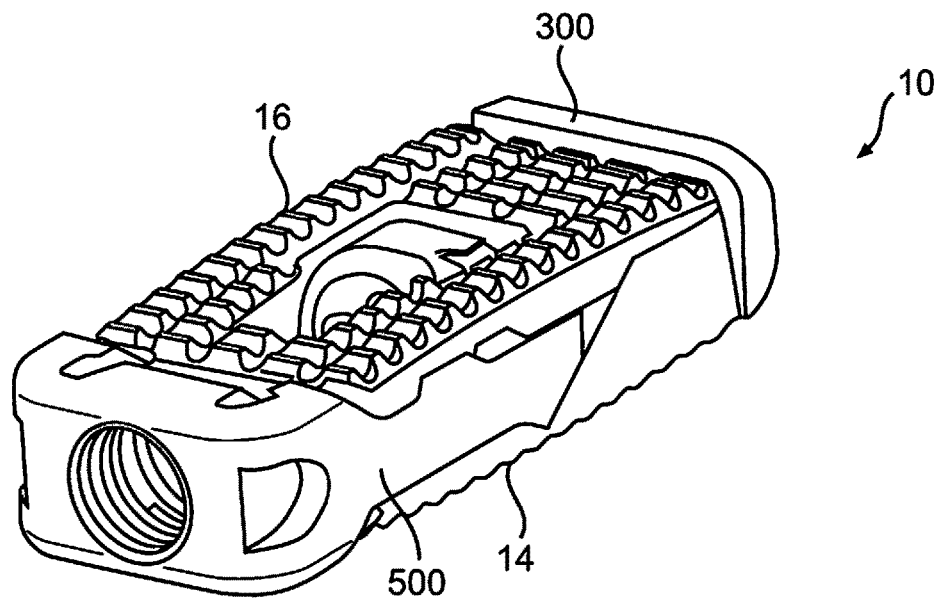
FIG. 61 is a perspective view of the expandable fusion device of FIG. 58 shown in an unexpanded configuration in accordance with one embodiment of the present invention.

FIGS. 59 to 61 illustrate the expandable fusion device 10 in the unexpanded configuration in accordance with present embodiments. As seen on FIG. 60, the expandable fusion device 10 may have a lordotic angle $\theta_{LA}$ of approximately 0° when unexpanded. By way of example, the first and second endplates 14, 16 may be generally aligned with longitudinal axis 512 of expandable fusion device 10. In accordance with present embodiments, lordotic expansion of expandable fusion device 10 may be achieved by use of different in ramp angles with respect to longitudinal axis 512. As best seen on FIG. 59, rear endplate engaging ramps 542 of the body 500 may have an angle $\alpha_{body}$ and rear ramped portions 510 of first and second endplates 14, 16 may have an angle $\alpha_{rearendplate}$. The front endplate engaging ramps 526 of the driving ramp 300 may have an angle $\alpha_{driving}$ ramp and the front ramped portions 508 of the first and second endplates 14, 16 may have an angle $\alpha_{frontendplate}$. These angles may be selected, for example, to provide a desired rate of height increase during expansion of expandable fusion device 10. By way of example, the angles may each individually by selected, for example, from about 5° to about 85° and alternatively from about 35° to about 65°. However, as described above, embodiments may provide differences in these angles, for example, to drive the lordotic expansion. As best seen on FIG. 59, the difference between the angles $\alpha_{rearendplate}$ and $\alpha_{body}$ may be provided by $\Delta_{rear}$, and the difference between the angles $\alpha_{frontendplate}$ and $\alpha_{driving\ ramped}$ may be provided by $\Delta_{front}$. $\Delta_{rear}$ and $\Delta_{front}$ may be the same or different. By way of example, $\Delta_{rear}$ and $\Delta_{front}$ may each range from 1° to about 20° and, alternatively, from about 2° to about 5°.

Figure 62:
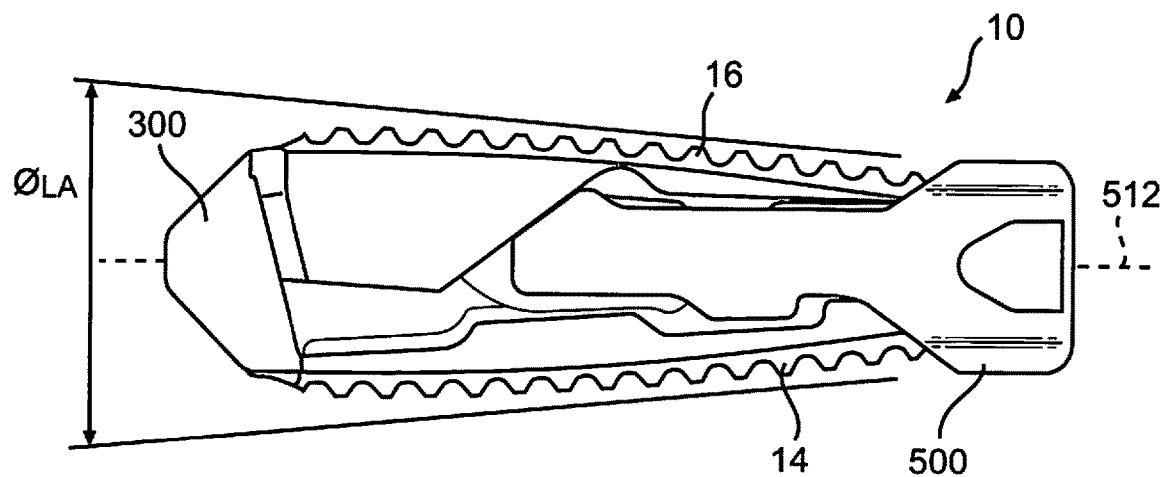
FIG. 62 is a side view of the expandable fusion device of FIG. 58 shown in partial cross-section in a lordotic expanded configuration in accordance with one embodiment of the present invention.
Figure 63:
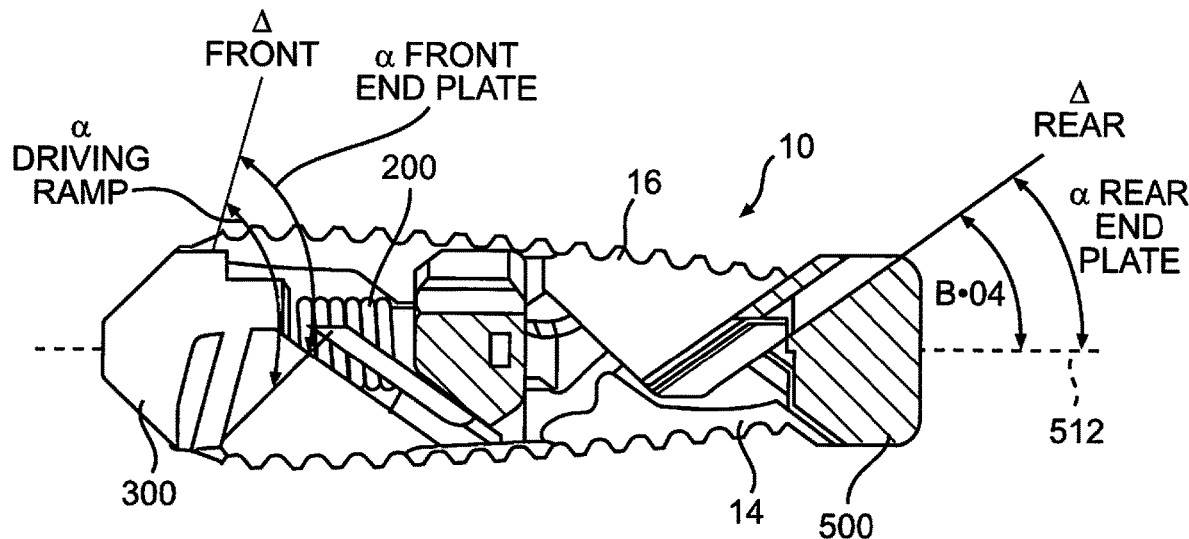
FIG. 63 is a side view of the expandable fusion device of FIG. 58 shown in a lordotic expanded configuration in accordance with one embodiment of the present invention.
Figure 64:
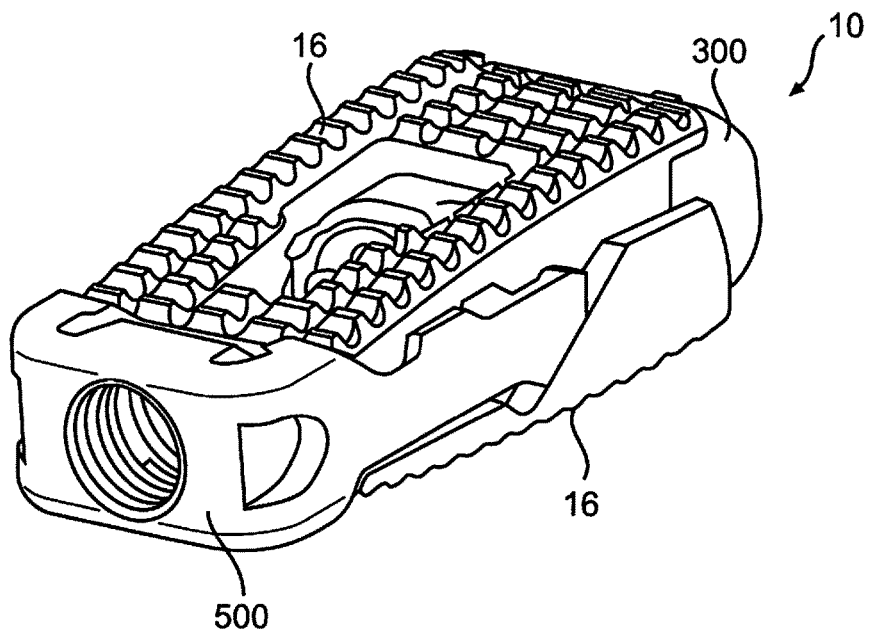
FIG. 64 is a perspective view of the expandable fusion device of FIG. 58 shown in a lordotic expanded configuration in accordance with one embodiment of the present invention.

FIGS. 62 to 64 illustrate the expandable fusion device 10 in a lordotic expanded configuration in accordance present embodiments. The expandable fusion device 10 may be expanded to provide a lordotic angle $\theta_{LA}$ of up to about 15° and, more particularly, of about 4° to about 10°. Lordotic angles $\theta_{LA}$ of up to 12° may be desired in certain applications, such as cervical, but other lordotic angles $\theta_{LA}$ may be desired in alternative applications.

To expand the expandable fusion device 10, driving ramp 300 may be moved in a first direction with respect to body 500. By way of example, driving ramp 300 may be pulled towards body 500. In some embodiments, actuator assembly 200 (best seen on FIG. 58) may be rotated to pull driving ramp 300 towards body 500. As driving ramp 300 may be pulled towards body 500, the driving ramp 300 and body 500 may engage the first and second endplates 14, 16. By way of example, the front ramped portions 508 of the first and second endplates 14, 16 may engage the front endplate engaging ramps 526 of the driving ramp 300 and the rear ramped portions 510 of the first and second endplates 14, 16 may engage the rear endplate engaging ramps 542 of the body 500. However, because of the difference in ramp angles (shown as $\Delta_{rear}$ and $\Delta_{front}$ on FIG. 59), the first and second endplates 14, 16 may not ride up the front endplate engaging ramps 526 and the rear endplate engaging ramps 542 to increase the height of the expandable fusion device. Instead, in some embodiments, the first and second endplates 14, 16 may pivot at the contact point between the first and second endplates 14, 16 and the body 500 causing expansion of the endplates 14, 16 at the opposite end. As seen in FIGS. 62-64, this pivoting may result in expansion of the first and second endplates 14, 16 into an expanded lordotic configuration. As will be appreciated, pivoting of the first and second endplates 14, 16 may cause the angles $\alpha_{rearendplate}$ and $\alpha_{frontendplate}$ with respect to longitudinal axis 512 to change, thus reducing the difference in ramp angles $\Delta_{rear}$, $\Delta$front. When the difference in ramp angles $\Delta_{rear}$, $\Delta_{front}$ approaches 0° (e.g., within 0.5°, 0.1°, or less), lordotic expansion may stop, and expandable fusion device 10 may be in its lordotic expanded configuration.

FIGS. 65 to 67 illustrate expandable fusion device 10 in a fully expanded configuration, in accordance with present embodiments. In some embodiments, it may be desired to further expand the expandable fusion device 10 from the lordotic expanded configuration of FIGS. 62-64. By way of example, continued movement of driving ramp 300, for example, translational movement towards body 500, may cause further expansion of expandable fusion device 10. This further expansion may be considered parallel expansion as both ends of the expandable fusion device 10 may expand at the same rate. Expansion may be continued, for example, until the expandable fusion device 10 has reached its fully expanded configuration or until a desired height of expandable fusion device 10 has been achieved. Expansion of expandable fusion device 10 may be limited by engagement of driving ramp 300 with body 500.

In the event the fusion device 10 needs to be repositioned or revised after being installed and expanded, the fusion device 10 can be contracted back to the unexpanded configuration, repositioned, and expanded again once the desired positioning is achieved. To contract the fusion device 10, an instrument can be used to rotate the actuator assembly 200 in a second direction that is opposite the first direction. Rotation of the actuator assembly 200 in the opposite direction may result in movement of the body 500 and the driving ramp 300 away from one another. As the body 500 and driving ramp 300 move away from one another, the endplates 14, 16 move inwardly into the unexpanded position.

Expanded heights of expandable fusion device 10 may typically range from 7 mm to 12 mm, but may be larger or smaller, including as small as 5 mm, and as large as 16 mm, although the size is dependent on the patient, and the joint into which the expandable fusion device 10 may be implanted. Expandable fusion device 10 may be implanted within any level of the spine, and may also be implanted in other joints of the body, including joints of the hand, wrist, elbow, shoulder, hip, knee, ankle, or foot.

Although the preceding discussion only discussed having a single fusion device 10 in the intervertebral space, it is contemplated that more than one fusion device 10 can be inserted in the intervertebral space. It is further contemplated that each fusion device 10 does not have to be finally installed in the fully expanded state. Rather, depending on the location of the fusion device 10 in the intervertebral disc space, the height of the fusion device 10 may vary from unexpanded to fully expanded. It should be noted that, as well as the height being varied from an unexpanded state to an expanded state, the fusion 10 may be positioned permanently anywhere between the expanded state and the unexpanded state.

In some embodiments, an expandable fusion device can be provided whereby expansion is performed via a ratcheting mechanism. By providing a ratcheting mechanism, this advantageously provides for rapid, convenient, non-continuous expansion of the fusion device.

Figure 68:
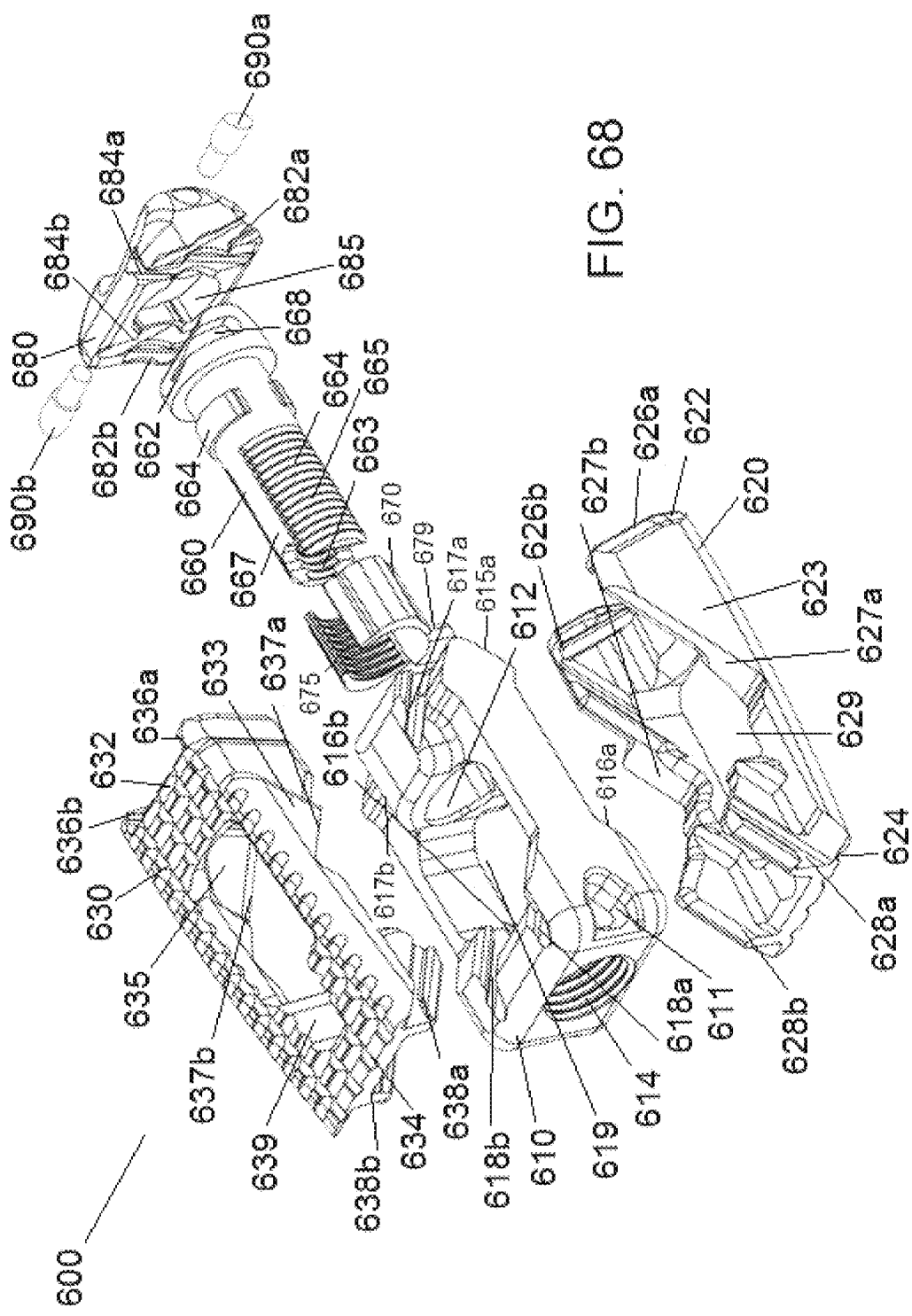
FIG. 68 is an exploded view of an expandable fusion device having a ratcheting mechanism in accordance with some embodiments.

FIG. 68 is an exploded view of an expandable fusion device having a ratcheting mechanism in accordance with some embodiments. The expandable fusion device 600 comprises a first endplate 620, a second endplate 630, a body 610 positioned between the first endplate 620 and the second endplate 630, a stem 660 and associated collar 670, and a nose 680. The stem 660 and associated collar 670 advantageously provide a non-continuous ratcheting mechanism to the expandable fusion device, whereby the expandable fusion device can alternatingly incrementally increase and then stop, until a desired expansion occurs.

The first endplate 620 comprises a lower endplate having a first end 622 and a second end 624. The first end 622 comprises a pair of first end ramped portions 626a, 626b. Each of these ramped portions 626a, 626b is configured to engage corresponding lower nose ramps 682a, 682b on the nose 680 to aid with expansion of the expandable fusion device. The second end 624 comprises a pair of second end ramped portions 628a, 628b. Each of these ramped portions 628a, 628b is configured to engage corresponding rear lower ramps 616a, 616b on the body 610 to aid with expansion of the expandable fusion device. A first side portion 623 having a central ramp 627a and a second side portion 625 having a central ramp 627b are positioned between the first end 622 and the second end 624 of the first endplate 620. Each of the central ramps 627a, 627b is configured to engage corresponding front lower ramps 615a, 615b (not visible) of the base 610 to aid with expansion of the expandable fusion device. The ramps of the first endplate 620 are formed along a perimeter that surrounds a central opening 629.

The second endplate 630 comprises an upper endplate having a first end 632 and a second end 634. The first end 632 comprises a pair of first end ramped portions 636a, 636b. Each of these ramped portions 636a, 636b is configured to engage corresponding upper nose ramps 684a, 684b on the nose 680 to aid with expansion of the expandable fusion device. The second end 634 comprises a pair of second end ramped portions 638a, 638b. Each of these ramped portions 638a, 638b is configured to engage corresponding rear upper ramps 618a, 618b on the body 610 to aid with expansion of the expandable fusion device. A first side portion 633 having a central ramp 637a and a second side portion 635 having a central ramp 637b are positioned between the first end 632 and the second end 634 of the second endplate 630. Each of the central ramps 637a, 637b is configured to engage corresponding front upper ramps 617a, 617b of the base 610 to aid with expansion of the expandable fusion device. The ramps of the second endplate 630 are formed along a perimeter that surrounds a central opening 639.

The body 610 comprises a front throughbore 612 and a rear throughbore 614. The front throughbore 614 comprises an opening for receiving the collar 670, and hence the stem 660, therethrough. The rear throughbore 614 comprises an opening through which one or more tools (e.g., an expansion tool and a disengagement tool) can pass through, as shown in FIGS. 78B and 78D. In some embodiments, the rear throughbore 614 is threaded to allow engagement by an insertion tool. In addition, the body 610 comprises one or more tool recesses 611 that can be engaged by an insertion tool to provide easy delivery of the implant into a surgical site. As shown in FIG. 68 and discussed above, the body 610 comprises a number of angled surfaces or ramps that are configured to engage corresponding ramps on the first endplate 620 or second endplate 630. As the ramps slide against one another, this causes expansion of the expandable fusion device.

The stem 660 and associated collar 670 form a ratcheting mechanism for causing expansion of the expandable fusion device. The stem 660 comprises a head 662 and a shaft 664. The stem 660 (via its head 662) is receivable within the nose 680 of the implant, whereby it is capable of rotation. In some embodiments, rotation of the stem 660 causes the implant to be changed from a "locked" ratcheting configuration into a "disengaged" non-ratcheting configuration, as will be discussed further below. The head 662 of the stem 660 comprises one or more grooves or slots 668 for receiving one or more nose pins 690*a*, 690*b* that extend through the nose 680. The shaft 664 of the stem 660 comprises an elongate body having an opening 663 for receiving an expansion tool 710 (shown in FIG. 78C) therethrough. The stem 660 further comprises ratchet teeth 665 that extend along a length of the shaft 664. In addition, the stem 660 comprises one or more flat areas 667 that are positioned adjacent to the ratchet teeth 665. In some embodiments, the stem 660 comprises a pair of flat areas 667 that are positioned 180 degrees apart from one another. In some embodiments, the stem 660 comprises a half ring portion 664 that is advantageously designed to hit against the body 610 at full expansion in order to prevent over expansion of the device.

The stem 660 is capable of two configurations. In a first "locked" configuration (shown in FIG. 78D), the ratchet teeth 665 of the stem 660 are engaged with corresponding ratchet recesses 675 of the collar 670, thereby creating a ratcheting mechanism that provides for expansion of the implant 600. In a second "disengaged" configuration (shown in FIG. 78E), the stem 660 is rotated such that the one or more flat areas 667 are positioned adjacent the ratchet recesses 675, such that the ratcheting mechanism is not operable. In this second disengaged configuration, the stem 660 is capable of being pulled back, thereby causing contraction of the implant 600.

The stem 660 is insertable through the collar 670, whereby it is placed in either the "locked" ratcheting configuration or the "disengaged" non-ratcheting configuration. In some embodiments, the collar 670 comprises a C-shaped ring having inner ratchet recesses 675 formed along an inner wall. In some embodiments, the collar 670 is housed within the front throughbore 616 of the body 610. In some embodiments, the collar 670 comprises a compressible C-ring type body that is capable of compression within the front throughbore 616. In some embodiments, the collar 670 is not rotatable, and can be keyed into place to prevent rotation. Advantageously, the collar 670 can comprise a tab 679 that prevents rotation of the collar 670 within the body 610. With the stem 660 attached to the collar 670, a ratcheting mechanism is formed whereby an expansion tool 710 (shown in FIG. 78C) can extend through the collar 670 and into the stem 660 via the shaft opening 663. The expansion tool 710 is capable of pulling or ratcheting the stem 660 in a direction towards the second ends of the first endplate 620 and second endplate 630. As the stem 660 is operably connected to the nose 680, the nose 680 is also drawn, thereby causing ramps of the first endplate 620 and second endplate 630 to slide up corresponding ramps of the body 610 and nose 680.

The nose 680 comprises a throughhole 685 through which the head 662 of the stem 660 can extend therethrough. A pair of nose pins 682*a*, 682*b* can then extend through the nose 680 and into the head 662, thereby retaining the stem 660 in the nose 680. As noted above, the nose 680 comprises one or more upper nose ramps 684*a*, 684*b*, which are configured to mate and engage corresponding ramps on the second endplate 630. In addition, the nose 680 comprises one or more lower nose ramps 682*a*, 682*b*, which are configured to mate and engage corresponding ramps on the first endplate 620.

Figure 69C:
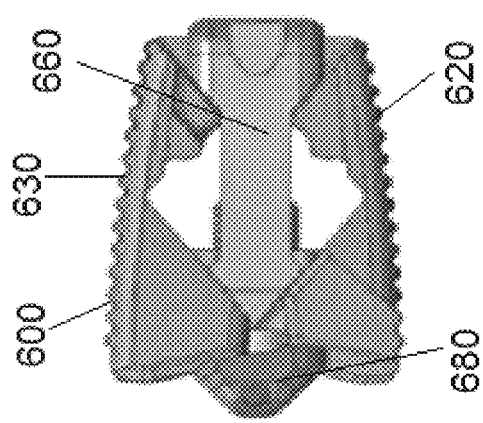
FIGS. 69A-69C are side views of the expandable fusion device of FIG. 68 in the process of expansion in accordance with some embodiments.
Figure 69B:
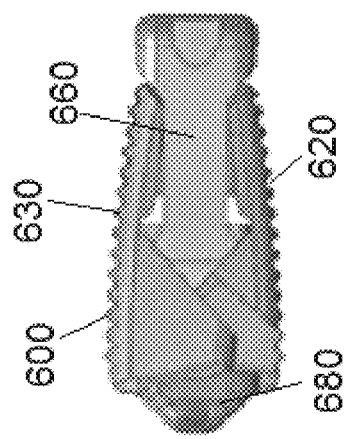
Figure 69A:
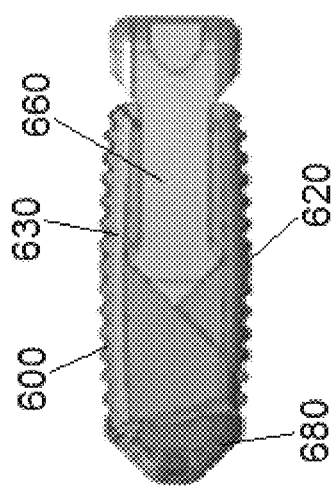

FIGS. 69A-69C are side views of the expandable fusion device of FIG. 68 in the process of expansion in accordance with some embodiments. In some embodiments, the expandable fusion device 600 is advantageously capable of expansion, and in particular, lordotic expansion. In some embodiments, the device 600 can begin in a contracted state, as shown in FIG. 69A. Afterwards, by pulling the nose 680 via a ratcheting mechanism, the device 600 can expand and tip into lordosis, as shown in FIG. 69B. Once the device 600 has achieved maximum lordosis, the device 600 can continue to expand in height in a parallel fashion, whereby both the anterior and posterior aspects expand at the same rate, until the implant 600 reaches a maximum expansion, as shown in FIG. 69C. In other words, once the device 600 reaches a particular lordotic angle (as shown in FIG. 69B), the device 600 will maintain the lordotic angle throughout the expansion range until maximum expansion has been achieved, as shown in FIG. 69C. More details on the expansion of the device 600 are provided with respect to FIGS. 70A-72C.

Figure 70A:
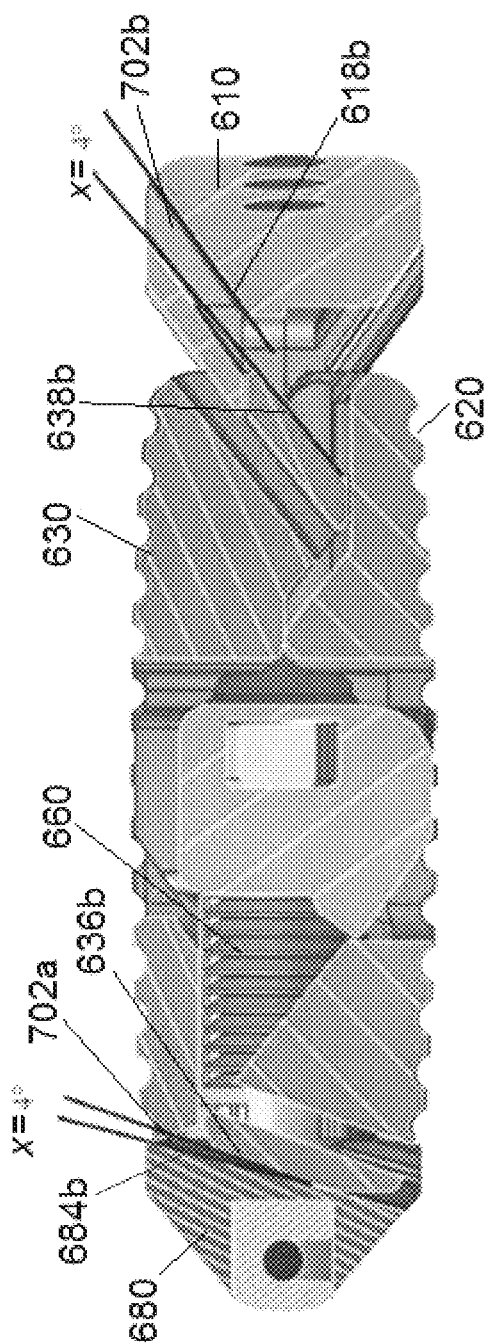

FIGS. 70A-70C are different views of the expandable fusion device of FIG. 68 in a contracted state in accordance with some embodiments. From the contracted state, the device 600 is capable of first expanding and tipping into lordosis, and then expanding in a parallel fashion. The angle tipping is driven by a difference in ramp angle x that is seen between the first end ramped portions 636*a*, 636*b* of the second endplate 630 and the upper nose ramps 684*a*, 684*b* of the nose 680. Similarly, the same difference in ramp angle x is also seen between the second end ramped portions 638*a*, 638*b* of the second endplate 630 and the rear upper ramps 618*a*, 618*b* of the body 610. In other words, at the contracted height, the difference in angle x between the different ramps causes a gap 702 between the ramps, with a first end gap 702*a* formed closer to the first end of the second endplate 630 and a second end gap 702*b* formed closer to the second end of the second endplate 630. The degree of the gap 702 will determine what lordosis the device will tip into upon expansion. For example, if the degree of the gap 702 is 4 degrees (e.g., x=4), the second endplate 630 will tip into 4 degrees of lordosis. As the same mechanism is provided for the first endplate 620, the first endplate 620 will also tip into 4 degrees of lordosis, thereby providing an overall lordosis of 8 degrees once both endplates 620, 630 have been tipped. In some embodiments, the endplates 620, 630 themselves can have built-in lordosis. For example, if the built in lordosis of both endplates 620, 630 was 7 degrees inclusive, then the overall lordosis following expansion wherein x=4 is 15 degrees of lordosis. While the present embodiment shows an angle x difference of 4 degrees, the angle can be less or more, thereby resulting in less or more lordosis.

Figure 71A:
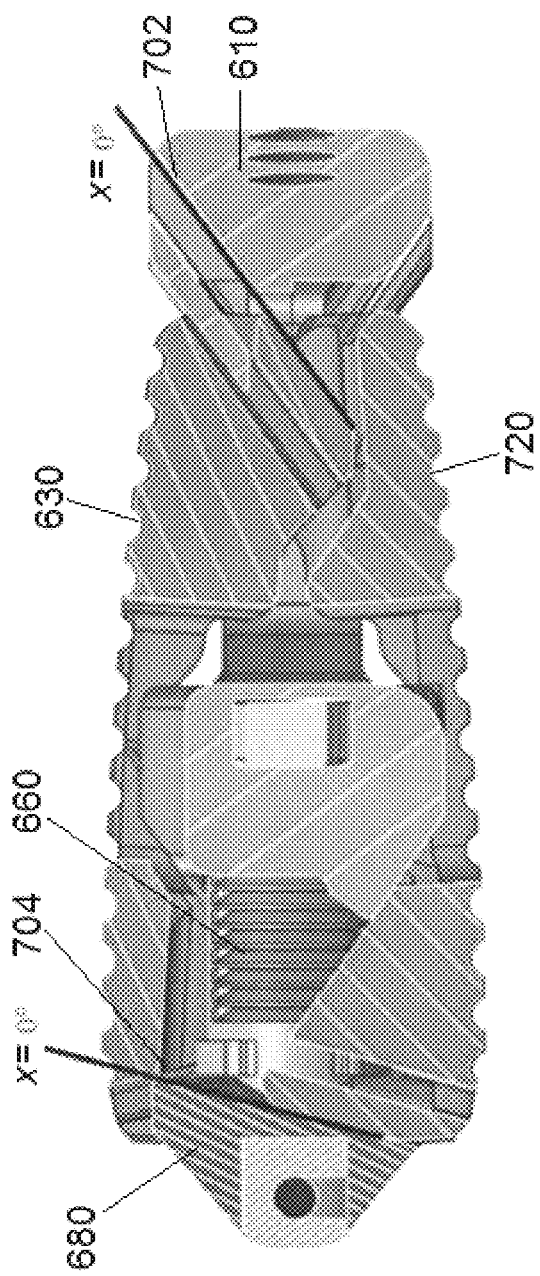

FIGS. 71A-71C are different views of the expandable fusion device of FIG. 68 in a tipped state without full expansion in accordance with some embodiments. To tip the expandable fusion device 600 into lordosis, the nose 680 is initially ratcheted or pulled back towards the body 610, thereby causing the gaps x to close and the corresponding ramps to mate. The amount of lordosis will be pre-determined based on the initial ramp gap x. In the present embodiment, the expandable fusion device 600 has been tipped into a lordotic angle of 4 degrees for the second endplate 630 and 4 degrees for the first endplate 620, thereby resulting in a total of 8 degrees of lordosis (as shown in FIG. 71B). One skilled in the art can appreciate that the total degree of lordosis can be less than or greater than 8 degrees, and that 8 degrees in just a representative example.

Figure 72A:
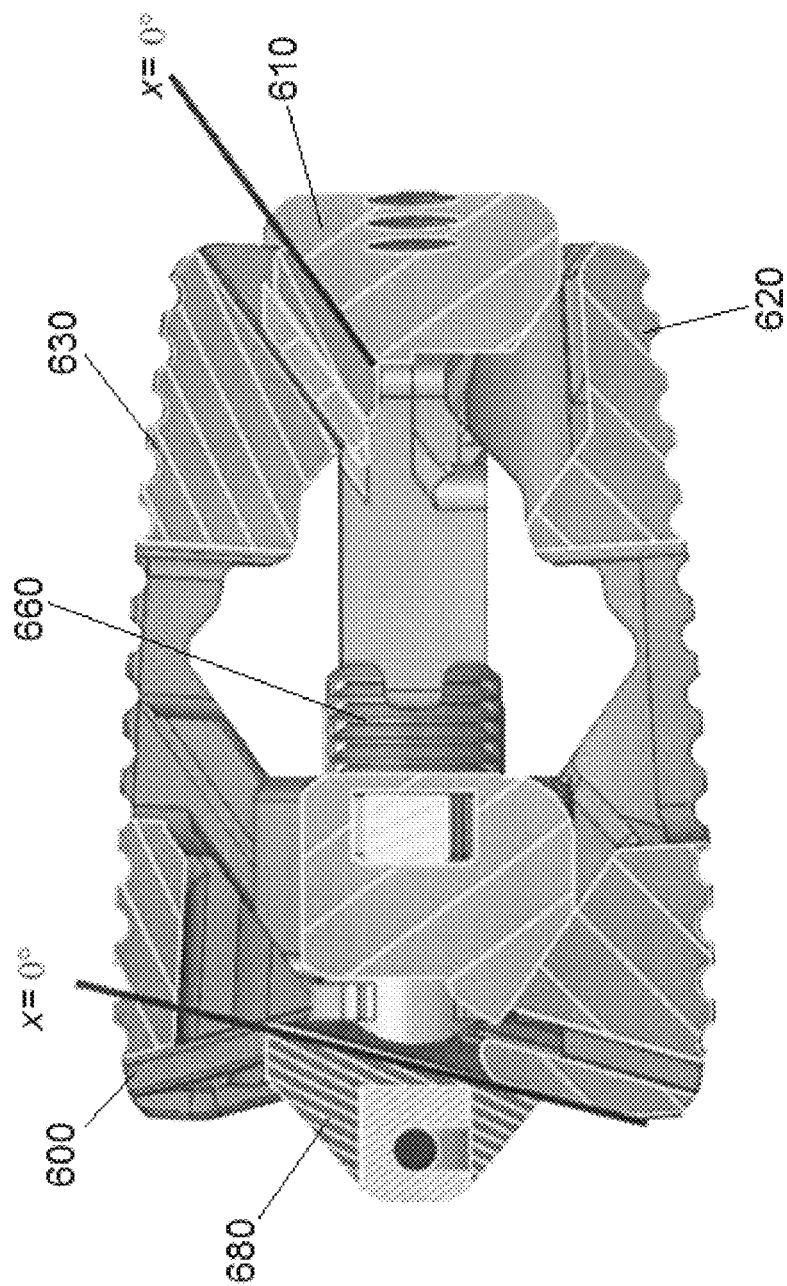
FIGS. 72A-72C are different views of the expandable fusion device of FIG. 68 in a fully expanded state in accordance with some embodiments.
Figure 72C:
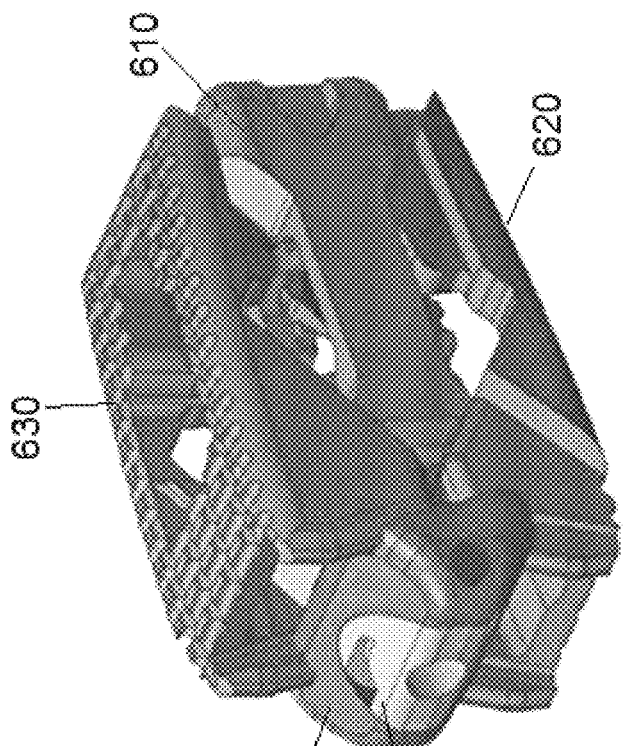
Figure 72B:
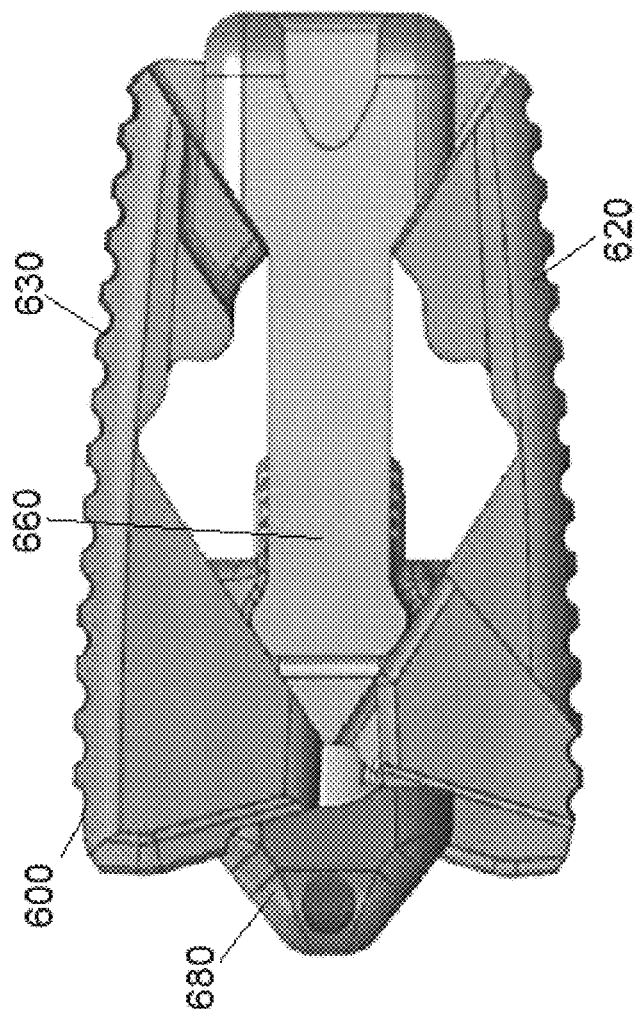

FIGS. 72A-72C are different views of the expandable fusion device of FIG. 68 in a fully expanded state in accordance with some embodiments. As the nose 680 is pulled back further the corresponding ramps of the device 600 are fully mated, the implant then begins to expand in overall height in a parallel fashion. In other words, the anterior and posterior aspects of the device 600 expand at the same rate. As this happens, the device maintains the same lordosis allowing the lordotic angle to be seen throughout the expansion range. For example, the degree of lordosis of the device 600 in the fully expanded state (as shown in FIG. 72B) is the same as the degree of lordosis of the device 600 after the endplates have been tipped (as shown in FIG. 71B). However, due to further parallel expansion, the height of the device 600 in the fully expanded state (as shown in FIG. 72B) is greater than the height of the device 600 after the endplates have been tipped (as shown in FIG. 71B).

The expandable fusion device 600 can advantageously be expanded via a ratcheting mechanism. More details regarding the ratcheting mechanism—in particular, the stem 660 and the collar 670—will be provided with respect to FIGS. 73-76.

Figure 73:
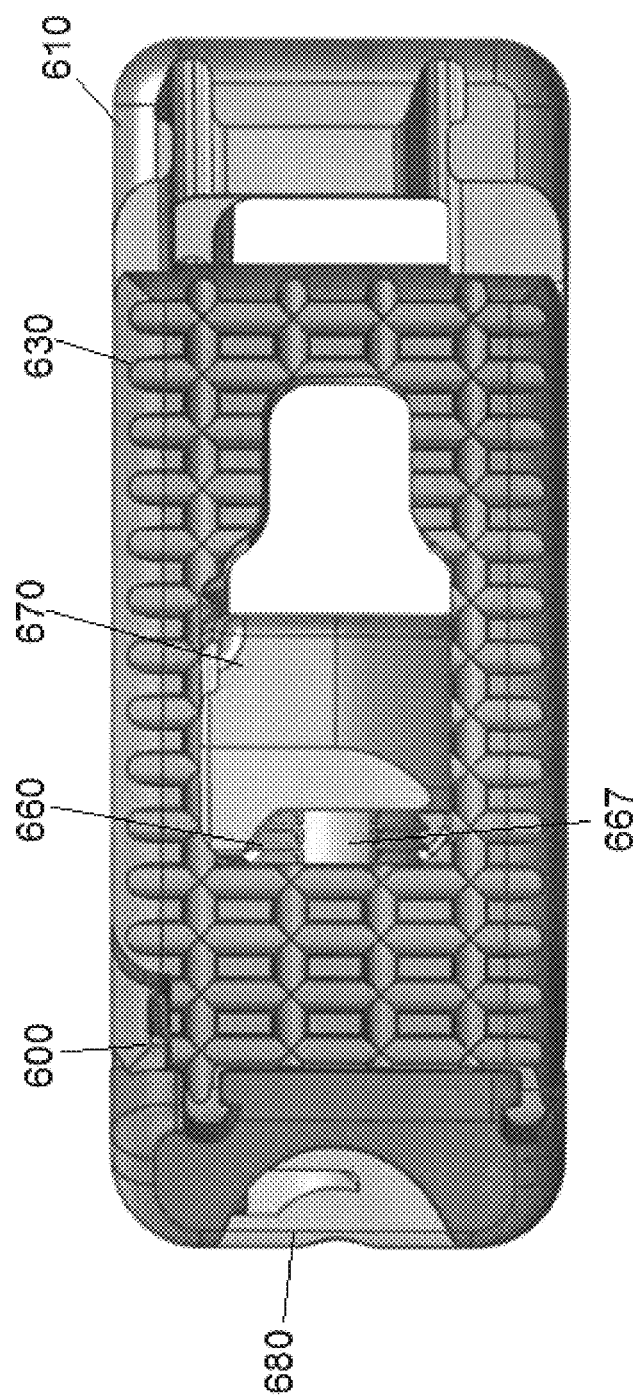
FIG. 73 is an upper view of the expandable fusion device of FIG. 68 in accordance with some embodiments.

FIG. 73 is an upper view of the expandable fusion device of FIG. 68 in accordance with some embodiments. From this view, one can see how collar 670 is housed in the body 610, and how the stem 660 is received in the collar 670. The stem 660 is further received in the nose 680, such that as the stem is pulled back, the nose 680 can also be pulled back thereby causing ratcheted expansion of the device 600.

Figure 74:
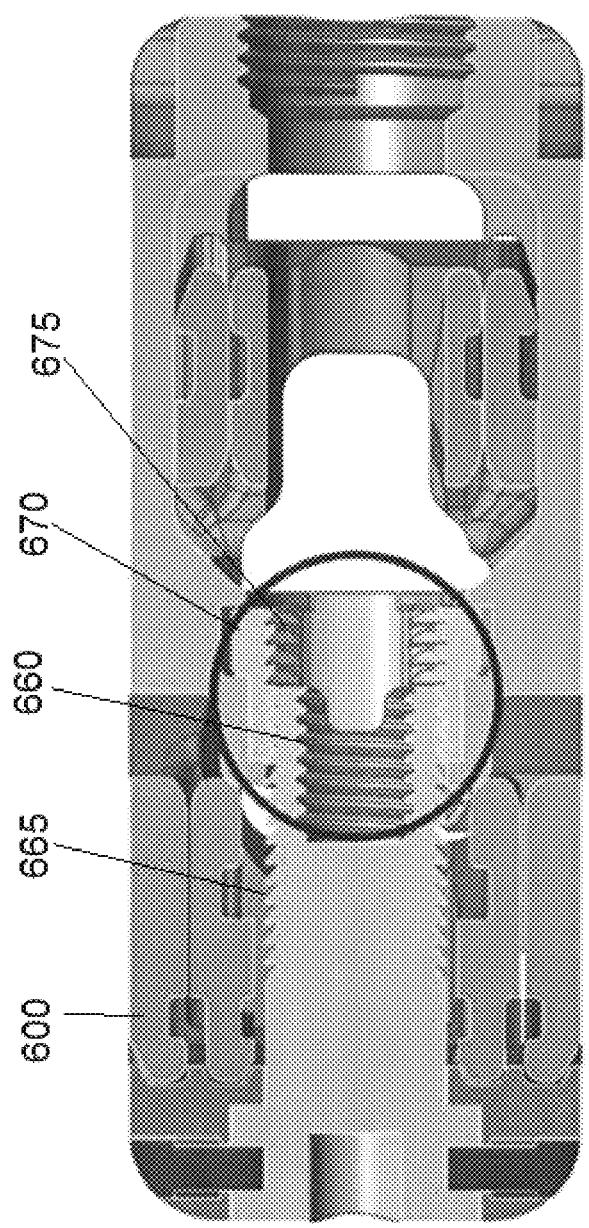
FIG. 74 is an upper cross-sectional view of the expandable fusion device of FIG. 68 in accordance with some embodiments.

FIG. 74 is an upper cross-sectional view of the expandable fusion device of FIG. 68 in accordance with some embodiments. In this view, one can see how the stem 660 having ratchet teeth 665 is engaged with the collar 670 to create an expandable ratcheting mechanism. In some embodiments, the stem 660 comprises the "male" ratcheting feature, while the collar 670 comprises the "female" ratcheting feature.

Figure 75:
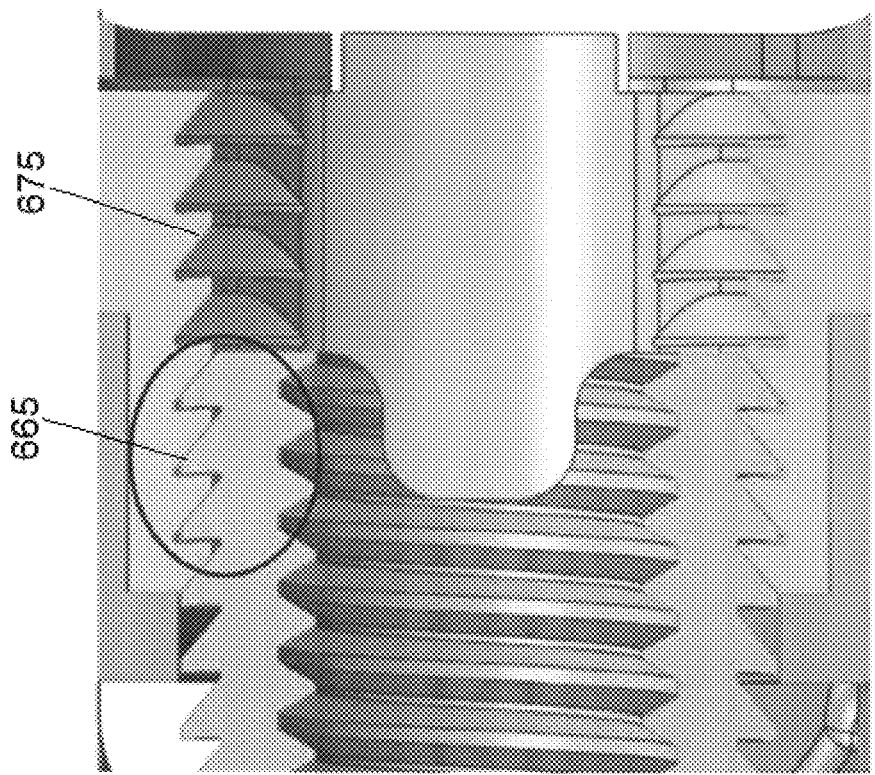
FIG. 75 is a close up view of the ratcheting mechanism of the expandable fusion device of FIG. 68 in accordance with some embodiments.

FIG. 75 is a close up view of the ratcheting mechanism of the expandable fusion device of FIG. 68 in accordance with some embodiments. This view shows the male ratchet of the stem 660 and the female ratchet of the collar 670 in more detail. As the stem 660 is pulled back, the collar 670 springs open like a C-ring and allows the ratchet teeth 665 of the stem 660 to advance to the next slot or recess 675 formed in the collar 670. The stem 660 advantageously moves in increments through the collar 670. These non-continuous increments drive height increases. In some embodiments, the height increases can increase in increments greater than 0.2 mm and 0.8 mm. In some embodiments, the height increases are in increments of approximately 0.5 mm.

Figure 76:
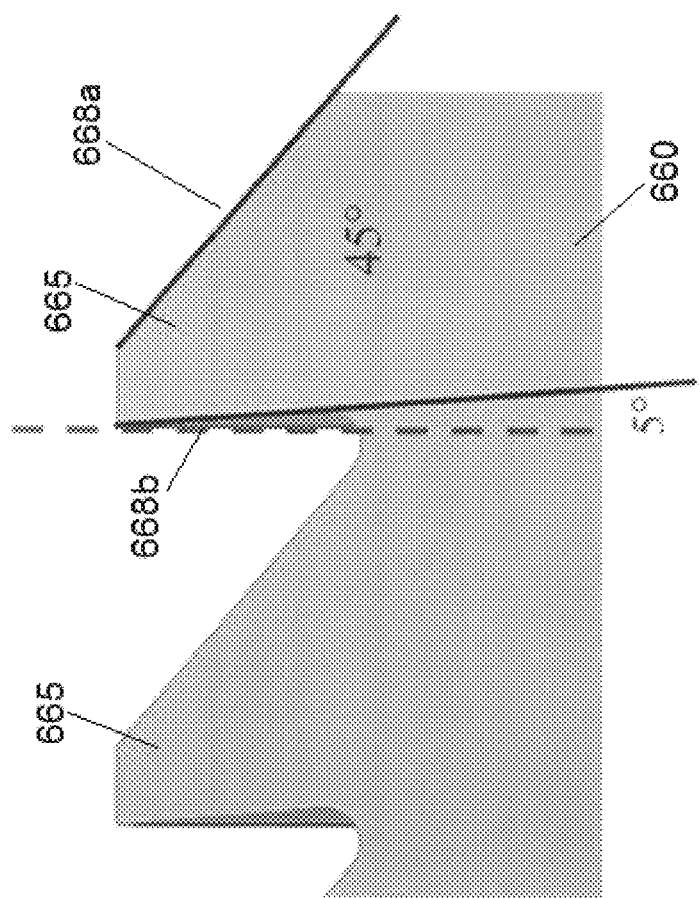
FIG. 76 is a close up view of the ratchet teeth of the expandable fusion device of FIG. 68 in accordance with some embodiments.

FIG. 76 is a close up view of the ratchet teeth of the expandable fusion device of FIG. 68 in accordance with some embodiments. Each of the ratchet teeth 665 comprises an inclusive angle 668a and a back angle 668b. In some embodiments, the ratchet teeth 665 comprise an inclusive angle 668a of between 30 and 60 degrees, and in particular about 45 degrees. In some embodiments, the back angle 668b comprises between 2 and 8 degrees, and in particular about 5 degrees. Under load, the ratchet connection is pulled in the direction of disengagement. Advantageously, the purpose of the back angle 668b is to keep the stem 660 more engaged, especially in the back area when the device 600 is under load by pulling the collar 670 closer to the ratchet teeth 665 when pulled in the direction of disengagement.

Figure 77:
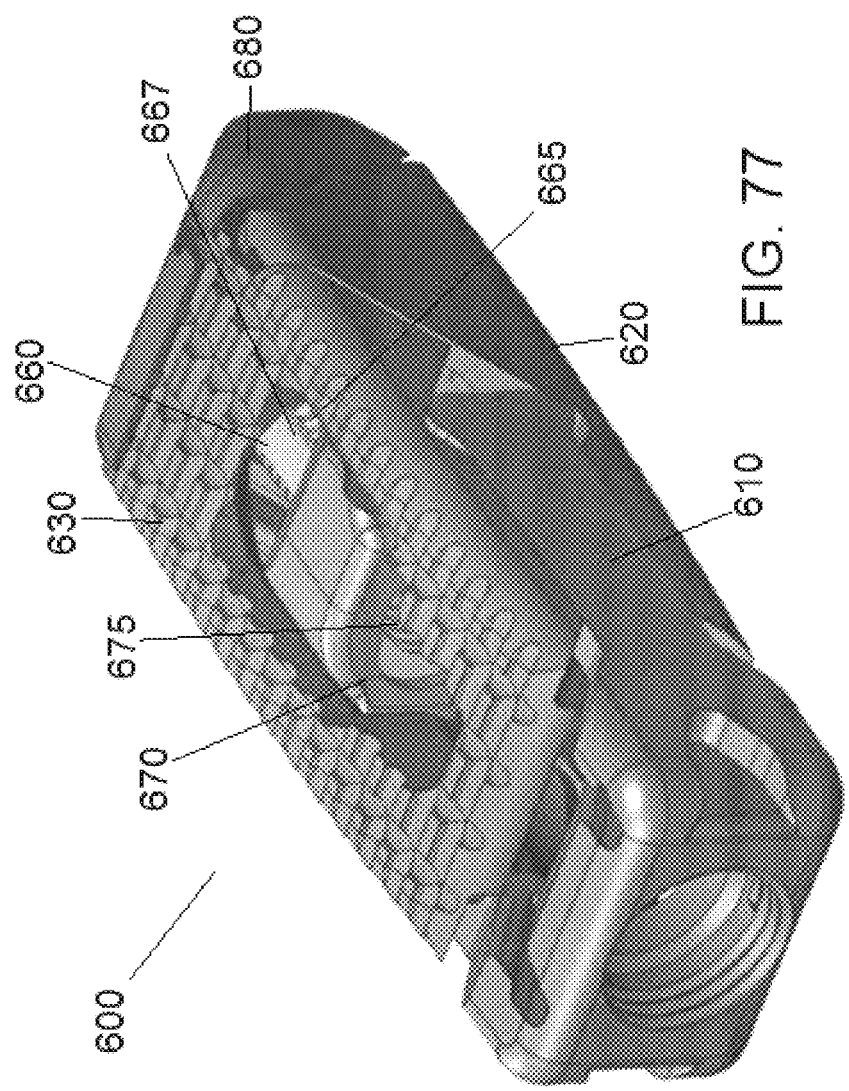
FIG. 77 is a top perspective view of the expandable fusion device of FIG. 68 in accordance with some embodiments.

FIG. 77 is a top perspective view of the expandable fusion device of FIG. 68 in accordance with some embodiments. In this configuration, the fusion device 600 is capable of ratcheted expansion. In addition to providing ratcheted expansion, the device is also capable of collapse and contraction. To accommodate contraction, the device 600 advantageously provides ratchet teeth 665 on only a portion of the stem 660, whereby the ratchet teeth 665 are separated by one or more flat areas 667. In the particular embodiment, the device 600 includes two sets of ratchet teeth 665 each of which is adjacent two sets of flat areas 667. These features allow a device to be converted between a "locked" configuration whereby ratcheting is enabled and a "disengaged" configuration whereby ratcheting is disabled. These features are discussed below with respect to FIGS. 78A-78G.

Figure 78C:
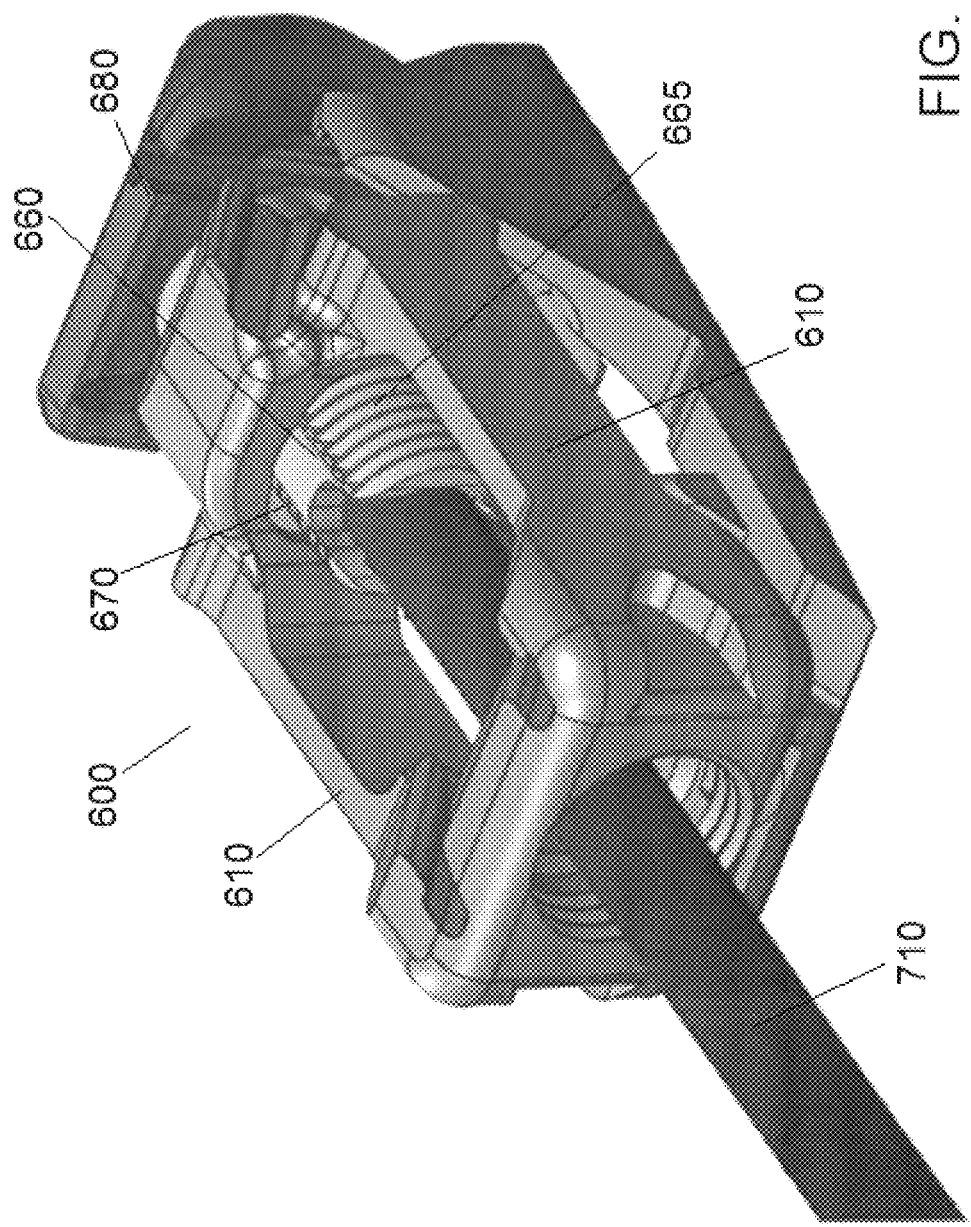
Figure 78D:
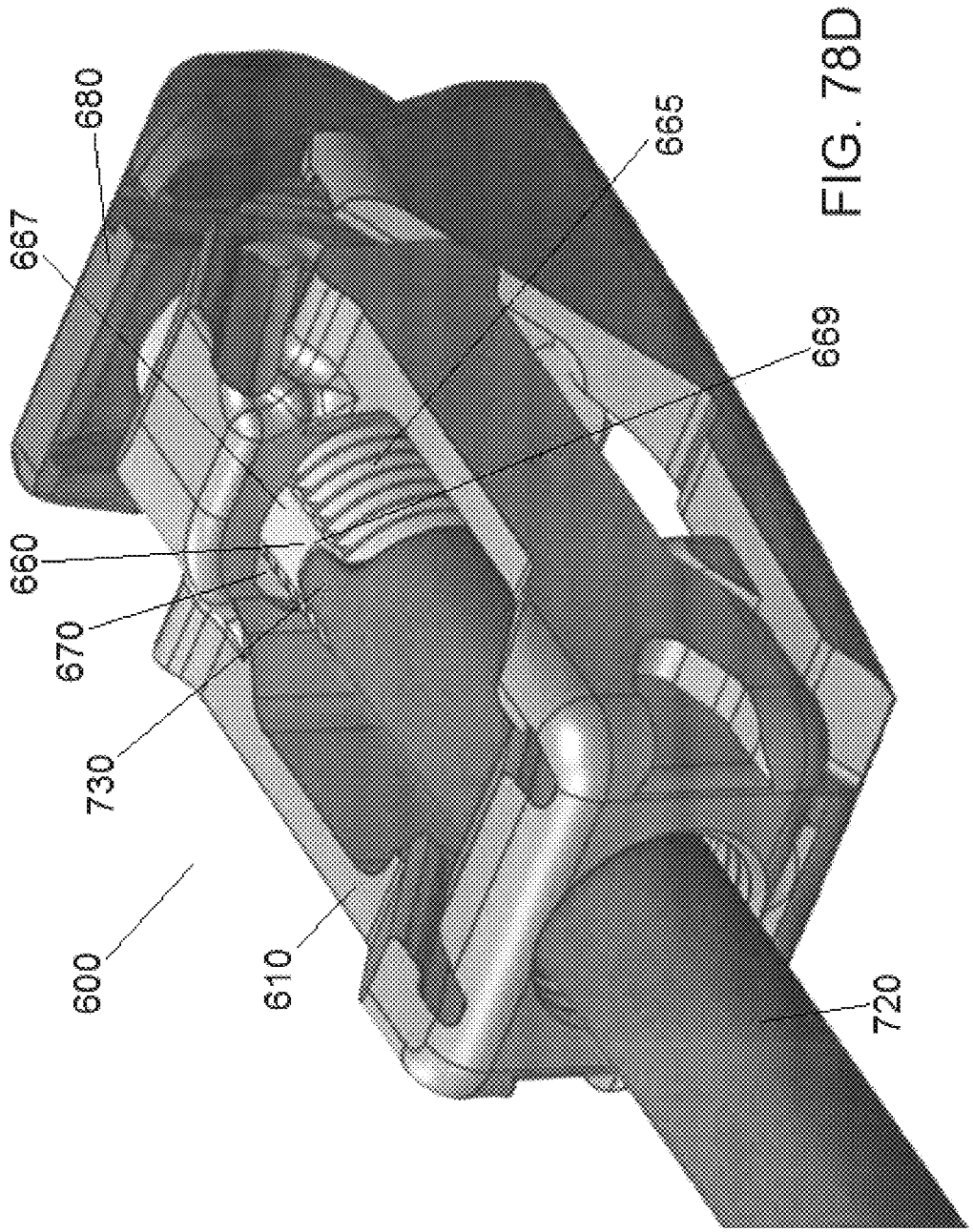

FIGS. 78A-78G are top perspective views of the expandable fusion device of FIG. 68 transitioning from a locked configuration to a disengaged configuration in accordance with some embodiments. FIG. 78A shows an expandable fusion device in a "locked" configuration whereby the device is capable of ratcheted expansion. As shown in FIG. 78A, the ratchet teeth 665 of the stem 660 are aligned and engaged with the ratchet recesses 675 of the collar 670, thereby enabling ratcheted expansion.

FIG. 78B shows the expandable fusion device with an expansion tool inserted therein. The expansion tool 710 is capable of engaging the stem 660 in the "locked" configuration, whereby the stem 660 (and hence the nose 680) is capable of being pulled back. As the stem 660 and nose 680 are drawn back, this causes incremental ratcheting expansion of the device 600 based on the design of the ratchet teeth.

FIG. 78C shows the expandable fusion device when fully expanded. As shown in the figure, the stem 660 has been pulled further into the body 610, thereby causing greater height expansion of the device. The fusion device 600 has a relatively higher height in FIG. 78C than in FIG. 78B. Advantageously, the fusion device 600 can also be contracted by a surgeon if desired.

FIG. 78D shows the expandable fusion device prior to contraction with the device still in a "locked" ratcheting configuration. To contract the device 600, a disengagement tool 720 (separate from the expansion tool 710) is provided. The disengagement tool 720 comprises a shaft having a distal nub 730. The disengagement tool 720 is advantageously designed to rotate the stem 660, such that the device is changed from a "locked" ratchetable configuration to a "disengaged" unratchetable configuration, as discussed above. To rotate the stem 660, the distal nub 730 of the disengagement tool 720 mates with a correspondingly shaped recess 669 in the stem 660. With the disengagement tool 720 engaged with the stem 660, the stem 660 can be rotated (e.g., 90 degrees), thereby converting the device into a disengaged configuration, as shown in FIG. 78E.

Figure 78E:
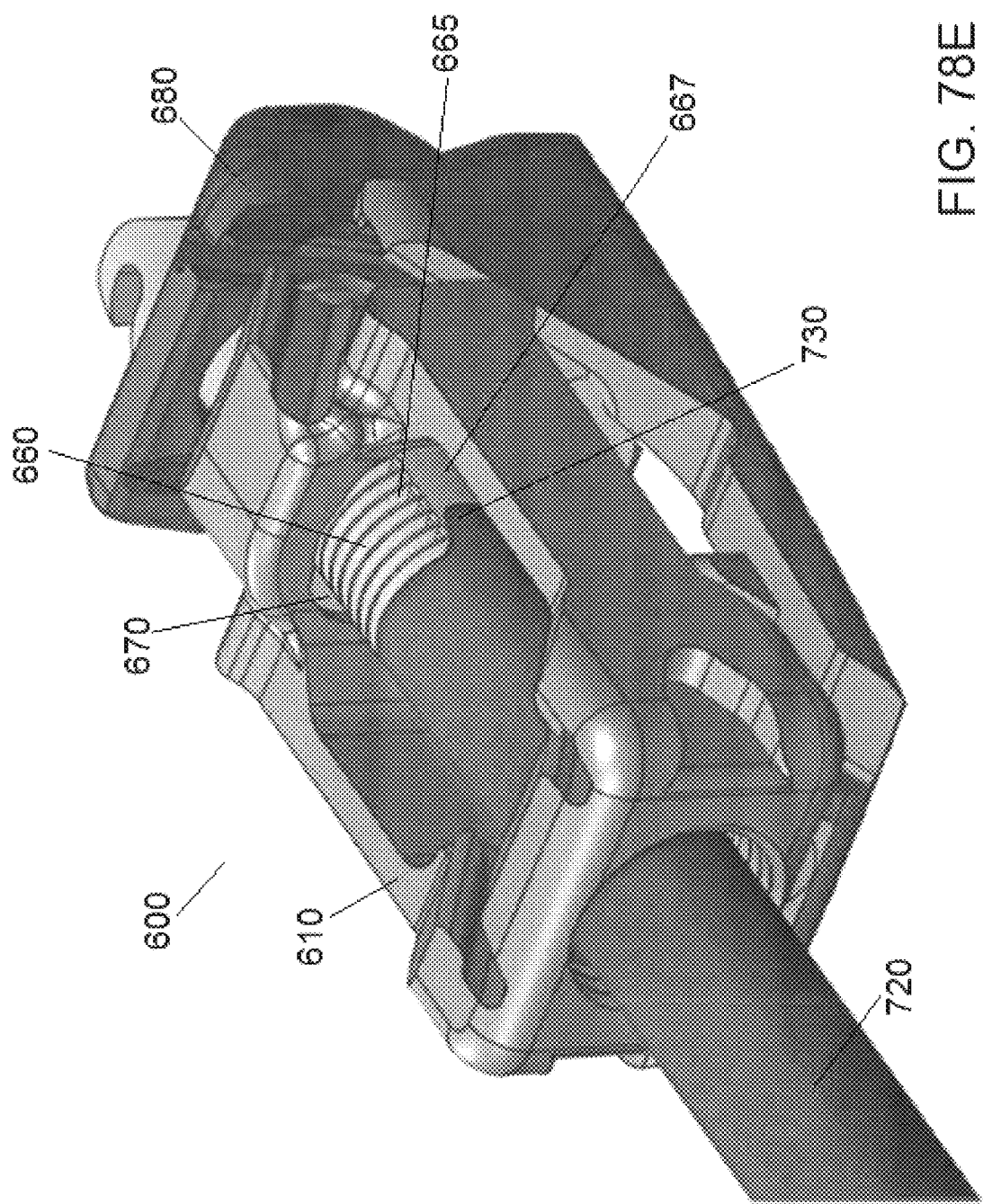

FIG. 78E shows the expandable fusion device in a "disengaged" non-ratchetable configuration. The stem 660 has been rotated such that its pair of flat areas 667 align and face the collar 670. As such, the ratchet teeth 665 of the stem are no longer engaged with ratchet slots of the collar 670, thereby allowing the stem 660 to be pushed forward to contract the device.

FIG. 78F shows the expandable fusion device in a "disengaged" configuration whereby the device has been fully contracted. At this stage, the device 600 is the same height as it was prior to expansion. The device 600 is fully capable of expansion again. A surgeon simply needs to rotate the stem 660 in an opposite direction 90 degrees, such that the device is brought back into a "locked" ratcheting configuration.

FIG. 78G shows the expandable fusion device whereby the device is brought back to a "locked" ratcheting configuration. By rotating the disengagement tool 720 in a reverse direction 90 degrees, this rotates the stem 660 whereby the ratchet teeth 665 are once again engaged with ratchet slots of the collar 670. The fusion device 600 can once again be expanded via a ratcheting mechanism if desired. Advantageously, the expandable fusion devices described above are each capable of being inserted through a minimal incision, as the devices can maintain a minimal profile prior to expansion.

In posterior interbody fusion procedures, surgeons are required to consider a number of anatomical aspects when implanting a device. For example, surgeons must often consider the surrounding nerve roots and avoid disrupting them, or they may need to consider the size of the intervertebral disc being replaced. In many cases, a collapsed disc space is involved that requires surgical intervention to restore height. When the posterior margin of any disc is smaller than the anterior margin and when the disc is collapsed, the posterior margin is even smaller, making it very difficult to insert a device. The reduced posterior margin restricts the surgeon because they need the device to be small enough to be able to be fully implanted while at the same time being large enough to fill the anterior space and restore disc height. The expandable fusion device described in more detail below with respect to FIGS. 79-89 provides the advantage of allowing the surgeon the insert the device at a collapsed height past the posterior margin while not disrupting the surrounding nerve roots. The device can subsequently be expanded in the anterior space to restore the disc height and provide an endplate to endplate fit.

Figure 79:
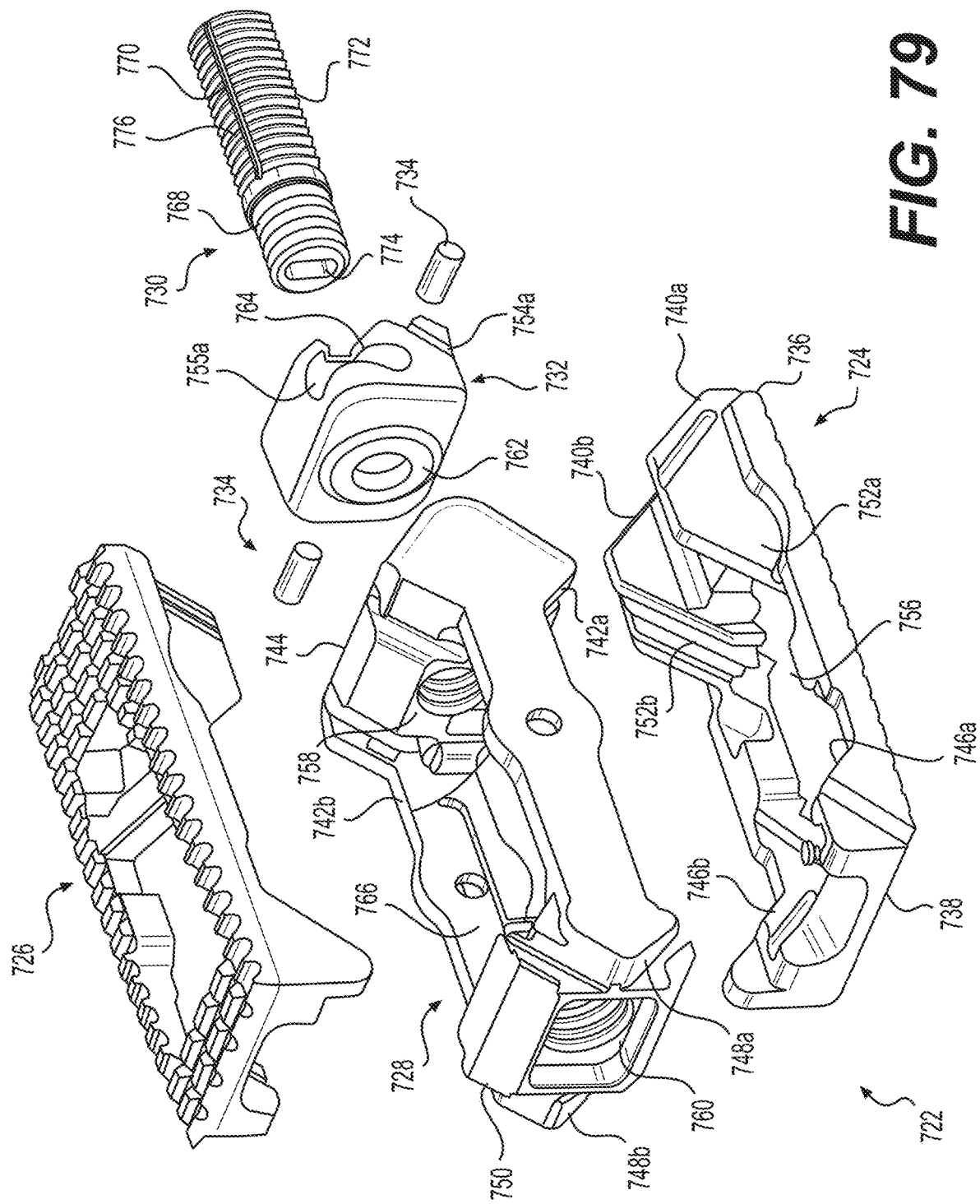
FIG. 79 is an exploded view of an expandable fusion device having an expandable spacing mechanism in accordance with some embodiments.
Figure 80:
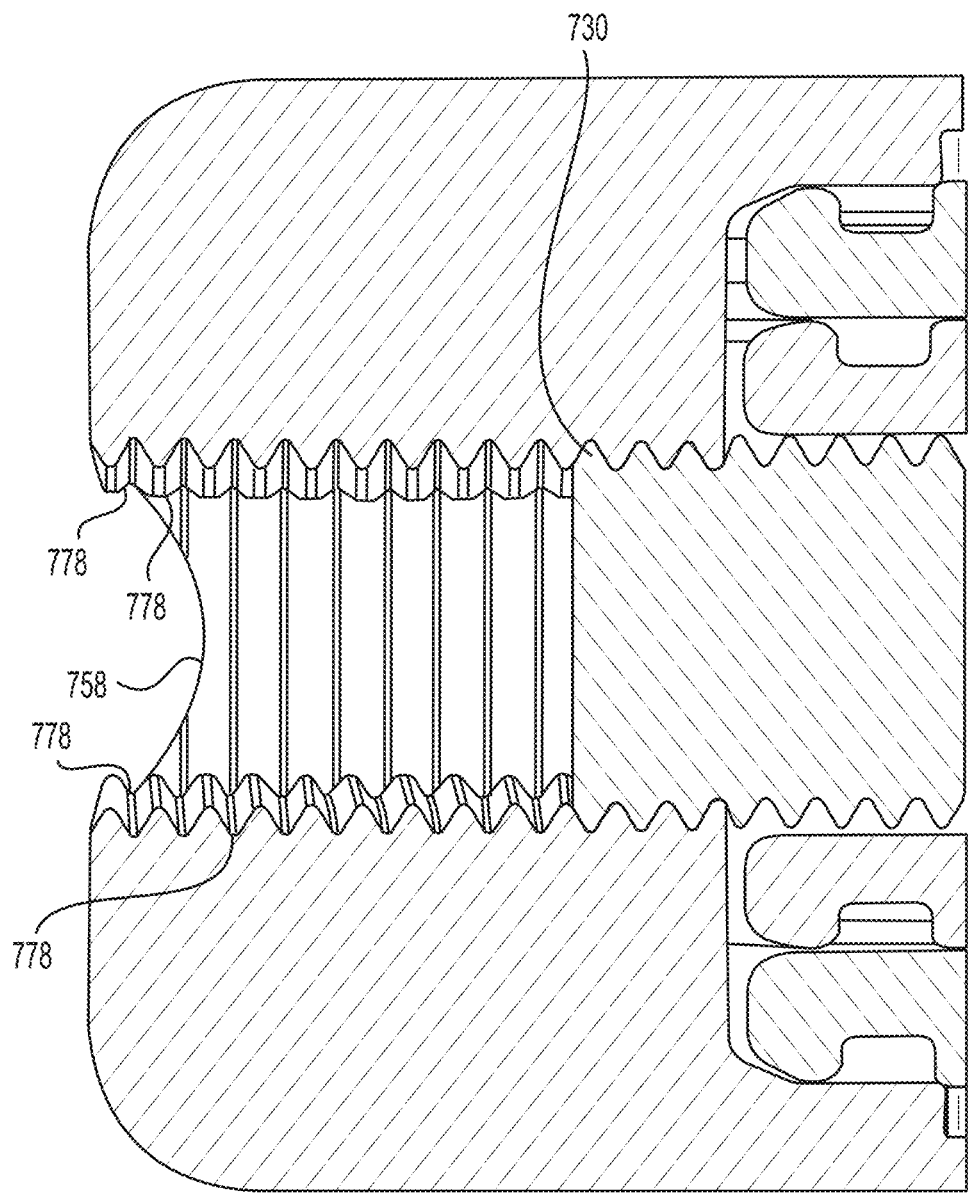
FIG. 80 is a diagram showing a view of an exemplary "locked" configuration of the fusion device of FIG. 79.

FIG. 79 is an exploded view of an expandable fusion device having an expandable spacing mechanism in accordance with some embodiments. The expandable fusion device 722 comprises a first endplate 724, a second endplate 726, a body 728 positioned between the first endplate 724 and the second endplate 726, a stem 730, a middle (mid) ramp piece 732, and two ramp pins 734. The stem 730 and associated mid ramp piece 732 advantageously provide an expandable spacing mechanism to the expandable fusion device. The expandable fusion device can be expanded or contracted to achieve a desired expansion.

Although the following discussion relates to the first endplate 724, it should be understood that it also equally applies to the second endplate 726, as the second endplate 726 is substantially identical to the first endplate 724 in various embodiments of the present invention. It should be understood that, in one embodiment, the first endplate 724 is configured and dimensioned to interlock with the second endplate 726. The first endplate 724 comprises a lower endplate having a first end 736 and a second end 738. The first end 736 comprises a pair of first end ramped portions 740a, 740b. Each of these ramped portions 740a, 740b is configured and dimensioned to engage corresponding lower ramps 742a, 742b of the front end 744 of the body 728 to aid with expansion of the expandable fusion device.

The second end 738 of the first endplate 724 comprises a pair of second end ramped portions 746a, 746b. Each of these ramped portions 746a, 746b is configured and dimensioned to engage corresponding lower ramps 748a, 748b on the back end 750 of body 728 to aid with expansion of the expandable fusion device. The first endplate 724 also includes a third pair of mid ramps 752a, 752b that are positioned between the first end ramped portions 740a, 740b and second end ramped portions 746a, 746b. It may be desirable for the mid ramps 752a, 752b to be configured and dimensioned to be positioned near the first end ramped portions 746a, 746b, as shown in FIG. 79. Each of the mid ramps 752a, 752b is configured and dimensioned to engage corresponding lower ramps 754a, 754b (754b not visible) of the mid ramp piece 732 to aid with expansion of the expandable fusion device 722. The mid ramp piece 732 may also include upper ramps 755a, 755b (755b not visible) that are configured and dimensioned to engage with corresponding mid ramps of the second endplate 726. The ramps of the first endplate 724 are formed along a perimeter that surrounds a central opening 756.

In one embodiment, the body 728 comprises a front throughbore 758 and rear throughbore 760. The front throughbore 758 comprises an opening for receiving the stem 730 therethrough. The front throughbore 758 may include recesses, as described in more detail below. The rear throughbore 760 comprises an opening through which one or more tools (e.g., an expansion tool and a disengagement tool) can pass through, as discussed with respect to FIGS. 78B and 78D above. In some embodiments, the rear throughbore 760 is threaded to allow engagement by an insertion tool. As shown in FIG. 79 and discussed above, the body 728 comprises at least one angled surface or ramps that are configured and dimensioned to engage corresponding ramps on the first endplate 724, second endplate 726, or mid ramp piece 732. Sliding the ramps against one another causes the expansion of the expandable fusion device.

The mid ramp piece 732 may include at least one angled surface or ramp that is configured and dimensioned to engage corresponding ramps on the first endplate 724, second endplate 726, and/or the body 728, as discussed above. The mid ramp piece 732 also includes a throughbore 762 that comprises an opening for receiving the stem 730 therethrough. In some embodiments the throughbore 762 may be threaded to allow it to be fixed to the mid ramp piece 732. It is desirable for the stem 730 to be operable to rotate within the throughbore 762. The mid ramp piece 732 may also include at least two openings 732 (one not visible) that are configured and dimensioned to receive a portion of each of the two ramp pins 734. When the ramp pins 734 are inserted into the openings 732, a portion of them extends outside the openings 764 of the mid ramp piece 732. When the mid ramp piece 732 is inserted into the body 728, the portion of the ramp pins 734 that extends outside of the openings 764 engages with slots 766 in the body 728. The slots 766 may be configured and dimensioned on one or more interior surfaces of the body 728. When engaged, the ramp pins 734 and slots 766 allow the mid ramp piece 732 to slide horizontally, or translate, within the body 728. In one embodiment, the slots 766 may be configured and dimensioned in the body 728 so that they keep the mid ramp piece 732 on a centerline of the interior of the body 728, as shown in FIG. 79. In an alternate embodiment, the ramp pins 734 may comprise protrusions that are configured and dimensioned as part of the mid ramp piece 732 to engage with the slots 766.

According to one embodiment, the stem 730 and the mid ramp piece 732 form a mechanism for causing expansion of the expandable fusion device. The stem 730 comprises an elongate shaft that may include two portions. In one embodiment, the two portions of the shaft may have different diameters, although in other embodiments the shaft may have the same diameter throughout. In one embodiment, the first portion 768 of the shaft may be configured and dimensioned to be received in the throughbore 762 of the mid ramp piece 732. In embodiments where the throughbore 762 is threaded, the first portion 768 has corresponding threads that allow it to matingly engage with the mid ramp piece 732. As discussed above, it may be desirable for the first portion 768 to be operable to rotate a predetermined amount within the throughbore 762.

A second portion 770 of the stem 730 includes grooves, e.g., teeth 772 configured and dimensioned along a portion of the length of the shaft, as shown in FIG. 79. One advantage of including grooves 772 is that, in some embodiments, rotation of the stem 730 causes the expandable fusion device to be changed from a "locked" configuration into a "disengaged" configuration, as will be discussed further below. At least part of the stem 730 comprises an elongate body that includes an opening 774 for receiving a tool, such as an expansion tool or the like, therethrough. In addition, the second portion 770 of the stem 730 comprises one or more flat areas 776 that are positioned adjacent to the teeth 772. In some embodiments, the second portion 770 comprises a pair of flat areas 776 that are positioned about 180 degrees apart from one another.

According to one embodiment, the stem 730 is capable of two configurations. In a first "locked" configuration shown in FIG. 80, the teeth 772 of the stem 730 are engaged with corresponding recesses 778 of the front throughbore 758 of the body 728, as circled in FIG. 80. In a second "disengaged" configuration, shown in FIG. 81, the stem 730 is rotated such that the one or more flat areas 776 are positioned adjacent the recesses 778 of the front throughbore 758, such that movement of the stem 730 within the throughbore 758 is possible. In this second disengaged configuration, the stem 730 may move back and forth within the throughbore 758, causing expansion or contraction of the expandable fusion device, as described in more detail below.

FIGS. 82A-82C are side views of the expandable fusion device 722 of FIG. 79 in the process of expansion in accordance with some embodiments. In one embodiment, the expandable fusion device 722 is advantageously operable to expand and, in particular, lordotically expand. According to one embodiment, the device 722 may begin in a contracted state, as shown in FIG. 82A. When the stem 730 is rotated to the released position, the mid ramp piece 732 may be pushed towards the front end of the first endplate 724 and second endplate 726, as shown in FIG. 82B. When the expandable fusion device 722 expands, the endplates 724, 726 first tip into lordosis, as shown in FIG. 82B. Once the fusion device 722 has achieved maximum lordosis, the device 722 can continue to expand in height in a parallel fashion, whereby both the anterior and posterior aspects expand at the same rate until the fusion device 722 reaches a maximum expansion, as shown in FIG. 82C. In other words, once the device 722 reaches a particular lordotic angle (as shown in FIG. 82B), the device 722 will maintain the lordotic angle throughout the expansion range until maximum expansion has been achieved, as shown in FIG. 82C. More details on the expansion of the device 722 are provided below.

Figure 83A:
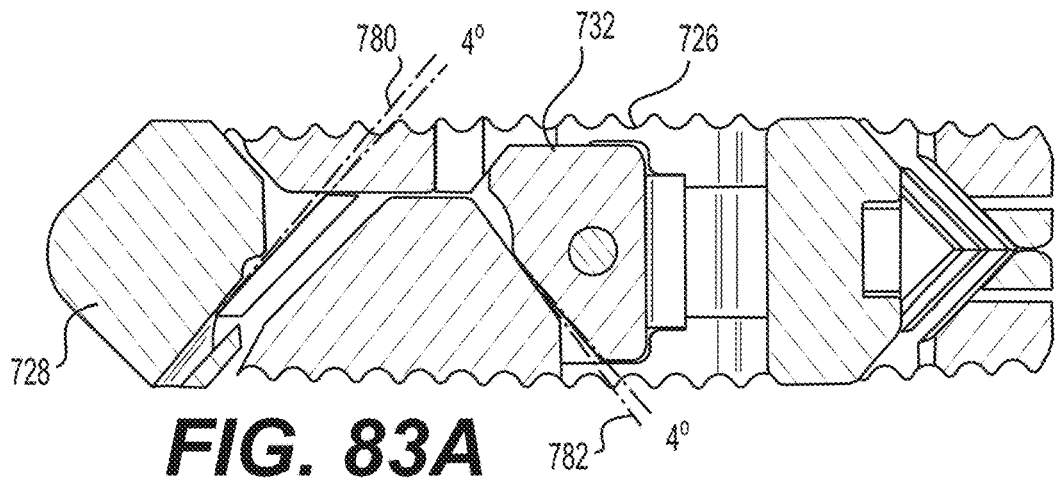
FIGS. 83A-83C are different views of the expandable fusion device of FIG. 79 in a contracted state in accordance with one embodiment of the present invention.
Figure 83B:
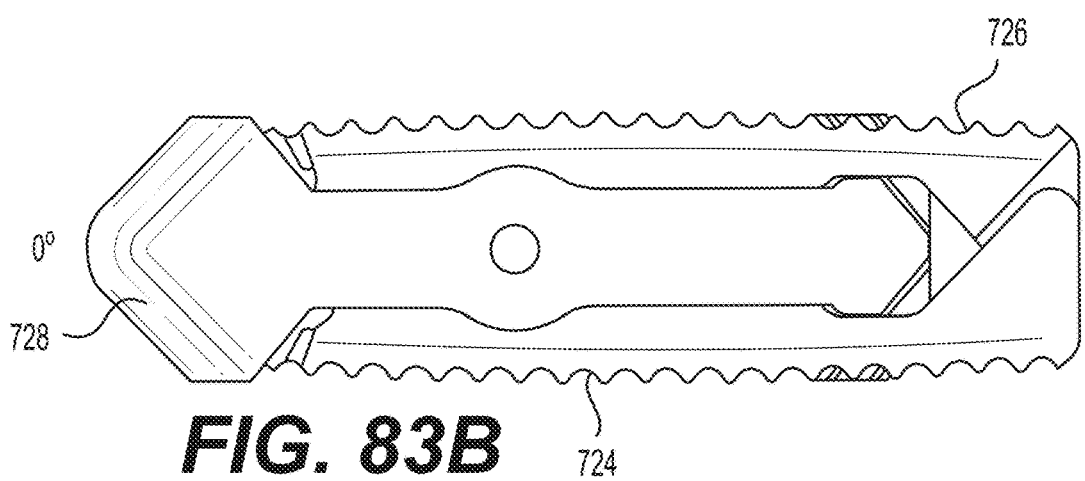
Figure 83C:
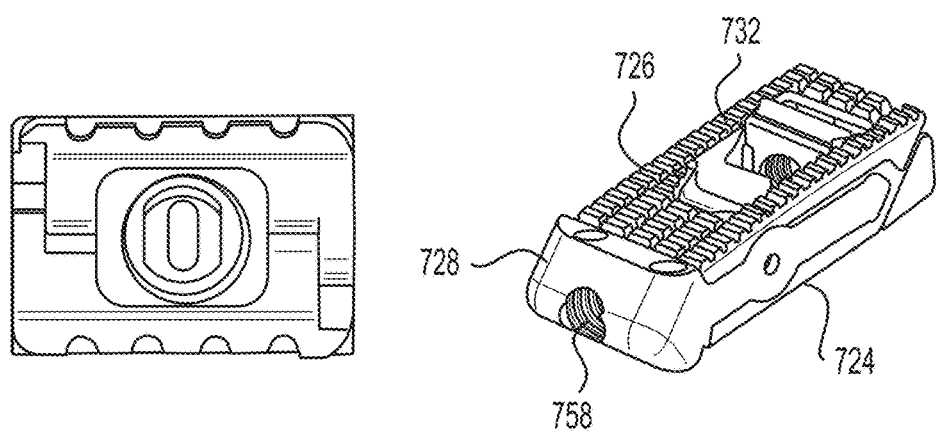

FIGS. 83A-83C are different views of the expandable fusion device of FIG. 79 in a contracted state in accordance with one embodiment of the present invention. From the contracted state, the device 722 is operable to first expand and tip into lordosis, and then expand in a parallel fashion. In one embodiment, the angle tipping is generated by a difference in ramp angle x that is seen between the first end ramps 740a, 740b and the lower ramps 742a, 742b as well as between the mid ramps 752a, 752b and the lower ramps 754a, 754b of the mid ramp piece 732. Similarly, the same difference in ramp angle x is seen between the corresponding ramped portions of the second endplate 726 and the body 728 and the mid ramp of the second endplate 726 and the mid ramp piece 732. In other words, at the contracted height, the difference in angle x between the different ramps causes a first gap 780 between the body 728 and the first and second endplates 724, 726, and a second gap 782 between the mid ramp piece 732 and the mid ramps 752a, 752b of the first and second endplates 724, 726.

The degree of the gaps 780, 782 determines what lordosis the device will tip into upon expansion. For example, if the degree of the gaps 780, 782 is 4 degrees (e.g., x=4), the first endplate 724 will tip into 4 degrees of lordosis. As the same mechanism is provided for the second endplate 726, the second endplate 726 will also tip into 4 degrees of lordosis, thereby providing an overall lordosis of 8 degrees once both endplates 724, 726 have been tipped if the endplates 724, 726 do not have any built-in lordosis, as shown in FIG. 83B. In some embodiments, the endplates 724, 726 themselves can have built-in lordosis. For example, if the built-in lordosis of both endplates 724, 726 was 7 degrees inclusive, then the overall lordosis following expansion wherein x=4 is 15 degrees of lordosis. While the present embodiment shows an angle x difference of 4 degrees, the angle can be less or more, thereby resulting in less or more lordosis.

Figure 84A:
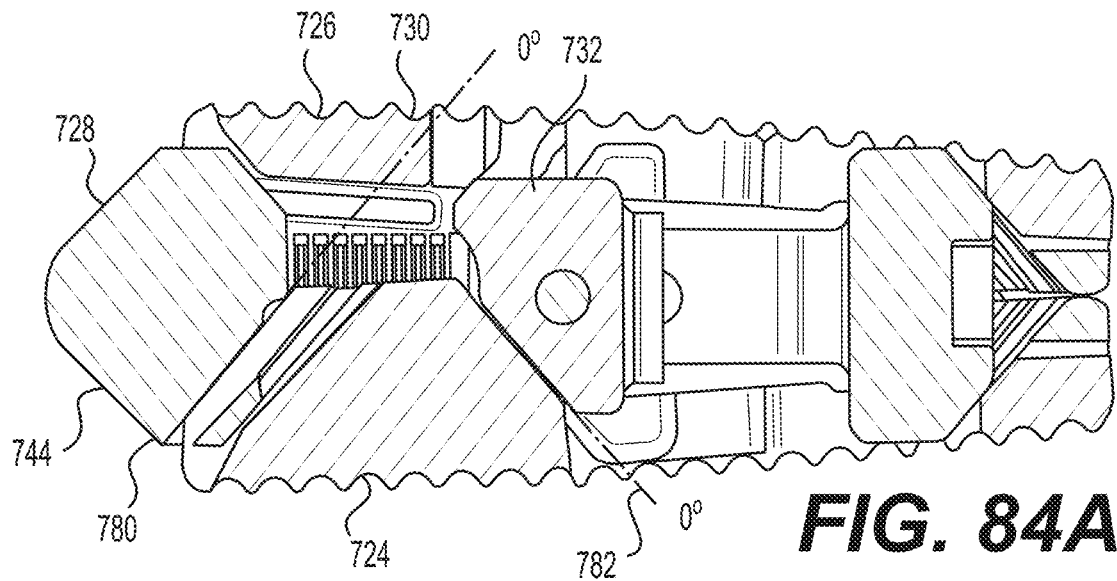
FIGS. 84A-84B are different views of the expandable fusion device of FIG. 79 in a tipped state without full expansion in accordance with one embodiment.
Figure 84B:
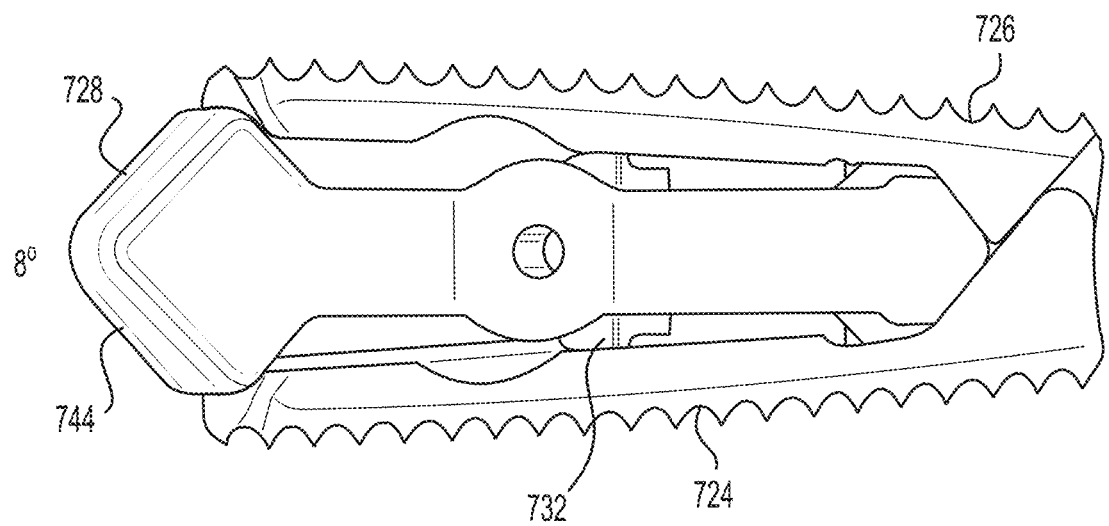

FIGS. 84A-84B are different views of the expandable fusion device of FIG. 79 in a tipped state without full expansion in accordance with one embodiment. To tip the expandable fusion device 722 into lordosis, the mid ramp piece 732 may be pushed forwards towards the front end 744 of the body 728. In this manner, the first gap 780 and second gap 782 will close, thereby causing the gaps x to close to zero degrees and the corresponding ramps to mate, as shown in FIG. 84A. The amount of lordosis will be predetermined based on the first gap 780 and the second gap 782. For example, if the ramp angle difference is 4 degrees for each endplate 724, 726 in one embodiment, the total lordosis is 8 degrees once the endplates are tipped, as shown in FIG. 84B. One skilled in the art can appreciate that the total degree of lordosis can be less than or greater than 8 degrees, and that 8 degrees in just a representative example.

Another way to describe the lordotic and parallel expansion of the expandable fusion device of FIG. 79 is with respect to the movement of the mid ramp piece 732. In other words, the mid ramp piece 732, and therefore the stem 730, may begin in a fully contracted state, with no lordosis or parallel expansion (assuming zero lordosis of the endplates 724, 726). When the mid ramp piece 732 is pushed towards the front end 744 of the body 728 by a first predetermined amount from the fully contracted state, it will engage the ramps and cause the first gap 780 and second gap 782 to close, as shown in FIG. 84A. As the mid ramp piece 732, and therefore the stem 730 continue to move towards the front end 744 of the body 728 by a second predetermined amount, each endplate 724, 726 will continue to expand away from one another in parallel, as described further with respect to FIGS. 85A-85C, until fully expanded.

In one embodiment, for instance, the first predetermined amount may be 3 mm while the second predetermined amount may be an additional 3 mm, for a total of 6 mm. In this example, the first predetermined amount may also be represented as a range between 0.5 mm and 3 mm, for instance, and the second predetermined amount may be represented as a range between 3.5 mm and 6 mm, assuming that the increments of the teeth are 0.5 mm increments, as described below. In other words, lordotic movement of each endplate 724, 726, will occur as the mid ramp piece 732, and therefore the stem 730, is moved up to 3 mm and the first gap 780 and second wpage 782 are closed. After 3 mm, the first gap 780 and second gap 782 are closed, resulting in parallel movement of each endplate 724, 726. Similarly, if the mid ramp piece 732, and therefore the stem 730 is then moved away from the front throughbore 758 near the front end 744 of the body 728, the endplates 724, 726 will move towards one another in parallel between 6 mm and 3 mm. When the mid ramp piece 732, and therefore the stem 730 is moved away from the front throughbore 758 near the front end 744 of the body 728 between 3 mm and 0 mm (the fully contracted state), the endplates 724, 726 will reduce their lordosis until there is zero lordosis, as shown in FIG. 83B.

Figure 85A:
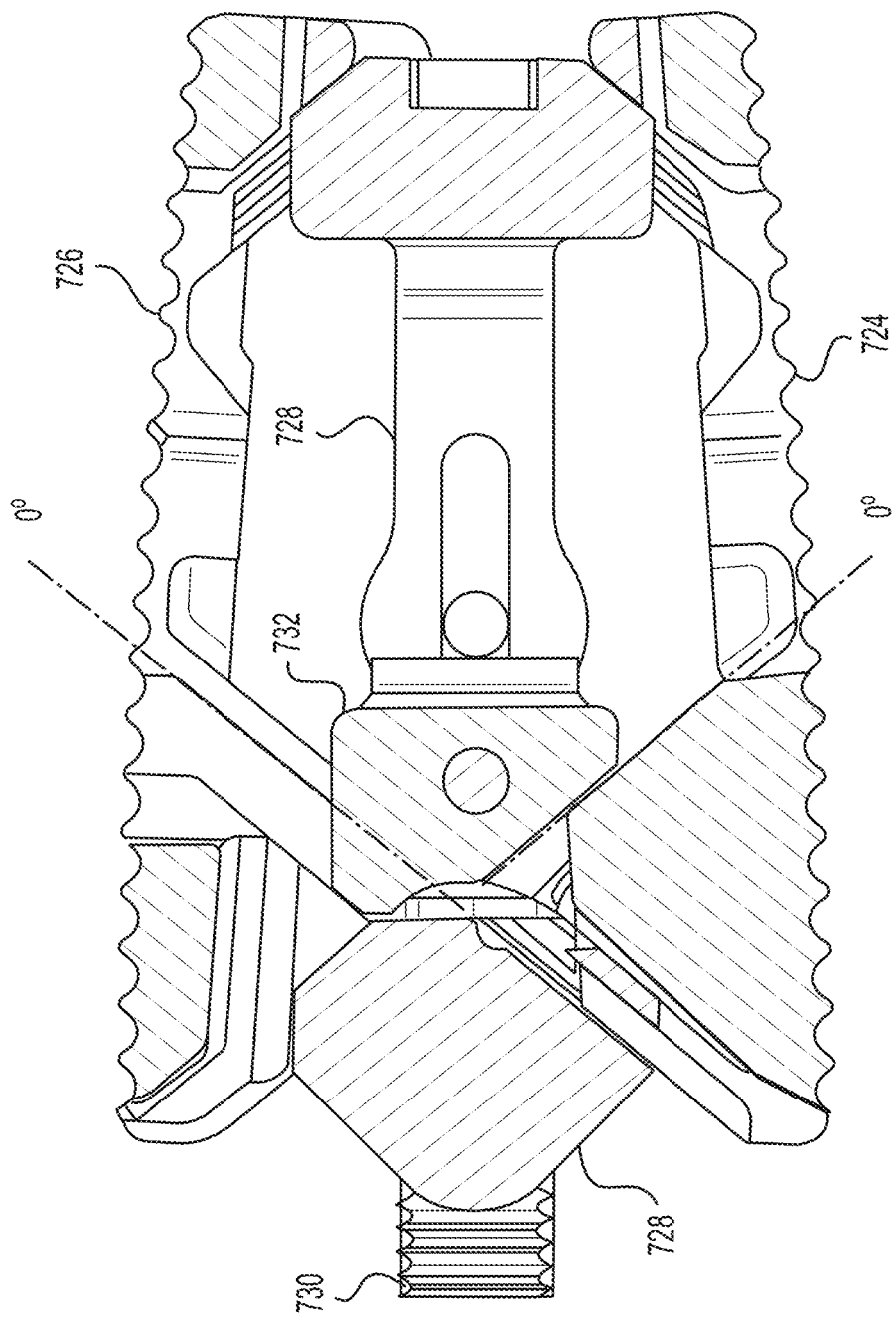

FIGS. 85A-85C are different views of the expandable fusion device of FIG. 79 in a fully expanded state according to one embodiment of the present invention. As the mid ramp piece 732 is pushed further towards the front end 744 of the body 728 and the corresponding ramps are fully mated, the fusion device 722 will begin to expand in overall height in a parallel fashion. In other words, the anterior and posterior aspects of the device 722 may expand at the same rate. As this happens, the device maintains the same lordosis, allowing the lordotic angle to be maintained throughout the expansion range. For example, the degree of lordosis of the device 722 in the fully expanded state, as shown in FIG. 85B, is the same as the degree of lordosis of the device 722 after the endplates have been tipped, shown in FIG. 84B. However, due to further parallel expansion, the height of the device 722 in the fully expanded state (as shown in FIG. 85B) is greater than the height of the device 722 after the endplates have been tipped (as shown in FIG. 84B).

Figure 86:
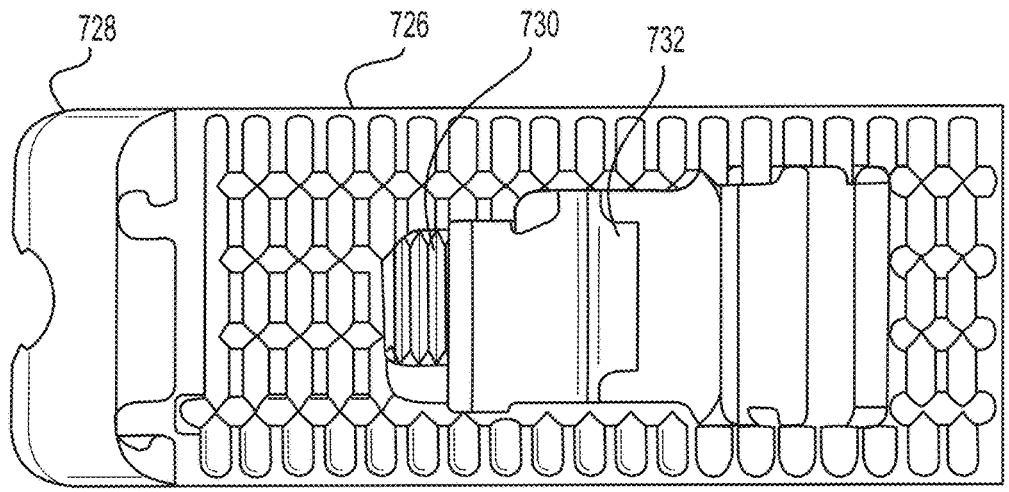
FIG. 86 is a diagram showing an alternative view of the fusion device of FIG. 79 in the locked position.
Figure 87:
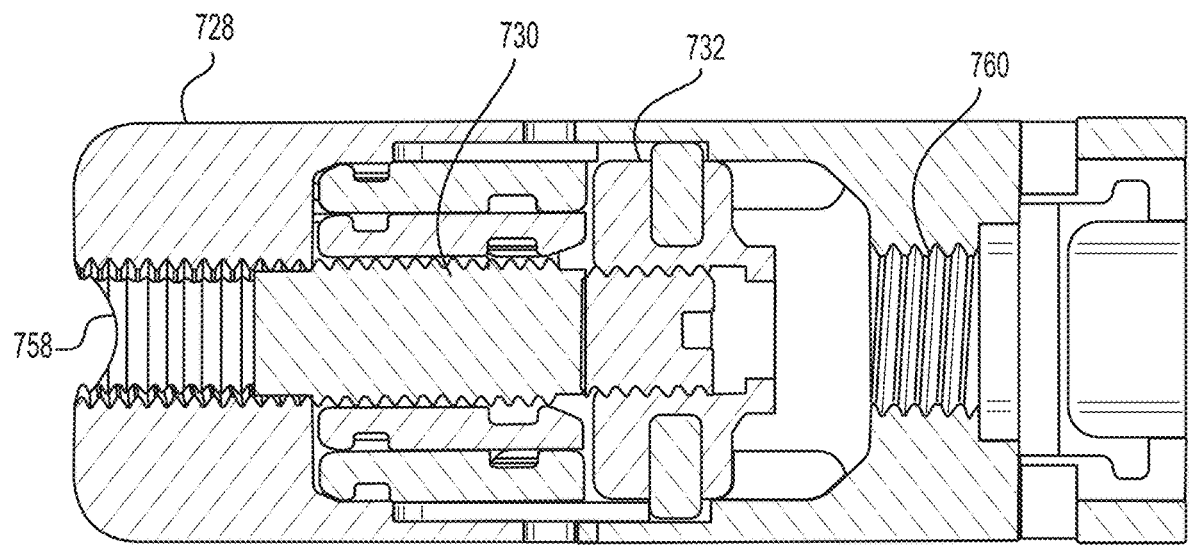
FIG. 87 is a diagram showing another alternative view of the fusion device of FIG. 79 in the locked position.

FIGS. 86-87 show alternative views of the fusion device 722 in the locked position. In one embodiment, the expandable fusion device 722 comprises a disengaged and a locked position, as described above with respect to FIG. 80. According to this embodiment, the fusion device 722 is operable to expand or collapse in the disengaged position and is not capable of movement when in the locked position. The device 722 may start in the locked position when the stem 730 engages with the body 728, as shown in the top down view in FIG. 86 and the cross-sectional view through the middle of the device 722 in FIG. 87. The locked connection is circled in FIG. 87 for illustrative purposes.

Figure 81:
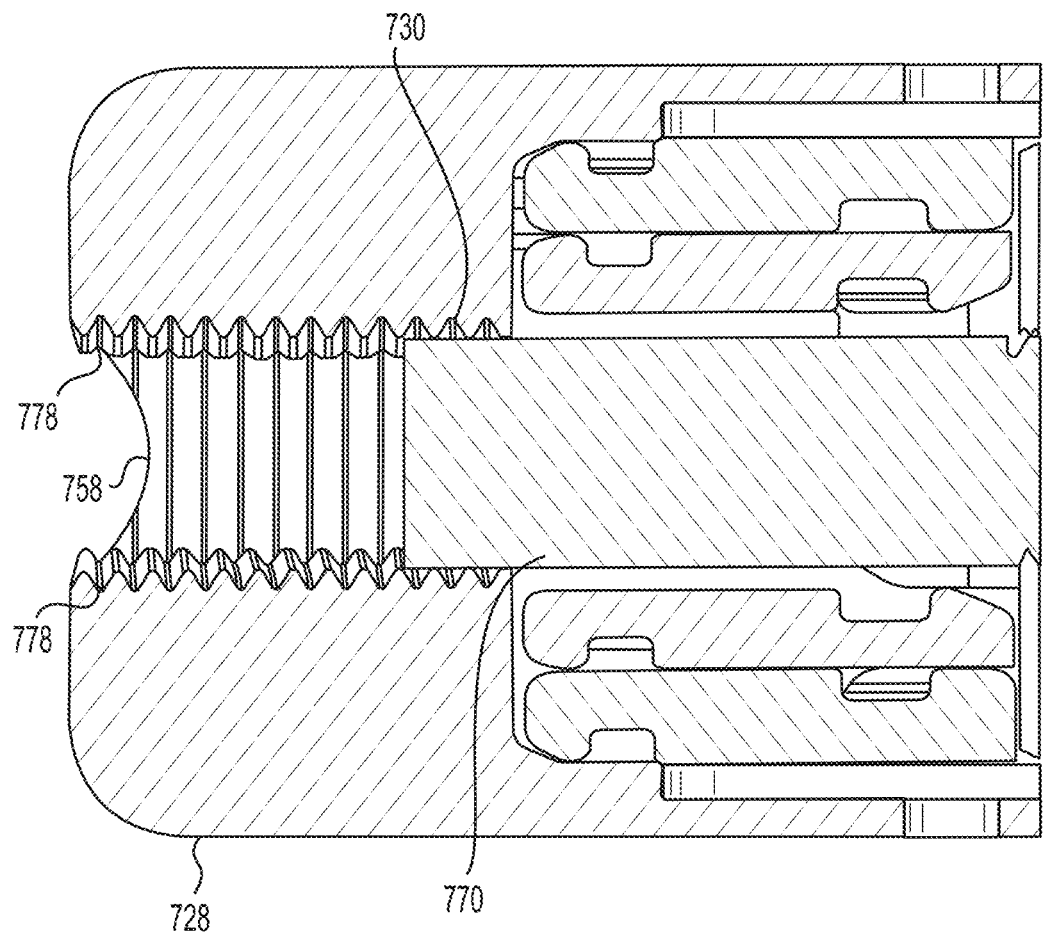
FIG. 81 is a diagram showing a view of an exemplary "disengaged" configuration of the fusion device of FIG. 79.
Figure 88:
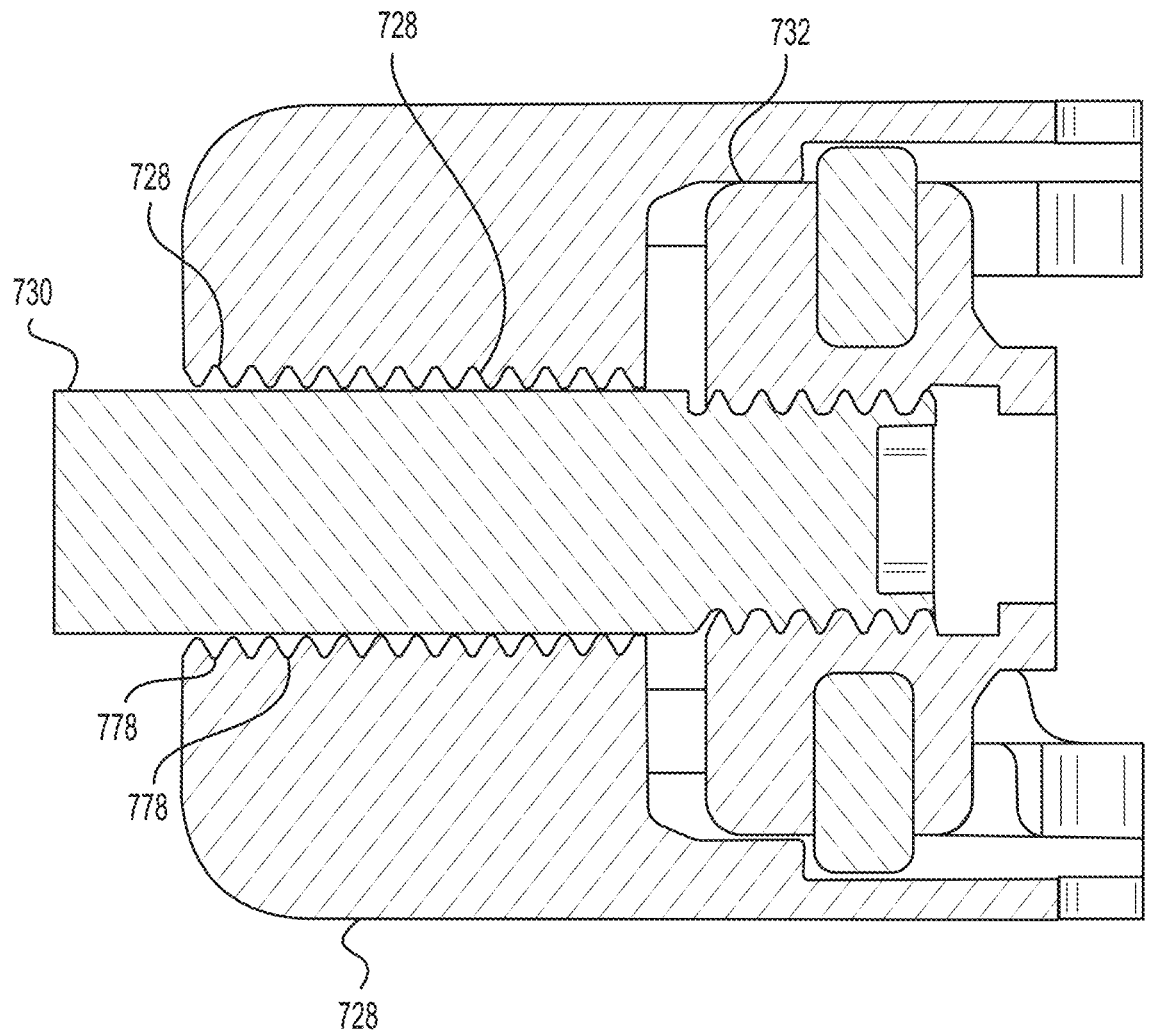
FIG. 88 is a diagram showing the stem's position as the fusion device of FIG. 79 is expanding.

When the user is ready to expand the fusion device 722, the stem 730 is turned, for example, clockwise by 90 degrees, putting the device 722 in the disengaged position with no teeth 772 engaged, as shown in FIG. 81. Once in the released position, the user may drive the device 722 up (expanded) and down (contracted) as desired. FIG. 88 shows the stem's 730 position as the device is expanding (as compared with the stem's 730 position in FIG. 81). The stem 730 advantageously moves continuously through the front throughbore 758, in one embodiment, when in the disengaged position. The teeth 772 of the stem 730 (circled in FIG. 80) may be configured and dimensioned to drive the overall height requirements of the fusion device 722. For instance, the teeth 722 may be configured and dimensioned with 0.5 mm height increments. In this embodiment, the tooth 722 profile may be substantially similar to a M3.5× 0.45 thread profile, except that the cuts are not helical like threads but spherical like grooves. The 0.45 mm "pitch" may comprise the increment that drives the overall height expansion discussed above. These non-continuous increments drive height increases. In some embodiments, the height increases can increase in increments between about 0.2 mm and about 0.8 mm. In other embodiments, the height increases are in increments of approximately 0.5 mm.

Figure 89:
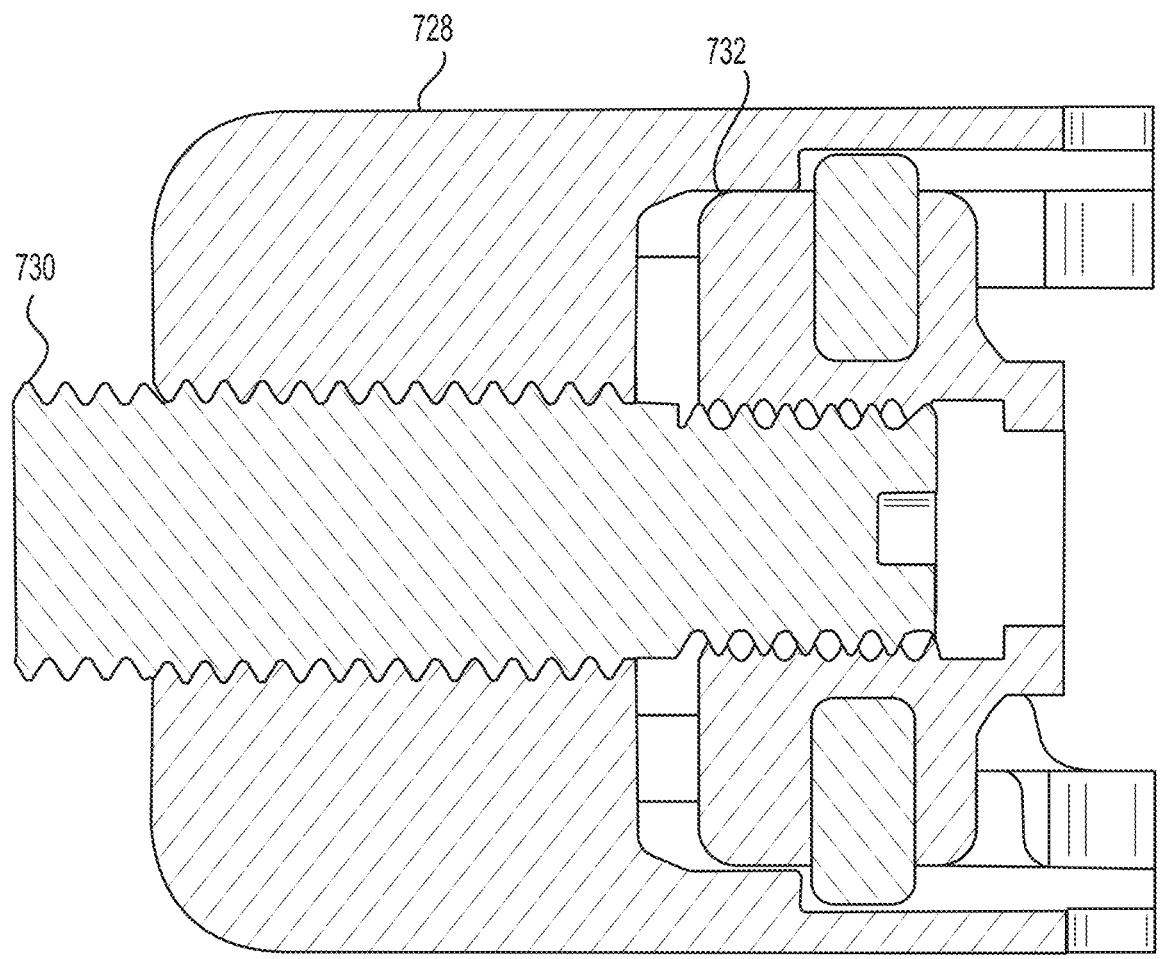
FIG. 89 is a diagram showing the fusion device of FIG. 79 in a locked position.

When the user is satisfied with the magnitude of expansion of the fusion device 722, the stem 730 may be turned, for example, counterclockwise by 90 degrees such that the teeth 772 of the stem 730 engage with the recesses 778 in the front throughbore 758 of the body 728, locking the implant as shown in FIG. 89. Any expansion tool known to those skilled in the art may be used to engage with the stem 730, such as the tool described with respect to FIGS. 78B and 78C. Advantageously, the expandable fusion devices described above are each capable of being inserted through a minimal incision, as the devices can maintain a minimal profile prior to expansion.

The disclosure being thus described, it will be obvious that the same may be varied in many ways. Such variations are not to be regarded as a departure from the spirit and scope of the invention, and all such modifications as would be obvious to one skilled in the art are intended to be included within the scope of the following claims. Although various embodiments are described separately herein for the purposes of facilitating their descriptions, those skilled in the art will understand that various aspects of each embodiment may be combined with other embodiments as desired.

The invention claimed is:

1. An implantable system, comprising:
   an expandable device, comprising:
      a first endplate including a first ramped surface having a first angle and a second ramped surface having a second angle;
      a second endplate operatively connected to the first endplate;
      a body positioned between the first endplate and the second endplate, the body including a third ramped surface having a third angle;
      a middle ramped piece including a fourth ramped surface having a fourth angle, wherein the first endplate and the second endplate are operable to move lordotically when there is a difference between the first angle and the third angle and wherein the first endplate and the second endplate are operable to move in parallel when there is no difference between the first angle and the third angle,
      at least two ramp pins configured to be positioned within at least two openings of the middle ramped piece and extending into at least two slots of the body, wherein the at least two ramp pins slide along the at least two slots of the body to allow the middle ramped piece to translate within the body.

2. The implantable system of claim 1, wherein the first endplate and the second endplate are operable to move lordotically when there is a difference between the second angle and the fourth angle.

3. The implantable system of claim 1, wherein the first endplate and the second endplate are operable to move in parallel when there is no difference between the second angle and the fourth angle.

4. The implantable system of claim 1, wherein a degree of lordosis of the first endplate and the second endplate does not increase when there is no difference between the first angle and the third angle.

5. The implantable system of claim 1, wherein a degree of lordosis of the first endplate and the second endplate does not increase when there is no difference between the second angle and the fourth angle.

6. The implantable system of claim 1, wherein the middle ramped piece comprises a stem, and wherein at least a portion of the stem includes teeth.

7. The implantable system of claim 6, wherein the body comprises an opening that is configured and dimensioned to be engagable with the teeth.

8. The implantable system of claim 7, wherein the first endplate and second endplate do not move with respect to one another when the teeth are engaged with the opening.

9. The implantable system of claim 7, wherein the first endplate and the second endplate are operable to move lordotically when the teeth are disengaged from the opening.

10. The implantable system of claim 7, wherein the first endplate and the second endplate are operable to move in parallel when the teeth are disengaged from the opening.

* * * * *